United States Patent
Shabat et al.

(10) Patent No.: US 11,931,429 B2
(45) Date of Patent: Mar. 19, 2024

(54) CHEMILUMINESCENT PROBES FOR DIAGNOSTICS AND IN VIVO IMAGING

(71) Applicant: RAMOT AT TEL-AVIV UNIVERSITY LTD., Tel-Aviv (IL)

(72) Inventors: Doron Shabat, Tel-Aviv (IL); Ronit Satchi-Fainaro, Tel Aviv (IL); Nir Hananya, Mitzpe Netofa (IL); Ori Green, Tel Aviv (IL); Tal Eilon, Tel Aviv (IL)

(73) Assignee: RAMOT AT TEL-AVIV UNIVERSITY LTD., Tel-Aviv (IL)

( * ) Notice: Subject to any disclaimer, the term of this patent is extended or adjusted under 35 U.S.C. 154(b) by 323 days.

(21) Appl. No.: 17/451,536

(22) Filed: Oct. 20, 2021

(65) Prior Publication Data

US 2022/0047725 A1    Feb. 17, 2022

Related U.S. Application Data

(62) Division of application No. 16/850,333, filed on Apr. 16, 2020, now Pat. No. 11,179,482, which is a division of application No. 16/072,848, filed as application No. PCT/IL2017/050088 on Jan. 24, 2017, now Pat. No. 10,660,974.

(60) Provisional application No. 62/431,618, filed on Dec. 8, 2016, provisional application No. 62/287,127, filed on Jan. 26, 2016.

(51) Int. Cl.
| | |
|---|---|
| *A61K 49/00* | (2006.01) |
| *C07D 321/00* | (2006.01) |
| *C07F 5/02* | (2006.01) |
| *C07F 5/04* | (2006.01) |
| *C07F 7/18* | (2006.01) |
| *C07F 9/12* | (2006.01) |
| *C07F 9/655* | (2006.01) |
| *C07H 15/203* | (2006.01) |
| *C07H 15/26* | (2006.01) |
| *C09B 11/24* | (2006.01) |
| *C09B 23/01* | (2006.01) |
| *C09B 23/04* | (2006.01) |
| *C09B 23/08* | (2006.01) |
| *C09K 11/06* | (2006.01) |

(52) U.S. Cl.
CPC ........ *A61K 49/0052* (2013.01); *C07D 321/00* (2013.01); *C07F 5/025* (2013.01); *C07F 5/04* (2013.01); *C07F 7/1804* (2013.01); *C07F 9/12* (2013.01); *C07F 9/65512* (2013.01); *C07H 15/203* (2013.01); *C07H 15/26* (2013.01); *C09B 11/24* (2013.01); *C09B 23/0066* (2013.01); *C09B 23/04* (2013.01); *C09B 23/083* (2013.01); *C09K 11/06* (2013.01); *C09K 2211/1018* (2013.01)

(58) Field of Classification Search
CPC .... A61K 49/00; C07D 321/00; C07D 493/04; C09K 11/06
See application file for complete search history.

(56) References Cited

U.S. PATENT DOCUMENTS

| | | | |
|---|---|---|---|
| 7,781,229 B2 * | 8/2010 | Giri ...................... | G01N 33/531 436/127 |
| 2016/0329508 A1 | 11/2016 | Saito et al. | |
| 2017/0077424 A1 | 3/2017 | Ohuchi et al. | |

FOREIGN PATENT DOCUMENTS

| | | |
|---|---|---|
| WO | WO 90/07511 A1 | 7/1990 |
| WO | WO 2006/073424 A2 | 7/2006 |

OTHER PUBLICATIONS

Office Action issued by the Brazilian Patent Office in BR122022024633-8, dated Jul. 10, 2023 (in 5 pages).
Hananya, Nir, et al.; "Remarkable Enhancement of Chemiluminescent Signal by Dioxetane-Fluorophore Conjugates: Turn-ON Chemiluminescence Probes with Color Modulation for Sensing and Imaging." Journal of the American Chemical Society 21 vol. 138, Issue 40, pp. 13438-13446. (2016).
International Search Report for PCT/IL2017/050088 dated May 22, 2017 in 6 pages.
Written Opinion for PCT/IL2017/050088 dated May 22, 2017 in 6 pages.

* cited by examiner

*Primary Examiner* — Michael G. Hartley
*Assistant Examiner* — Jagadishwar R Samala
(74) *Attorney, Agent, or Firm* — Knobbe Martens Olson & Bear LLP

(57) ABSTRACT

The present invention provides dioxetane-based chemiluminescence probes, more specifically fluorophore-tethered dioxetane-based chemiluminescence probes and compositions thereof. The chemiluminescence probes disclosed are useful for both diagnostics and in vivo imaging.

10 Claims, 12 Drawing Sheets

CHEMILUMINESCENT PROBES FOR DIAGNOSTICS AND IN VIVO IMAGING

TECHNICAL FIELD

The present invention provides various dioxetane-based chemiluminescence probes and compositions thereof.

Abbreviations: AcOH, acetic acid; ACN, acetonitrile; BBBPY, 4,4'-di-tert-butyl-2,2'-dipyridyl; CIEEL, chemically initiated electron exchange luminescence; DCM, dichloromethane; DEAD, diethyl azodicarboxylate; DMAP, 4-dimethylaminopyridine; DMF, N,N'-dimethylformamide; DMSO, dimethyl sulfoxide; ET, energy transfer; EtOAc, ethylacetate; Hex, hexane; LDA, lithium diisopropylamide; McOH, methanol; NHS, N-hydroxysuccinimide; NIR, near-infrared; NIS, N-iodosuccinimide; PBS, Phosphate buffered saline; QCy, quinone-cyanine; RP-HPLC, reverse-phase high pressure liquid chromatography; RLU, relative light unit; RT, room temperature; TBAF, tetra-n-butylammonium fluoride; TBDMS, tert-butyldimethylsilyl; TBDPS, tert-butyldiphenylsilyl; TBS, tert-butyldimethylsilyl; TBSCl, tert-butyldimethylsilyl chloride; TEMP, 2,2,6,6-tetramethylpiperidine; TFA, trifluoroacetic acid; THF, tetrahydrofuran; TLC, thin layer chromatography; TMS-Cl, trimethylsilyl chloride.

BACKGROUND ART

Chemiluminescence assays are widely utilized in various chemical and biological applications due to their sensitivity and high signal-to-noise ratio (Roda and Guardigli, 2012; Roda et al., 2005). Unlike fluorescence-based assays, in chemiluminescence no light excitation is required. Therefore, background signal arising from autofluorescence does not exist when chemiluminescence is used. Such circumstance makes chemiluminescence especially useful for tissue and whole-body imaging (Gross et al., 2009; Zhang et al., 2013; Van de Bittner et al., 2013; Porterfield et al., 2015).

Most of the chemiluminescent compounds, currently in use, are activated by oxidation; i.e., a stable precursor is oxidized usually by hydrogen peroxide, to form an oxidized high-energy intermediate, which then decomposes to generate an excited species. The latter decays to its ground state by either light emission or by energy transfer. Common probes that act on such chemiluminescence mechanism are usually based on luminol (Merényi et al., 1990) and oxalate esters (Silva et al., 2002). Utilizing this oxidation-activated chemiluminescence mode-of-action, several systems were developed for the in vivo imaging of reactive oxygen species (ROS) (Lee et al., 2007; Kielland et al., 2009; Lim et al., 2010; Cho et al., 2012; Lee et al., 2012; Shuhendler et al., 2014; Lee et al., 2016; Li et al., 2016).

Innately, chemiluminescence that is exclusively activated by oxidation is limited for the detection and imaging of ROS. However, in 1987 Paul Schaap developed a new class of chemiluminescent probes, which can be activated by an enzyme or an analyte of choice (Schaap et al., 1987a-c). As depicted in Scheme 1, Schaap's adamantylidene-dioxetane based chemiluminescence probe (structure I) is equipped with an analyte-responsive protecting group used to mask the phenol moiety of the probe. Removal of the protecting group by the analyte of interest generates an unstable phenolate-dioxetane species II, which decomposes through a chemiexcitation process to produce the excited intermediate benzoate ester III and adamantanone. The excited intermediate decays to its ground-state (benzoate ester IV) through emission of a blue light photon.

Scheme 1: Chemiluminescent Activation Pathway of Schaap's Adamantylidene-Dioxetane

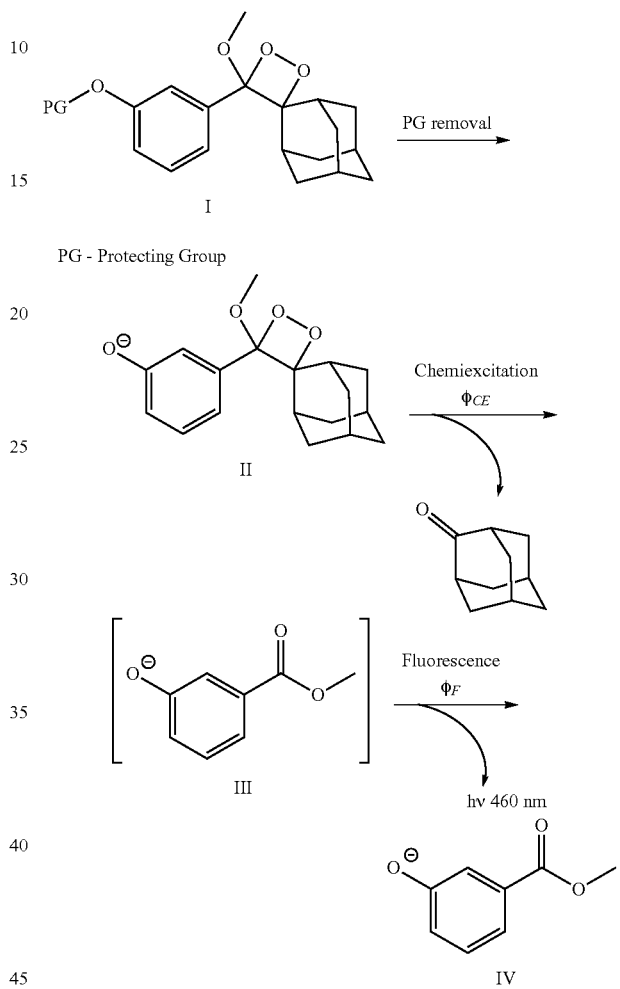

In bioassays, under aqueous conditions, Schaap's dioxetanes suffer from one major limitation; their chemiluminescence efficiency decreases significantly through non-radiative energy transfer processes (quenching) by interaction with water molecules (Matsumoto, 2004). A common way to amplify the chemiluminescence signal of Schaap's dioxetanes is achieved through energy transfer from the resulting excited species (benzoate ester III) to a nearby acceptor, which is a highly emissive fluorophore under aqueous conditions (Park et al., 2014; Tseng and Kung, 2015). Therefore, a surfactant-dye adduct is usually added in commercial chemiluminescent immunoassays. The surfactant reduces water-induced quenching by providing a hydrophobic environment for the excited chemiluminescent probe, which transfers its energy to excite a nearby fluorogenic dye. Consequently, the low-efficiency luminescence process is amplified up to 400-fold in aqueous medium (Schaap et al., 1989). However, since the surfactant mode-of-action relies on micelles formation, its functional concentration is relatively high (above the critical micelle concentration)

(Dominguez et al., 1997). As micellar structures are not maintained when animals are treated systemically, the surfactant-dye adduct approach is not practical for in vivo detection or imaging of biological activity generated by enzymes or chemical analytes (Torchilin, 2001).

To overcome the limitation of a two-component system (a dioxetane probe and a surfactant-fluorescent dye adduct), a single component comprised of dioxetane conjugated with fluorophore is required. Two previous reports have described synthesis of dioxetane-fluorogenic dye conjugates, in which the dioxetane effectively transfers chemiluminescence energy to the tethered fluorophore to emit light at a wavelength that can be varied by choice of fluorophore (WO 1990007511; Watanabe et al., 2012). In addition to signal amplification, tethering of dioxetane with fluorophore also allows color modulation and red-shifting of the emitted light; a significant requirement for bioimaging applications (Matsumoto et al., 2008; Loening et al., 2010; Branchini et al., 2010; McCutcheon et al., 2012; Jathoul et al., 2014; Steinhardt et al., 2016).

SUMMARY OF INVENTION

Disclosed herein are two approaches for improving the chemiluminescence of the Schaap's adamantylidene-dioxetane based chemiluminescence probe.

According to one approach wherein chemiluminescence emission is amplified through an indirect pathway (Study 1 herein), the Schaap's adamantylidene-dioxetane based probe is conjugated to a fluorescent dye mew to the analyte-responsive protecting group, via a linker. As shown in Scheme 2 (upper panel), the dioxetane-fluorophore conjugate thus obtained decomposes upon its activation to generate a benzoate derivative like intermediate V, and its chemiluminescent emission is significantly amplified under physiological conditions through the energy transfer mechanism from the excited benzoate to the fluorescent dye.

Study 1 shows a simple and practical synthetic route for preparation of such fluorophore-tethered dioxetane chemiluminescent probes. The effectiveness of the synthesis is based on a late-stage functionalization of a dioxetane precursor by Hartwig-Miyaura C—H borylation, followed by subsequent Suzuki coupling and oxidation to dioxetane. The obtained intermediate is composed of a reactive NHS-ester-dioxetane ready for conjugation with any fluorophore-amine derivative. The chemiluminescent emission of the fluorophore-tethered dioxetane probes was significantly amplified in comparison to a classic dioxetane probe through an energy transfer mechanism. The synthesized probes produced light of various colors that matched the emission wavelength of the excited tethered fluorophore. Using the synthetic route exemplified, two fluorophore-tethered dioxetane probes designed for activation by β-galactosidase and conjugated with green (fluorescein) and NIR (QCy) fluorescent dyes were synthesized. Both probes were able to provide chemiluminescence in vivo images following subcutaneous injection after activation by β-galactosidase; however, a chemiluminescence image following intraperitoneal injection was observed only by the NIR probe. These are the first in vivo images produced by Schaap's dioxetane-based chemiluminescence probes with no need of any additive. The NIR probe was also able to image cells by chemiluminescence microscopy, based on endogenous activity of β-galactosidase.

The intermediates obtained following functionalization of a dioxetane precursor by Hartwig-Miyaura C—H borylation are referred to herein as compounds of the formula I, and those obtained after further Suzuki coupling and oxidation are referred to herein as compounds of the formula IIa/IIb. The fluorophore-tethered dioxetane-based chemiluminescence probes disclosed are referred to herein as compounds (or conjugates) of the formula IIIa/IIIb.

According to another approach wherein chemiluminescence emission is amplified through a direct mode of action (Study 2 herein), the Schapp's adamantylidene-dioxetane probe is substituted at the ortho position of the phenolic ring with a $\pi^*$ acceptor group such as an acrylate and acrylonitrile electron-withdrawing group so as to increase the emissive nature of the benzoate species (Scheme 2, lower panel). To the best of our knowledge, the influence of electron acceptor substituents on the aromatic moiety of dioxetane chemiluminescence probes was never studied before for physiologically-relevant pHs.

Study 2 shows the preparation of such chemiluminescence probes with high efficiency yield under physiological conditions. The chemiluminescence quantum yield of the best probe was greater than three orders of magnitude in comparison to the standard commercially available adamantylidene-dioxetane probe. Importantly, one of the probes prepared was able to provide high quality chemiluminescence cell images based on endogenous activity of β-galactosidase, demonstrating for the first time cell-imaging achieved by non-luciferin small molecule based probe with direct chemiluminescence mode of emission. The chemiluminescence probes shown in this Study are referred to herein as compounds of the formula IVa/IVb.

Scheme 2: Indirect Chemiluminescence
Amplification Obtained by Energy Transfer to a
Fluorogenic Dye Vs. Direct Chemiluminescence
Mode Obtained by a Substituent Effect

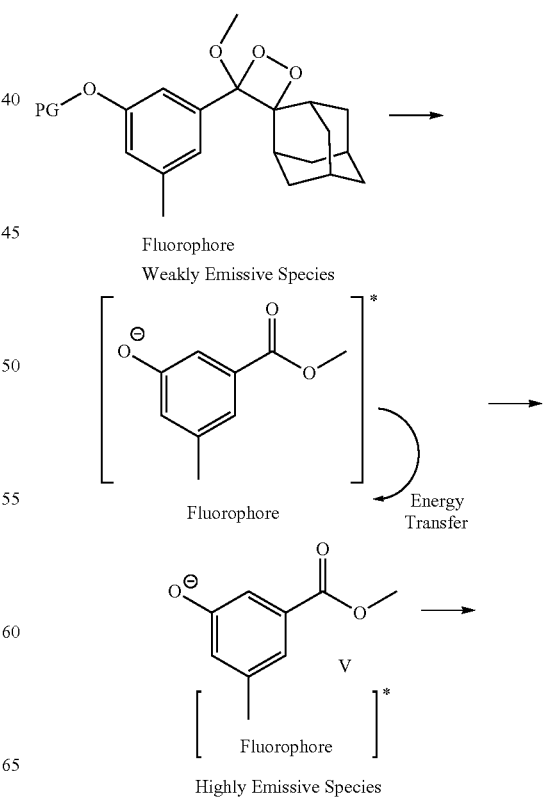

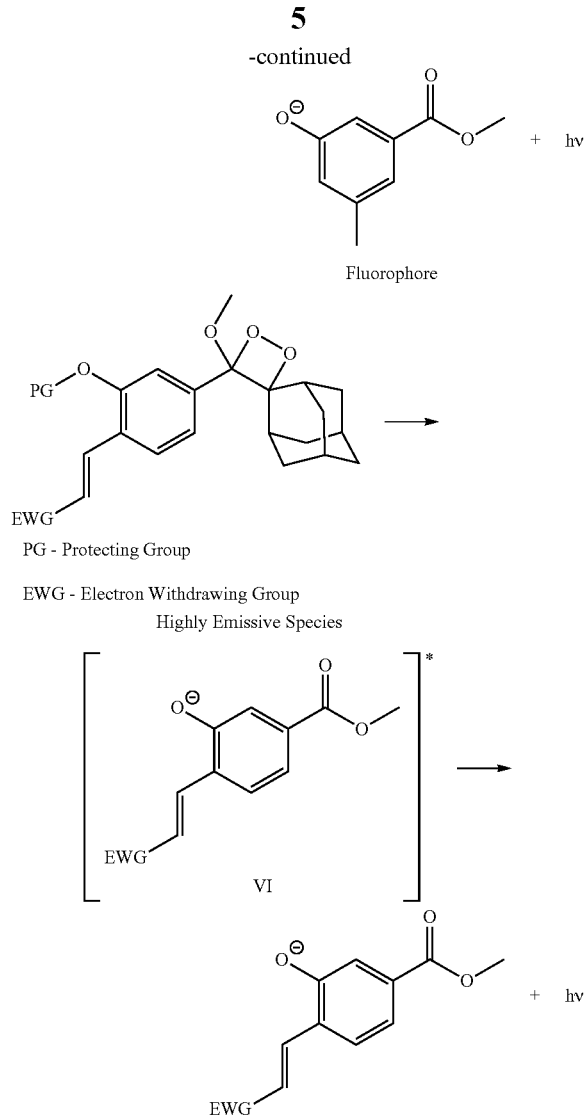

PG - Protecting Group

EWG - Electron Withdrawing Group

In certain aspects, the present invention thus provides a fluorophore-tethered dioxetane-based chemiluminescence probe of the formula IIIa/IIIb as defined herein, as well as intermediates for the preparation thereof referred to herein as compounds of the formulas I and IIa/IIb as defined herein; and a π* acceptor group-containing dioxetane based chemiluminescence probe of the formula IVa/IVb as defined herein.

In a further aspect, the present invention provides a composition comprising a carrier, e.g., a pharmaceutically acceptable carrier, and either a conjugate of the formula IIIa/IIIb or a compound of the formula IVa/IVb. The composition of the invention may be used for diagnostics as well as for in vivo imaging of reporter genes, enzymes, and chemical analytes.

DMSO) in the presence of 1.5 units/mL β-galactosidase (13B) (left panel), and count of total emitted photon (right panel).

Figure 14:
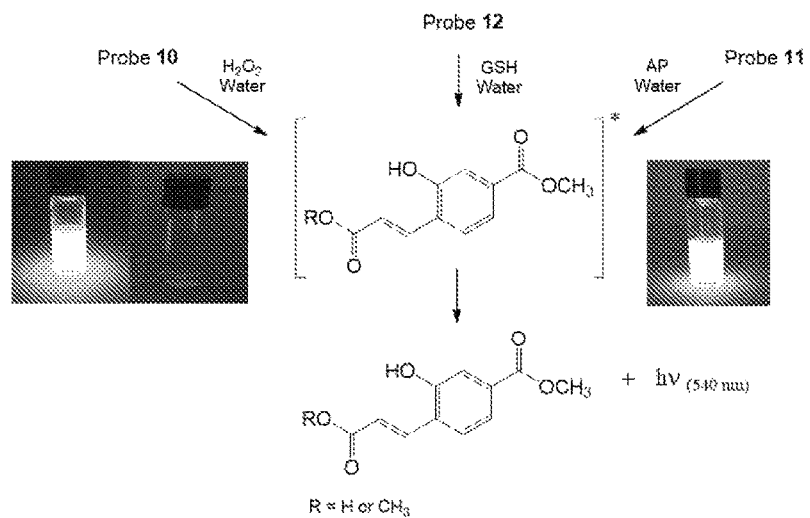

FIG. 14 shows water soluble chemiluminescence probes for detection of hydrogen peroxide (Probe 10) and alkaline-phosphatase (AP) (Probe 11), which produce visible bright green luminescence under aqueous conditions. On the left—a comparison between light emission observed by Probe 10 (1 mM; left vial) to that observed by Luminol (1 mM; right vial) upon incubation with hydrogen peroxide under aqueous conditions at pH 10. Probe 12 is a chemiluminescence for detection of GSH.

Figure 15A:
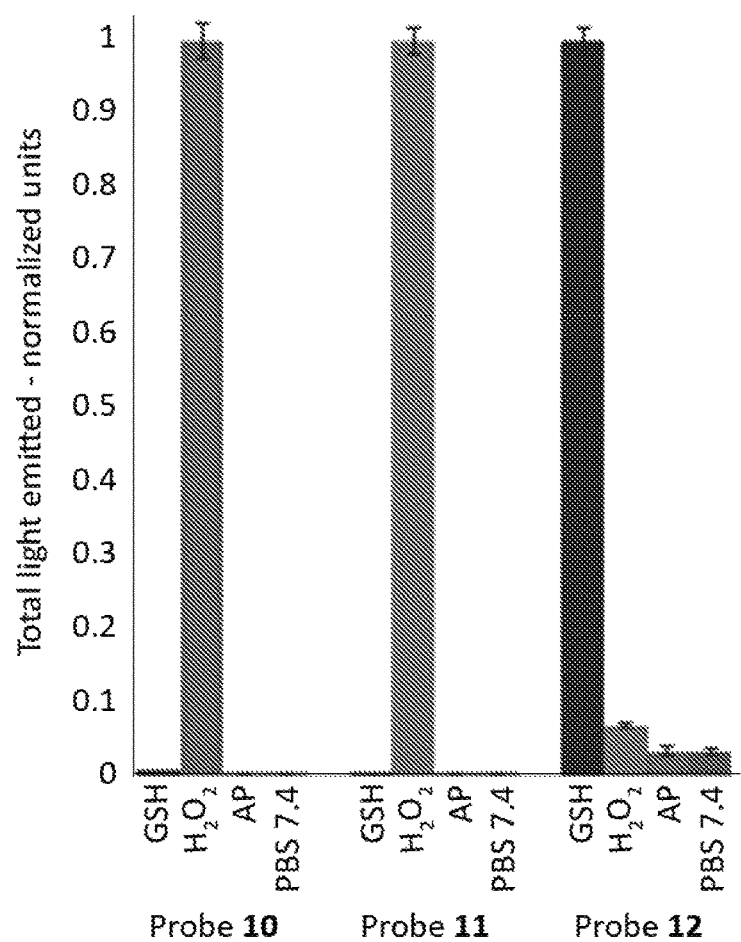
Figure 15B:
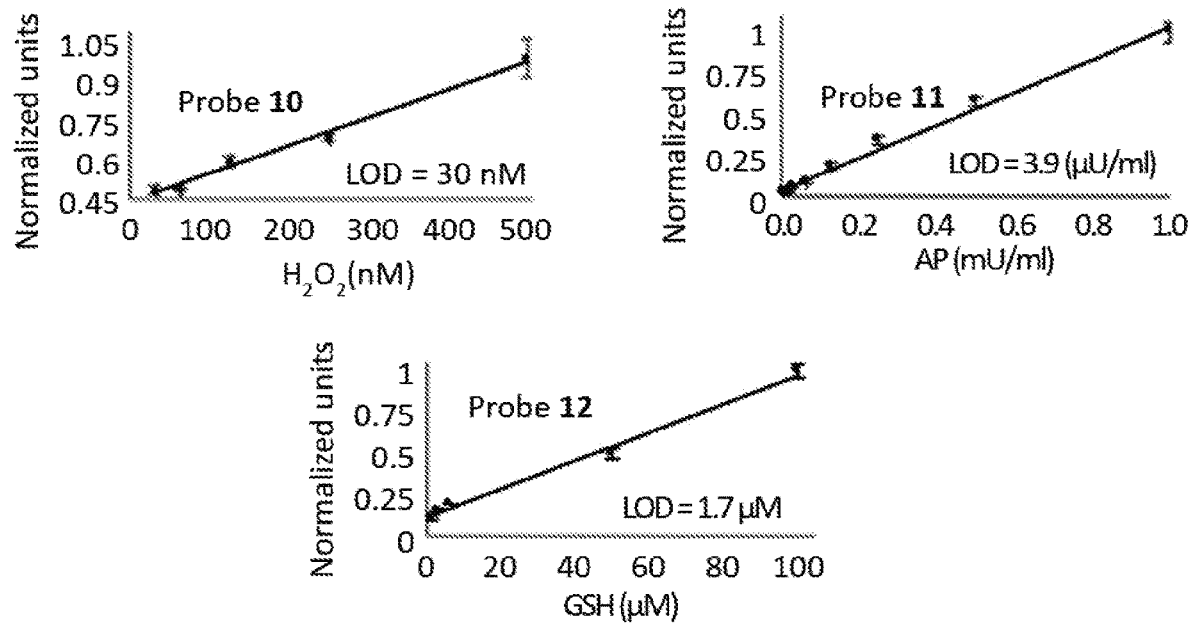

FIGS. 15A-15B show (15A) total light emitted from Probe 10 (100 μM), Probe 11 (10 μM) and Probe 12 (10 μM) in the presence of hydrogen peroxide (1 mM), alkaline phosphatase (AP) (1.5 EU/ml) or glutathione (1 mM). Measurements were conducted in PBS (100 mM), pH 7.4, with 10% DMSO at RT; and (15B) total light emitted from Probe 10 (500 μM), Probe 11 (500 μM) and Probe 12 (10 μM) in PBS (100 mM), pH 7.4 with 10% DMSO over a period of 1 h, with various concentration of the corresponding stimulus. A detection limit (blank control+3 SD) was determined for each probe.

Figure 16:
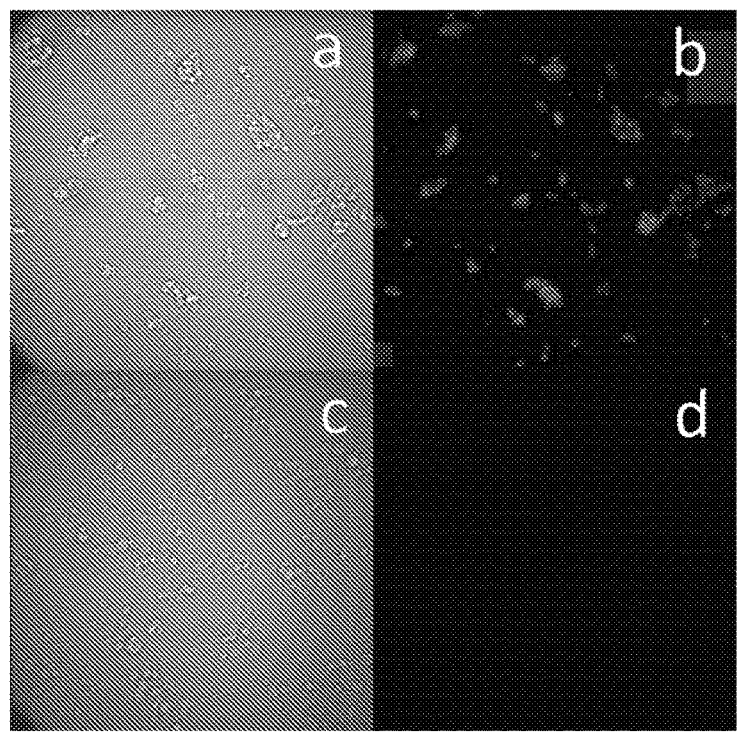

FIG. 16 shows (a) transmitted light image and (b) chemiluminescence microscopy of HEK293-LacZ stable cells; and (c) transmitted light image and (d) chemiluminescence microscopy of HEK293-WT cells. Images were obtained following 20 min incubation with cell culture medium containing Probe 7 (5 μM). Images were taken by the LV200 Olympus-microscope using 60× objective and 40s exposure time.

DETAILED DESCRIPTION

In one aspect, the present invention provides a compound of the formula I:

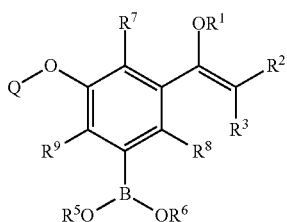

I wherein
R$^1$ is selected from a linear or branched (C$_1$-C$_{18}$)alkyl, or (C$_3$-C$_7$)cycloalkyl;
R$^2$ and R$^3$ each independently is selected from a branched (C$_3$-C$_{18}$)alkyl or (C$_3$-C$_7$)cycloalkyl, or R$^2$ and R$^3$ together with the carbon atom to which they are attached form a fused, spiro or bridged cyclic or polycyclic ring;
R$^5$ and R$^6$ each independently is selected from H, (C$_1$-C$_{18}$)alkyl, (C$_2$-C$_{18}$)alkenyl, (C$_2$-C$_{18}$)alkynyl, (C$_3$-C$_7$)cycloalkyl, or aryl, or R$^5$ and R$^6$ together with the oxygen atoms to which they are attached form a heterocyclic ring;
R$^7$, R$^8$ and R$^9$ each independently is H, or an electron acceptor group such as halogen, —NO$_2$, —CN, —COOR$^{10}$, —C(=O)R$^{10}$ and —SO$_2$R$^{10}$;
R$^{10}$ each independently is H or —(C$_1$-C$_{18}$)alkyl; and Q is a protecting group such as —CH$_3$, —CH$_2$OCH$_3$, —C(=O)C(CH$_3$)$_3$, —CH$_2$—CH=CH$_2$, TBDMS, TBDPS, benzyl, and 2-nitro-4,5-dimethoxybenzyl.

The term "alkyl" typically means a linear or branched hydrocarbon radical having, e.g., 1-18 carbon atoms and includes methyl, ethyl, n-propyl, isopropyl, n-butyl, sec-butyl, isobutyl, tert-butyl, n-pentyl, 2,2-dimethylpropyl, n-hexyl, n-heptyl, n-octyl, and the like. The terms "alkenyl" and "alkynyl" typically mean linear and branched hydrocarbon radicals having, e.g., 2-18 carbon atoms and one or more double or triple bond, respectively, and include ethenyl, propenyl, 3-buten-1-yl, 2-ethenylbutyl, 3-octen-1-yl, and the like, and propynyl, 2-butyn-1-yl, 3-pentyn-1-yl, and the like.

The term "alkylene" refers to a linear or branched divalent hydrocarbon radical having, e.g., 1-18 carbon atoms; and the terms "alkenylene" and "alkynylene" typically mean linear or branched divalent hydrocarbon radicals having, e.g., 2-18 carbon atoms, and one or more double or triple bonds, respectively. Examples of alkylenes include, without being limited to, methylene, ethylene, propylene, butylene, 2-methylpropylene, pentylene, 2-methylbutylene, hexylene, 2-methylpentylene, 3-methylpentylene, 2,3-dimethylbutylene, heptylene, octylene, n-tridecanylene, n-tetradecanylene, n-pentadecanylene, n-hexadecanylene, n-heptadecanylene, n-octadecanylene, n-nonadecanylene, icosanylene, henicosanylene, docosanylene, tricosanylene, tetracosanylene, pentacosanylene, and the like. Non-limiting examples of alkenylenes include 2-, 3-, 4-, 5- and 6-tridecenylene, tetradecenylenes such as myristoleylene, 2-, 3-, 4-, 5-, 6- and 7-pentadecenylene, hexadecenylenes such as palmitoleylene, 2-, 3-, 4-, 5-, 6-, 7- and 8-heptadecenylene, octadecenylenes such as oleylene, linoleylene, α-linoleylene, and the like; and non-limiting examples of alkynylenes include tridec-6-ynylene, undec-4-ynylene, and the like.

The term "cycloalkyl" means a mono- or bicyclic saturated hydrocarbyl group having, e.g., 3-7 carbon atoms such as cyclopropyl, cyclobutyl, cyclopentyl, cyclohexyl, cycloheptyl, and the like, that may be substituted, e.g., by one or more alkyl groups. The terms "cycloalkylene" and "cycloalkenylene" mean mono- or bicyclic hydrocarbyl groups having, e.g., 3-7 carbon atoms, and one or more double or triple bonds, respectively.

The term "heterocyclic ring" as used herein denotes a mono- or poly-cyclic non-aromatic ring of, e.g., 5-12 atoms containing at least two carbon atoms and at least three heteroatoms selected from sulfur, oxygen, nitrogen and boron, which may be saturated or unsaturated, i.e., containing at least one unsaturated bond. Preferred are 5- or 6-membered heterocyclic rings. The heterocyclic ring may be substituted at any of the carbon atoms of the ring, e.g., by one or more alkyl groups. Non-limiting examples of such radicals include 4,5-di-tert-butyl- 1,3,2-dioxaborolanyl and 4,4,5,5-tetramethyl-1,3,2-dioxaborolanyl.

The term "aryl" denotes an aromatic carbocyclic group having, e.g., 6-14, carbon atoms consisting of a single ring or condensed multiple rings such as, but not limited to, phenyl, naphthyl, phenanthryl, and biphenyl. The aryl may optionally be substituted by one or more groups each independently selected from halogen, (C$_1$-C$_8$)alkyl, —O—(C$_1$-C$_8$)alkyl, —COO(C$_1$-C$_8$)alkyl, —CN, and —NO$_2$. The term "arylene-diyl" refers to a divalent radical derived from an aryl as defined herein by removal of a further hydrogen atom from any of the ring atoms, e.g., phenylene and naphthylene.

The term "heteroaryl" refers to a radical derived, e.g., from a 5-10-membered mono- or poly-cyclic heteroaromatic ring containing one to three, preferably 1-2, heteroatoms selected from N, O, or S. Examples of mono-cyclic heteroaryls include, without being limited to, pyrrolyl, furyl, thienyl, thiazinyl, pyrazolyl, pyrazinyl, imidazolyl, oxazolyl, isoxazolyl, thiazolyl, isothiazolyl, pyridyl, pyrimidinyl, 1,2,3-triazinyl, 1,3,4-triazinyl, and 1,3,5-triazinyl. Polycyclic heteroaryl radicals are preferably composed of two rings such as, but not limited to, benzofuryl, isobenzofuryl, benzothienyl, indolyl, quinolinyl, isoquinolinyl, imidazo[1,2-a]pyridyl, benzimidazolyl, benzthiazolyl, benzoxazolyl, pyrido[1,2-a]pyrimidinyl and 1,3-benzodioxinyl. The heteroaryl may optionally be substituted by one or more groups each independently selected from halogen, $(C_1$-$C_8)$alkyl, —O—$(C_1$-$C_8)$alkyl, —COO$(C_1$-$C_8)$alkyl, —CN, and —NO$_2$. It should be understood that when a polycyclic heteroaryl is substituted, the substitution may be in any of the carbocyclic and/or heterocyclic rings. The term "heteroarylenediyl" denotes a divalent radical derived from a "heteroaryl" as defined herein by removal of a further hydrogen atom from any of the ring atoms.

The term "halogen" as used herein refers to a halogen and includes fluoro, chloro, bromo, and iodo, but it is preferably fluoro or chloro.

The term "amino acid" as used herein refers to an organic compound comprising both amine and carboxylic acid functional groups, which may be either a natural or non-natural amino acid. The twenty two amino acids naturally occurring in proteins are aspartic acid (Asp), tyrosine (Tyr), leucine (Leu), tryptophan (Trp), arginine (Arg), valine (Val), glutamic acid (Glu), methionine (Met), phenylalanine (Phe), serine (Ser), alanine (Ala), glutamine (Gln), glycine (Gly), proline (Pro), threonine (Thr), asparagine (Asn), lysine (Lys), histidine (His), isoleucine (Ile), cysteine (Cys), selenocysteine (Sec), and pyrrolysine (Pyl). Non-limiting examples of other amino acids include citrulline (Cit), diaminopropionic acid (Dap), diaminobutyric acid (Dab), ornithine (Orn), aminoadipic acid, β-alanine, 1-naphthylalanine, 3-(1-naphthyl)alanine, 3-(2-naphthyl)alanine, γ-aminobutiric acid (GABA), 3-(aminomethyl) benzoic acid, p-ethynyl-phenylalanine, p-prop argly-oxy-phenylalanine, m-ethynyl-phenylalanine, p-bromophenylalanine, p-iodophenylalanine, p-azidophenylalanine, p-acetylphenylalanine, norleucine (Nle), azidonorleucine, 6-ethynyl-tryptophan, 5-ethynyl-tryptophan, 3-(6-chloroindolyl)alanine, 3-(6-bromoindolyl)alanine, 3-(5-bromoindolyl)alanine, azidohomoalanine, p-chlorophenylalanine, α-aminocaprylic acid, O-methyl-L-tyrosine, N-acetylgalactosamine-α-threonine, and N-acetylgalactosamine-α-serine.

The term "peptide" refers to a short chain of amino acid monomers (residues), e.g., a chain consisting of 2, 3, 4, 5, 6, 7, 8, 9, 10, 11, 12 or more amino acid residues, linked by peptide bonds, i.e., the covalent bond formed when a carboxyl group of one amino acid reacts with an amino group of another. The term "peptide moiety" as used herein refers to a moiety of a peptide as defined herein after removal of the hydrogen bond from a carboxylic group, i.e., either the terminal or a side chain carboxylic group, thereof. Examples of such peptide moieties include, without being limited to, peptide moieties comprising the amino sequence Phe-Lys, Cit-Val, Gly-Phe-Leu-Gly, Asp-Glu-Val-Asp-, or Gly-Gly-Pro-Nle, or the modified amino acid sequence carboxybenzyl (Cbz) protected-Ala-Ala-Asn-ethylenediamine The term "protecting group" as used herein with respect to the compound of the formula I refers to an alcohol protecting group such as, without limiting, benzoyl, benzyl, methoxymethyl ether, β-methoxyethoxymethyl ether, methoxytrityl (4-methoxyphenyl) diphenylmethyl), dimethoxytrityl (bis-(4-methoxyphenyl)phenylmethyl), p-methoxybenzyl ether, methylthiomethyl ether, pivaloyl, trityl (triphenylmethyl radical), 2-nitro-4,5-dimethoxybenzyl, and silyl ethers, e.g., trimethylsilyl (TMS), TBDMS, tri-iso-propylsilyloxymethyl (TOM), triisopropylsilyl (TIPS), and TBDPS ethers. Particular such protecting groups are —CH$_3$, —CH$_2$OCH$_3$, —C(=O)C(CH$_3$)$_3$, —CH$_2$—CH=CH$_2$, TBDMS, TBDPS, benzyl, and 2-nitro-4,5-dimethoxybenzyl.

The term "electron acceptor group" as used herein refers to a group of atoms with a high electron affinity. Non-limiting examples of such groups include halogen, —NO$_2$, —SO$_2$R, —CN, —C(=O)R, —C(=O)OR, and C(=O)NR$_2$, wherein R each independently may be, e.g., hydrogen, linear or branched $(C_1$-$C_{10})$alkyl, or $(C_4$-$C_{10})$aryl. Particular such electron acceptor groups include halogen, —NO$_2$, —SO$_2$R, —CN, —C(=O)R, and —C(=O)OR, wherein R each independently is H or —$(C_1$-$C_{18})$alkyl.

In certain embodiments, the invention provides a compound of the formula I, wherein $R^1$ is a linear or branched $(C_1$-$C_8)$alkyl, preferably $(C_1$-$C_4)$alkyl, more preferably methyl or ethyl.

In certain embodiments, the invention provides a compound of the formula I, wherein $R^2$ and $R^3$ each independently is a branched $(C_3$-$C_{18})$alkyl or $(C_3$-$C_7)$cycloalkyl. In other embodiments, $R^2$ and $R^3$ each independently is a branched $(C_3$-$C_{18})$alkyl or $(C_3$-$C_7)$cycloalkyl, and together with the carbon atom to which they are attached form a fused, spiro or bridged polycyclic ring. In particular such embodiments, $R^2$ and $R^3$ together with the carbon atom to which they are attached form adamantyl.

In certain embodiments, the invention provides a compound of the formula I, wherein $R^5$ and $R^6$ each independently is $(C_1$-$C_8)$alkyl, preferably $(C_3$-$C_6)$alkyl, more preferably isopropyl, and together with the oxygen atoms to which they are attached form a heterocyclic ring. In particular such embodiments, $R^5$ and $R^6$ each is isopropyl and together with the oxygen atoms to which they are attached form 4,4,5,5-tetramethyl-1,3,2-dioxaborolanyl.

In certain embodiments, the invention provides a compound of the formula I, wherein at least one (i.e., one, two or three) of $R^7$, $R^8$ and $R^9$ is H, and the other of $R^7$, $R^8$ and $R^9$ each independently is an electron acceptor group as defined above. In certain particular such embodiments, $R^7$, $R^8$ and $R^9$ each is H. In other particular such embodiments, $R^7$ is an electron acceptor group as defined above, and $R^8$ and $R^9$ each is H; or $R^8$ is an electron acceptor group as defined above, and $R^7$ and $R^9$ each is H; or $R^9$ is an electron acceptor group as defined above, and $R^7$ and $R^8$ each is H, wherein said electron acceptor group is particularly halogen, —NO$_2$ or —CN.

In certain embodiments, the invention provides a compound of the formula I, wherein $R^1$ is a linear or branched $(C_1$-$C_8)$alkyl, preferably $(C_1$-$C_4)$alkyl, more preferably methyl or ethyl; $R^2$ and $R^3$ each independently is a branched $(C_3$-$C_{18})$alkyl or $(C_3$-$C_7)$cycloalkyl, and together with the carbon atom to which they are attached form a fused, spiro or bridged polycyclic ring; $R^5$ and $R^6$ each independently is $(C_1$-$C_8)$alkyl, preferably $(C_3$-$C_6)$alkyl, more preferably isopropyl, and together with the oxygen atoms to which they are attached form a heterocyclic ring; and at least one of $R^7$, $R^8$ and $R^9$ is H, and the other of $R^7$, $R^8$ and $R^9$ each independently is an electron acceptor group selected from halogen, —NO$_2$ or —CN. In particular such embodiments, $R^2$ and $R^3$ together with the carbon atom to which they are attached form adamantyl; or $R^5$ and $R^6$ each is isopropyl and together with the oxygen atoms to which they are attached form 4,4,5,5-tetramethyl-1,3,2-dioxaborolanyl. In a specific such embodiment, $R^1$ is methyl; $R^2$ and $R^3$ together with the carbon atom to which they are attached form adamantly; $R^5$ and $R^6$ each is isopropyl and together with the oxygen atoms to which they are attached form 4,4,5,5-tetramethyl-1,3,2-dioxaborolanyl; $R^7$, $R^8$ and $R^9$ are H; and Q is TBDMS (compound I-1).

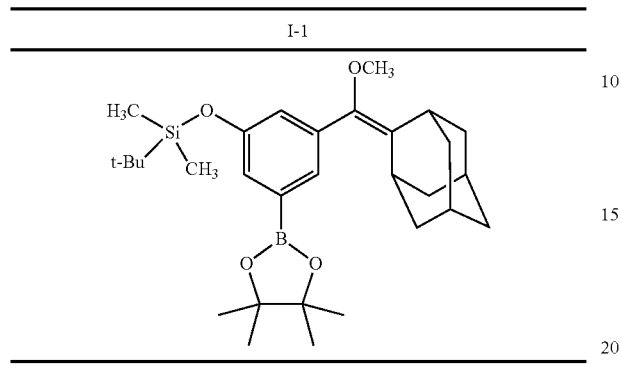

I-1

In another aspect, the invention provides a compound of the formula IIa or IIb:

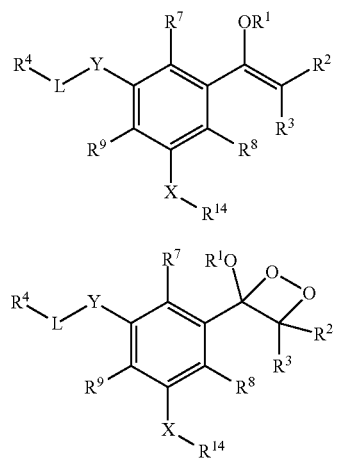

wherein $R^1$ is selected from a linear or branched $(C_1-C_{18})$alkyl, or $(C_3-C_7)$cycloalkyl;

$R^2$ and $R^3$ each independently is selected from a branched $(C_3-C_{18})$alkyl or $(C_3-C_7)$cycloalkyl, or $R^2$ and $R^3$ together with the carbon atom to which they are attached form a fused, spiro or bridged cyclic or polycyclic ring;

$R^4$ is a protecting group, such as those shown in Table 1 below;

Pep is a peptide moiety consisting of at least two amino acid residues and linked via a carboxylic group thereof;

L is absent or is a linker of the formula L1, L2 or L3, optionally substituted at the aromatic ring with one or more substituents each independently selected from $(C_1-C_{18})$alkyl or $(C_3-C_7)$cycloalkyl, wherein M is absent or is —O— or —NH—, and the asterisk represents the point of attachment to the group Y, provided that M is —O— or —NH— unless $R_4$ is 4,4,5,5-tetramethyl-1,3,2-dioxaborolanyl or —B(OH)$_2$;

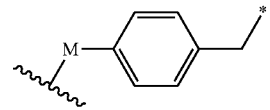

L1

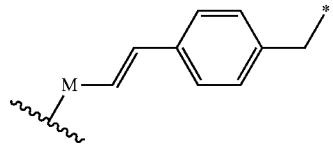

L2

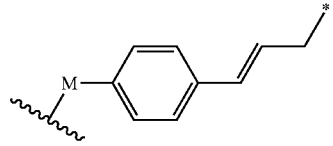

L3

Y is absent or is —O—, provided that Y is —O— unless $R^4$ is 4,4,5,5-tetramethyl-1,3,2-dioxaborolanyl or —B(OH)$_2$, and L is absent;

$R^7$, $R^8$ and $R^9$ each independently is H, or an electron acceptor group such as halogen, —NO$_2$, —CN, —COOR$^{10}$, —C(=O)R$^{10}$ and —SO$_2$R$^{10}$;

$R^{10}$ each independently is H or —$(C_1-C_{18})$alkyl;

X is a linker of the formula —X$_1$—X$_2$—, wherein X$_1$ is selected from $(C_1-C_{18})$alkylene, $(C_2-C_{18})$alkenylene, $(C_2-C_{18})$alkynylene, $(C_3-C_7)$cycloalkylene, $(C_3-C_7)$cycloalkenylene, $(C_6-C_{14})$arylene-diyl, $(C_1-C_{18})$alkylene-$(C_6-C_{14})$arylene-diyl, heteroarylenediyl, or $(C_1-C_{18})$alkylene-heteroarylenediyl, said $(C_1-C_{18})$alkylene, $(C_2-C_{18})$alkenylene, $(C_2-C_{18})$alkynylene, $(C_3-C_7)$cycloalkylene, $(C_3-C_7)$cycloalkenylene, $(C_6-C_{14})$arylene-diyl, or heteroarylenediyl being optionally substituted by one or more groups each independently selected from halogen, —COR$^{10}$, —COOR$^{10}$, —OCOOR$^{10}$, —OCON(R$^{10}$)$_2$ —CN, —NO$_2$, —SR$^{10}$, —OR$^{10}$, —N(R$^{10}$)$_2$, —CON(R$^{10}$)$_2$, —SO$_2$R, —SO$_3$H, —S(=O)R, $(C_6-C_{10})$aryl, $(C_1-C_4)$alkylene-$(C_6-C_{10})$aryl, heteroaryl, or $(C_1-C_4)$alkylene-heteroaryl, and said $(C_1-C_{18})$alkylene, $(C_2-C_{18})$alkenylene, or $(C_2-C_{18})$alkynylene being further optionally interrupted by one or more identical or different heteroatoms selected from S, O or N, and/or at least one group each independently selected from —NH—CO—, —CO—NH—, —N(C$_1$-C$_8$alkyl)-, —N(C$_6$-C$_{10}$aryl)-, $(C_6-C_{10})$arylene-diyl, or heteroarylenediyl; and X$_2$ is absent or is —C(O)—; and $R^{14}$ is a reactive group such as —O—$(C_1-C_{18})$alkyl, —N$_3$, —CCH, N-succinimidyloxy, 3-sulfo-N-succinimidyloxy, pentafluorophenyloxy, 4-nitrophenyloxy, N-imidazolyl, and N-1H-benzo[di][1,2,3]triazoloxy.

TABLE 1

Certain protecting/caging groups with respect to the compounds of the formulas IIa/IIb, IIIa/IIIb and IVa/IVb TBDMS; 2,4-dinitrobenzene sulfonate; 3,4,6-trimethyl-2,5-dioxobenzyl 4-azidobenzyloxy carbonyl; 4,4,5,5-tetramethyl-1,3,2-dioxaborolanyl 4-[4,4,5,5-tetramethyl-1,3,2-dioxaborolanyl]benzyl; —B(OH)$_2$; phosphonate galactosyl; glucosyl; glucuronyl The term "protecting group" as used herein with respect to the compound of the formula IIa/IIb refers to an alcohol protecting group as defined with respect to the compound of the formula I, as well as to certain cleavable groups including enzyme cleavable groups such as monosaccharide moieties linked through a carbon atom thereof. This protecting group is further referred to herein, with respect to the compounds of the formula IIIa/IIIb and IVa/IVb, as a "caging group". Particular protecting/caging groups are those shown in Table 1.

The term "reactive group" as used herein with respect to the compound of the formula IIa/IIb refers to any group capable of reacting with a functional group (i e, amine, carboxylic acid, sulfhydryl, hydroxyl, or aldehyde group) of a fluorophore. Examples of such groups, without limiting, include —O—(C$_1$-C$_{18}$)alkyl, —N$_3$, —C≡CH, N-succinimidyloxy, 3-sulfo-N-succinimidyloxy, pentafluorophenyloxy, 4-nitrophenyloxy, N-imidazolyl, and N-1H-benzo[d][1,2,3]triazoloxy (see Table 2).

TABLE 2

Certain reactive groups with respect to the compound of the formula IIa/IIb

| N-succinimidyloxy | 3-sulfo-N-succinimidyloxy | pentafluorophenyloxy |
|---|---|---|
| (structure) | (structure) | (structure) |

| 4-nitrophenyloxy | N-imidazolyl | N-1H-benzo[d][1,2,3]triazoloxy |
|---|---|---|
| (structure) | (structure) | (structure) |

In certain embodiments, the invention provides a compound of the formula IIa or IIb, wherein $R^1$ is a linear or branched $(C_1-C_8)$alkyl, preferably $(C_1-C_4)$alkyl, more preferably methyl or ethyl.

In certain embodiments, the invention provides a compound of the formula IIa or IIb, wherein $R^2$ and $R^3$ each independently is a branched $(C_3-C_{18})$alkyl or $(C_3-C_7)$cycloalkyl. In other embodiments, $R^2$ and $R^3$ each independently is a branched $(C_3-C_{18})$alkyl or $(C_3-C_7)$cycloalkyl, and together with the carbon atom to which they are attached form a fused, spiro or bridged polycyclic ring. In particular such embodiments, $R^2$ and $R^3$ together with the carbon atom to which they are attached form adamantyl.

In certain embodiments, the invention provides a compound of the formula IIa or IIb, wherein at least one (i.e., one, two or three) of $R^7$, $R^8$ and $R^9$ is H, and the other of $R^7$, $R^8$ and $R^9$ each independently is an electron acceptor group as defined above. In certain particular such embodiments, $R^7$, $R^8$ and $R^9$ each is H. In other particular such embodiments, $R^7$ is an electron acceptor group as defined above, and $R^8$ and $R^9$ each is H; or $R^8$ is an electron acceptor group as defined above, and $R^7$ and $R^9$ each is H; or $R^9$ is an electron acceptor group as defined above, and $R^7$ and $R^8$ each is H, wherein said electron acceptor group is particularly halogen, —NO$_2$ or —CN.

In certain embodiments, the invention provides a compound of the formula IIa or IIb, wherein $X_1$ is $(C_1-C_{18})$alkylene, $(C_6-C_{14})$arylene-diyl, or $(C_1-C_{18})$alkylene-$(C_6-C_{14})$arylene-diyl, optionally substituted by one or more groups each independently selected from halogen, COR$^{10}$, —COOR$^{10}$, —OCOOR$^{10}$, —OCON(R$^{10}$)$_2$, CN, —NO$_2$, SR$^{10}$, —OR$^{10}$, —N(R$^{10}$)$_2$, —CON(R$^{10}$)$_2$, —SO$_2$R$^{10}$, —SO$_3$H, —S(=O)R$^{10}$, $(C_6-C_{10})$aryl, $(C_1-C_4)$alkylene-$(C_6-C_{10})$aryl, heteroaryl, or $(C_1-C_4)$alkylene-heteroaryl, wherein R$^{10}$ is H, and said $(C_1-C_{18})$alkylene being further optionally interrupted by one or more identical or different heteroatoms selected from S, O or N, and/or at least one group each independently selected from —NH—CO—, —CO—NH—, —N(C$_1$-C$_8$alkyl)-, —N(C$_6$-C$_{10}$aryl)-, (C$_6$-C$_{10}$)arylene-diyl, or heteroarylenediyl; and X$_2$ is —C(O)—. In particular such embodiments, $X_1$ is $(C_6-C_{14})$arylene-diyl or $(C_1-C_4)$alkylene-$(C_6-C_{14})$arylene-diyl, wherein said $(C_6-C_{14})$arylene-diyl is, e.g., phenylene, naphthylene, phenanthrylene, or biphenylene; and $X_2$ is —C(O)— linked to any carbon atom of the arylene-diyl. In specific embodiments, X is the linker:

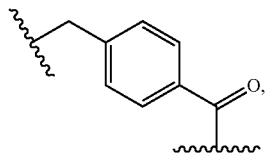 [SMILES: *Cc1ccc(C(*)=O)cc1]

i.e., $X_1$ is —(CH$_2$)-para-phenylene and $X_2$ is —C(O)—.

In certain embodiments, the invention provides a compound of the formula IIa or IIb, wherein $R^{14}$ is N-succinimidyloxy, or 3-sulfo-N-succinimidyloxy.

In certain embodiments, the invention provides a compound of the formula IIa or IIb, wherein $R^1$ is a linear or branched $(C_1-C_8)$alkyl, preferably $(C_1-C_4)$alkyl, more preferably methyl or ethyl; $R^2$ and $R^3$ each independently is selected from a branched $(C_3-C_{18})$alkyl or $(C_3-C_7)$cycloalkyl, and together with the carbon atom to which they are attached form a fused, spiro or bridged polycyclic ring; at least one of $R^7$, $R^8$ and $R^9$ is H, and the other of $R^7$, $R^8$ and $R^9$ each independently is an electron acceptor group selected from halogen, —NO$_2$ or —CN; X is a linker of the formula —X$_1$—X$_2$—, wherein X$_1$ is $(C_1-C_{18})$alkylene, $(C_6-C_{14})$arylene-diyl, or $(C_1-C_{18})$alkylene-$(C_6-C_{14})$arylene-diyl, optionally substituted by one or more groups each independently selected from halogen, —COH, —COOH, —OCOOH, —OCONH$_2$, —CN, —NO$_2$, —SH, —OH, —NH$_2$, —CONH$_2$, —SO$_2$H, —SO$_3$H, —S(=O)H, $(C_6-C_{10})$aryl, $(C_1-C_4)$alkylene-$(C_6-C_{10})$aryl, heteroaryl, or $(C_1-C_4)$alkylene-heteroaryl, and said $(C_1-C_{18})$alkylene being further optionally interrupted by one or more identical or different heteroatoms selected from S, O or N, and/or at least one group each independently selected from —NH—CO—, —CO—NH—, —N(C$_1$-C$_8$alkyl)-, —N(C$_6$-C$_{10}$aryl)-, (C$_6$-C$_{10}$)arylene-diyl, or heteroarylenediyl; and $X_2$ is —C(O)—; and $R^{14}$ is N-succinimidyloxy, or 3-sulfo-N-succinimidyloxy.

In particular such embodiments, $R^2$ and $R^3$ together with the carbon atom to which they are attached form adamantyl;

or X is a linker of the formula —X$_1$—X$_2$—, wherein X$_1$ is (C$_6$-C$_{14}$)arylene-diyl or (C$_1$-C$_4$)alkylene-(C$_6$-C$_{14}$)arylene-diyl, wherein said (C$_6$-C$_{14}$)arylene-diyl is phenylene, naphthylene, phenanthrylene, or biphenylene; and X$_2$ is —C(O)— linked to any carbon atom of the arylene-diyl. In more particular such embodiments, R$^2$ and R$^3$ together with the carbon atom to which they are attached form adamantyl; and/or X$_1$ is —(CH$_2$)-para-phenylene and X$_2$ is —C(O)—. Specific examples of such embodiments are those wherein R$^1$ is methyl; R$^2$ and R$^3$ together with the carbon atom to which they are attached form adamantyl; X$_1$ is —(CH$_2$)-para-phenylene; and X$_2$ is —C(O)—, e.g., such compounds wherein at least one of R$^7$, R$^8$ and R$^9$ is H, and the other of R$^7$, R$^8$ and R$^9$ each independently is a halogen.

In certain embodiments, the invention provides a compound of the formula IIa or IIb as defined in any one of the embodiments above, wherein (i) Y is —O—, L is absent or a linker of the formula L1, L2 or L3, wherein M is —O— or —NH—, and R$^4$ is a protecting group; or (ii) Y is absent, L is absent, and R$^4$ is 4,4,5,5-tetramethyl-1,3,2-dioxaborolanyl or —B(OH)$_2$.

In specific such embodiments, R$^1$ is methyl; R$^2$ and R$^3$ together with the carbon atom to which they are attached form adamantyl; R$^7$, R$^8$ and R$^9$ are H; Y is —O—; L is absent; R$^4$ is TBDMS; X$_1$ is —(CH$_2$)-para-phenylene; X$_2$ is —C(O)—; and R$^{14}$ is N-succinimidyloxy (compounds IIa-1 and IIb-1, Table 3).

TABLE 3

Specific compounds of the formula IIa/IIb described herein

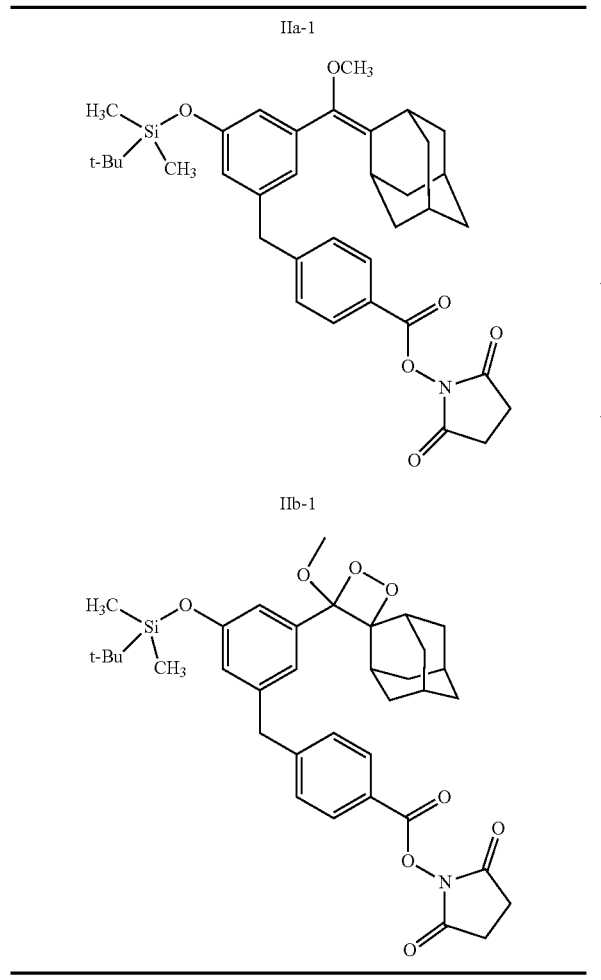

In still another aspect, the present invention provides a conjugate of the formula IIIa or IIIb:

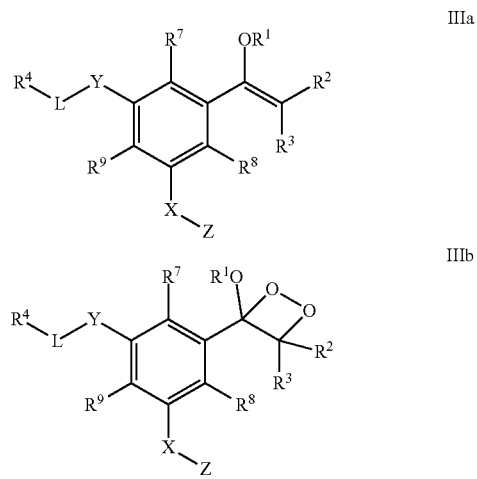

wherein
R$^1$ is selected from a linear or branched (C$_1$-C$_{18}$)alkyl, or (C$_3$-C$_7$)cycloalkyl;
R$^2$ and R$^3$ each independently is selected from a branched (C$_3$-C$_{18}$)alkyl or (C$_3$-C$_7$)cycloalkyl, or R$^2$ and R$^3$ together with the carbon atom to which they are attached form a fused, spiro or bridged cyclic or polycyclic ring;
R$^4$ is a caging group, such as those shown in Table 1;
Pep is a peptide moiety consisting of at least two amino acid residues and linked via a carboxylic group thereof;
L is absent or is a linker of the formula L1, L2 or L3, optionally substituted at the aromatic ring with one or more substituents each independently selected from (C$_1$-C$_{18}$)alkyl or (C$_3$-C$_7$)cycloalkyl, wherein M is absent or is —O— or —NH—, and the asterisk represents the point of attachment to the group Y, provided that M is —O— or —NH— unless R$_4$ is 4,4,5,5-tetramethyl-1,3,2-dioxaborolanyl or —B(OH)$_2$;

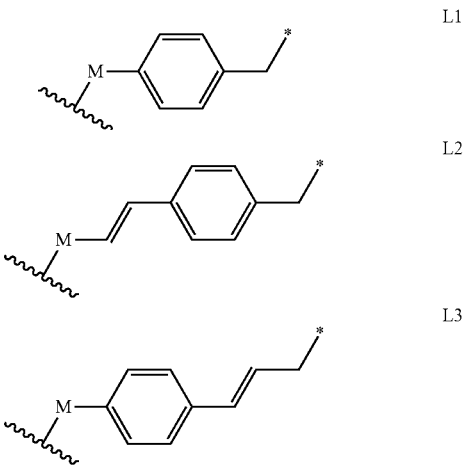

Y is absent or is —O—, provided that Y is —O— unless R$_4$ is 4,4,5,5-tetramethyl-1,3,2-dioxaborolanyl or —B(OH)$_2$, and L is absent;

R⁷, R⁸ and R⁹ each independently is H, or an electron acceptor group such as halogen, —NO₂, —CN, —COOR¹⁰, —CH(=O), —C(=O)R¹⁰ and —SO₂R¹°;

R¹⁰ each independently is H or —(C₁-C₁₈)alkyl;

X is a linker of the formula —X₁—X₂—, wherein X₁ is selected from (C₁-C₁₈)alkylene, (C₂-C₁₈)alkenylene, (C₂-C₁₈)alkynylene, (C₃-C₇)cycloalkylene, (C₃-C₇)cycloalkenylene, (C₆-C₁₄)arylene-diyl, (C₁-C₁₈)alkylene-(C₆-C₁₄)arylene-diyl, heteroarylenediyl, or (C₁-C₁₈)alkylene-heteroarylenediyl, said (C₁-C₁₈)alkylene, (C₂-C18)alkenylene, (C₂-C₁₈)alkynylene, (C₃-C₇)cycloalkylene, (C₃-C₇)cycloalkenylene, (C₆-C₁₄)arylene-diyl, or heteroarylenediyl being optionally substituted by one or more groups each independently selected from halogen, —COR¹⁰, —COOR¹⁰, —OCOOR¹⁰, —OCON(R¹⁰)₂ —CN, NO₂, SR¹⁰, OR¹⁰, N(R¹⁰)₂, CON(R¹⁰)₂, —SO₂R¹⁰, —SO₃H, —S(=O)R¹⁰, (C₆-C₁₀)aryl, (C₁-C₄)alkylene-(C₆-C₁₀)aryl, heteroaryl, or (C₁-C₄)alkylene-heteroaryl, and said (C₁-C₁₈)alkylene, (C₂-C₁₈)alkenylene, or (C₂-C₁₈)alkynylene being further optionally interrupted by one or more identical or different heteroatoms selected from S, O or N, and/or at least one group each independently selected from —NH—CO—, —CO—NH—, —N(C₁-C₈alkyl)-, —N(C₆-C₁₀aryl)-, (C₆-C₁₀)arylene-diyl, or heteroarylenediyl; and X₂ is absent or is —C(O)—; and Z is a moiety of a fluorophore or a derivative thereof.

The term "fluorophore" as used herein refers to a fluorescent chemical compound, typically containing several combined aromatic groups, or plane or cyclic molecules having several 7E bonds, which can re-emit light upon light excitation. Non-limiting categories of fluorophores include fluorescein-based compounds (fluorescein analogues), rhodamine-based compounds (rhodamine analogues), coumarin-based compounds (coumarin analogues), cyanines such as Cy5, Cy5.5, Cy5.18, Cy7, Cy7.18, and QCy, and boron-dipyrromethene (BODIPY)-based compounds.

In certain embodiments, the invention provides a conjugate of the formula IIIa or IIIb, wherein R¹ is a linear or branched (C₁-C₈)alkyl, preferably (C₁-C₄)alkyl, more preferably methyl or ethyl.

In certain embodiments, the invention provides a conjugate of the formula IIIa or Mb, wherein R² and R³ each independently is a branched (C₃-C₁₈)alkyl or (C₃-C₇)cycloalkyl. In other embodiments, R² and R³ each independently is a branched (C₃-C₁₈)alkyl or (C₃-C₇)cycloalkyl, and together with the carbon atom to which they are attached form a fused, spiro or bridged polycyclic ring. In particular such embodiments, R² and R³ together with the carbon atom to which they are attached form adamantyl.

In certain embodiments, the invention provides a conjugate of the formula IIIa or Mb, wherein at least one (i.e., one, two or three) of R⁷, R⁸ and R⁹ is H, and the other of R⁷, R⁸ and R⁹ each independently is an electron acceptor group as defined above. In certain particular such embodiments, R⁷, R⁸ and R⁹ each is H. In other particular such embodiments, R⁷ is an electron acceptor group as defined above, and R⁸ and R⁹ each is H; or R⁸ is an electron acceptor group as defined above, and R⁷ and R⁹ each is H; or R⁹ is an electron acceptor group as defined above, and R⁷ and R⁸ each is H, wherein said electron acceptor group is particularly halogen, —NO₂ or —CN.

In certain embodiments, the invention provides a conjugate of the formula IIIa or IIIb, wherein X₁ is (C₁-C₁₈)alkylene, (C₆-C₁₄)arylene-diyl, or (C₁-C₁₈)alkylene-(C₆-C₁₄)arylene-diyl, optionally substituted by one or more groups each independently selected from halogen, COR¹⁰, COOR¹⁰, OCOOR¹⁰, OCON(R¹⁰)₂, —CN, —NO₂, —SR¹⁰, —OR¹⁰, N(R¹⁰)₂, —CON(R¹⁰)₂, —SO₂R¹⁰, —SO₃H, —S(=O)R¹⁰, (C₆-C₁₀)aryl, (C₁-C₄)alkylene-(C₆-C₁₀)aryl, heteroaryl, or (C₁-C₄)alkylene-heteroaryl, wherein R¹⁰ is H, and said (C₁-C₁₈)alkylene being further optionally interrupted by one or more identical or different heteroatoms selected from S, O or N, and/or at least one group each independently selected from —NH—CO—, —CO—NH—, —N(C₁-C₈alkyl)-, —N(C₆-C₁₀)aryl)-, (C₆-C₁₀)arylene-diyl, or heteroarylenediyl; and X₂ is —C(O)—. In particular such embodiments, X₁ is (C₆-C₁₄)arylene-diyl or (C₁-C₄)alkylene-(C₆-C₁₄)arylene-diyl, wherein said (C₆-C₁₄)arylene-diyl is, e.g., phenylene, naphthylene, phenanthrylene, or biphenylene; and X₂ is —C(O)— linked to any carbon atom of the arylene-diyl. In specific embodiments, X₁ is —(CH₂)-para-phenylene and X₂ is —C(O)—.

In certain embodiments, the invention provides a conjugate of the formula IIIa or IIIb, wherein the fluorophore Z is selected from the BODIPY derivative identified herein as Z1, the fluorescein derivative identified herein as Z2, the Cy5 derivative identified herein as Z3, or the QCy derivative identified herein as Z4 (Table 4).

In certain embodiments, the invention provides a conjugate of the formula IIIa or IIIb, wherein R¹ is a linear or branched (C₁-C₈)alkyl, preferably (C₁-C₄)alkyl, more preferably methyl or ethyl; R² and R³ each independently is selected from a branched (C₃-C₁₈)alkyl or (C₃-C₇)cycloalkyl, and together with the carbon atom to which they are attached form a fused, spiro or bridged polycyclic ring; at least one of R⁷, R⁸ and R⁹ is H, and the other of R⁷, R⁸ and R⁹ each independently is an electron acceptor group selected from halogen, —NO₂ or —CN; X is a linker of the formula —X₁—X₂—, wherein X₁ is (C₁-C₁₈)alkylene, (C₆-C₁₄)arylene-diyl, or (C₁-C₁₈)alkylene-(C₆-C₁₄)arylene-diyl, optionally substituted by one or more groups each independently selected from halogen, —COH, —COOH, —OCOOH, —OCONH₂, —CN, —NO₂, —SH, —OH, —NH₂, —CONH₂, —SO₂H, —SO₃H, —S(=O)H, (C₆-C₁₀)aryl, (C₁-C₄)alkylene-(C₆-C₁₀)aryl, heteroaryl, or (C₁-C₄)alkylene-heteroaryl, and said (C₁-C₁₈)alkylene being further optionally interrupted by one or more identical or different heteroatoms selected from S, O or N, and/or at least one group each independently selected from —NH—CO—, —CO—NH—, —N(C₁-C₈alkyl)-, —N(C₆-C₁₀aryl)-, (C₆-C₁₀)arylene-diyl, or heteroarylenediyl; and X₂ is —C(O)—.

TABLE 4

Fluorophore moieties identified herein as Z1-Z4

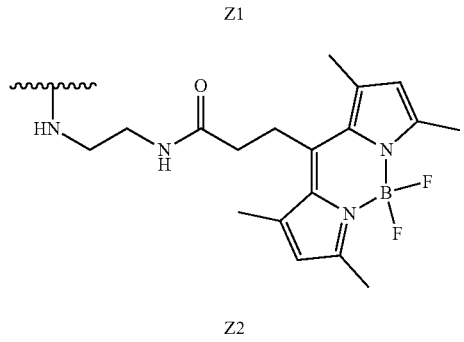

Z1

Z2

TABLE 4-continued

Fluorophore moieties identified herein as Z1-Z4

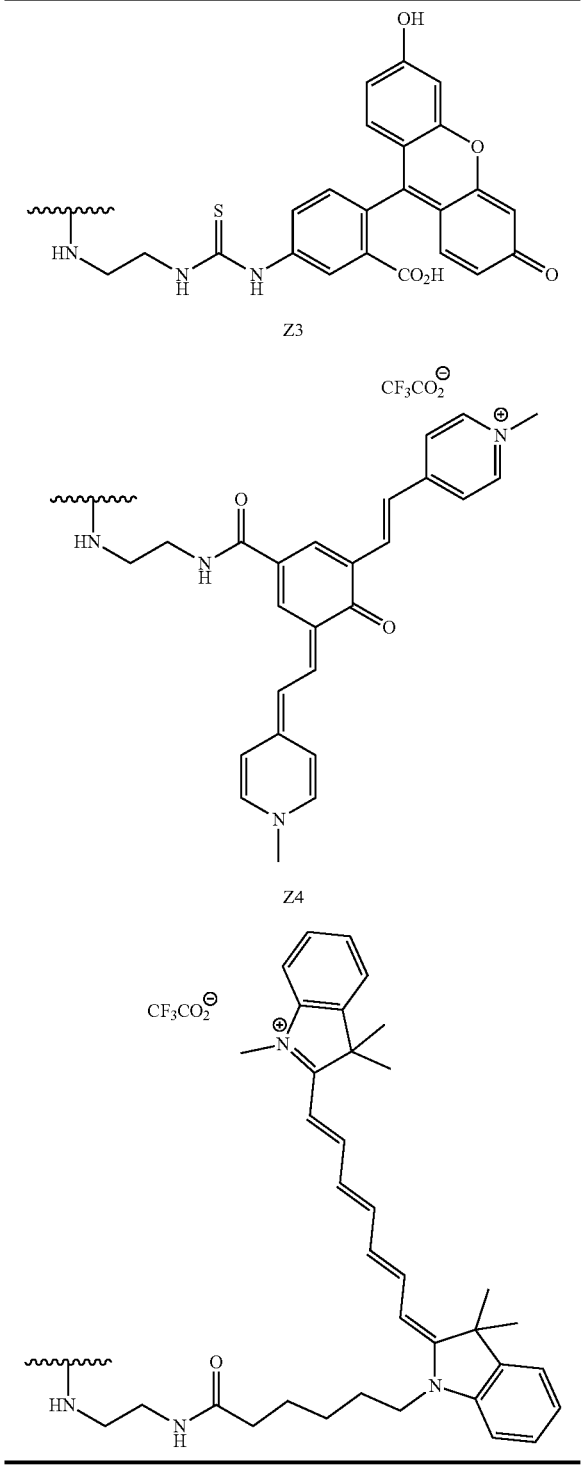

the carbon atom to which they are attached form adamantyl; and/or $X_1$ is —($CH_2$)-para-phenylene and $X_2$ is —C(O)—. Specific examples of such embodiments are those wherein $R^1$ is methyl; $R^2$ and $R^3$ together with the carbon atom to which they are attached form adamantyl; $X_1$ is —($CH_2$)-para-phenylene; and $X_2$ is —C(O)—, e.g., such compounds wherein at least one of $R^7$, $R^8$ and $R^9$ is H, and the other of $R^7$, $R^8$ and $R^9$ each independently is a halogen.

TABLE 5

Specific conjugates of the formula IIIa/IIIb described herein

IIIa-1-4 (Z = Z1 to Z4)

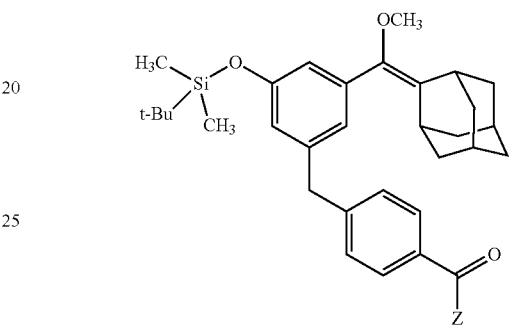

IIIb-1-4 (Z = Z1 to Z4)

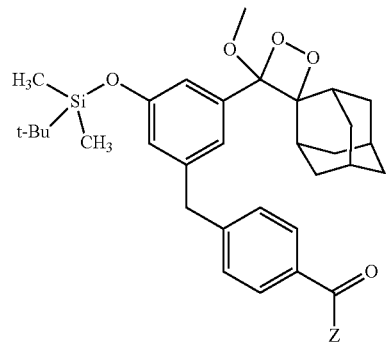

IIIa-5-8 (Z = Z1 to Z4)

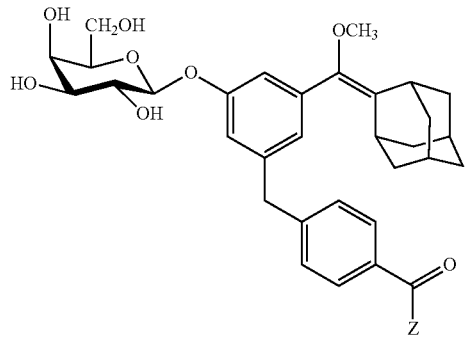

IIIb-5-8 (Z = Z1 to Z4)

In particular such embodiments, $R^2$ and $R^3$ together with the carbon atom to which they are attached form adamantyl; or X is a linker of the formula —$X_1$—$X_2$—, wherein $X_1$ is ($C_6$-$C_{14}$)arylene-diyl or ($C_1$-$C_4$)alkylene-($C_6$-$C_{14}$)arylene-diyl, wherein said ($C_6$-$C_{14}$)arylene-diyl is phenylene, naphthylene, phenanthrylene, or biphenylene; and $X_2$ is —C(O)— linked to any carbon atom of the arylene-diyl. In more particular such embodiments, $R^2$ and $R^3$ together with TABLE 5-continued Specific conjugates of the formula IIIa/IIIb described herein

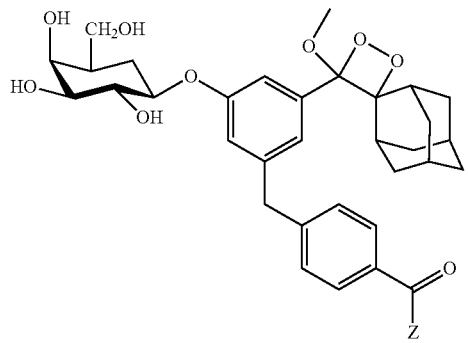

In certain embodiments, the invention provides a compound of the formula IIIa or IIIb as defined in any one of the embodiments above, wherein (i) Y is —O—, L is absent or a linker of the formula L1, L2 or L3, wherein M is —O— or —NH—, and $R^4$ is a caging group; or (ii) Y is absent, L is absent, and $R^4$ is 4,4,5,5-tetramethyl-1,3,2-dioxaborolanyl or —B(OH)$_2$.

In specific such embodiments, $R^1$ is methyl; $R^2$ and $R^3$ together with the carbon atom to which they are attached form adamantyl; $X_1$ is —(CH$_2$)-para-phenylene; $X_2$ is —C(O)—; Z is selected from groups Z1, Z2, Z3 or Z4; and (i) $R^7$, $R^8$ and $R^9$ are H; Y is —O—; L is absent; and $R^4$ is TBDMS (compounds IIIa-1-4 wherein Z is Z1-Z4, respectively; and IIIb-1-4 wherein Z is Z1-Z4, respectively); or (ii) $R^7$ is $C_1$; $R^8$ and $R^9$ are H; Y is —O—; L is absent; and $R^4$ is galactosyl (compounds IIIa-5-8 wherein Z is Z1-Z4, respectively; and IIIb-5-8 wherein Z is Z1-Z4, respectively). The specific compounds disclosed herein are shown in Table 5. Compounds IIIb-6 and IIIb-7, wherein Z is Z2 or Z3 respectively, are also referred to in Study 1 herein as Probes 2 and 3, respectively.

In yet another aspect, the present invention provides a compound of the formula IVa or IVb:

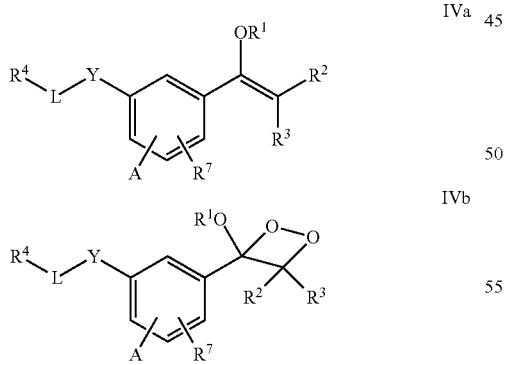

wherein $R^1$ is selected from a linear or branched (C$_1$-C$_{18}$)alkyl, or (C$_3$-C$_7$)cycloalkyl;

$R^2$ and $R^3$ each independently is selected from a branched (C$_3$-C$_{18}$)alkyl or (C$_3$-C$_7$)cycloalkyl, or $R^2$ and $R^3$ together with the carbon atom to which they are attached form a fused, spiro or bridged cyclic or polycyclic ring;

$R^4$ is H, or a caging group such as those shown in Table 1;

Pep is a peptide moiety consisting of at least two amino acid residues and linked via a carboxylic group thereof;

L is absent or is a linker of the formula L1, L2 or L3, optionally substituted at the aromatic ring with one or more substituents each independently selected from (C$_1$-C$_{18}$)alkyl or (C$_3$-C$_7$)cycloalkyl, wherein M is absent or is —O— or —NH—, and the asterisk represents the point of attachment to the group Y, provided that M is —O— or —NH— unless $R^4$ is 4,4,5,5-tetramethyl-1,3,2-dioxaborolanyl or —B(OH)$_2$, and when $R^4$ is H, L is absent;

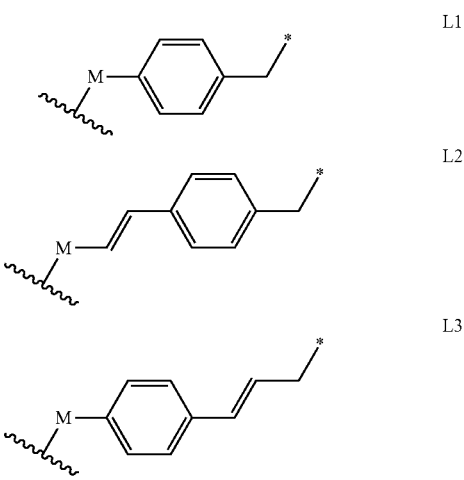

Y is absent or is —O—, provided that Y is —O— unless $R^4$ is 4,4,5,5-tetramethyl-1,3,2-dioxaborolanyl or —B(OH)$_2$, and L is absent;

$R^7$ is H, or represents at least one electron acceptor group such as halogen, —NO$_2$, —CN, —COOR$^{10}$, —C(=O)R$^{10}$ and —SO$_2$R$^{10}$, each independently attached either ortho or para to the —Y-L-R$^4$ group;

$R^{10}$ each independently is H or —(C$_1$-C$_{18}$)alkyl; and

A is a π* acceptor group such as —CN, or —CH=CH-E, attached either ortho or para to the —Y-L-R$^4$ group, wherein E is —CN, —COOH, —COO(C$_1$-C$_{18}$)alkyl such as —COO(C$_1$-C$_8$)alkyl or —COO(C$_1$-C$_4$)alkyl, 4-pyridinyl, methylpyridinium-4-yl, 3,3-dimethyl-3H-indolyl, or 1,3,3-dimethyl-3H-indol-1-ium-2-yl.

TABLE 6

Certain π* acceptor groups with respect to compounds of the formula IVa or IVb 4-pyridinyl

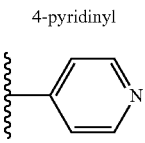

methylpyridinium-4-yl

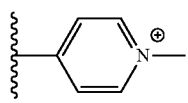

TABLE 6-continued

Certain π* acceptor groups with respect to compounds of the formula IVa or IVb 3,3-dimethyl-3H-indolyl

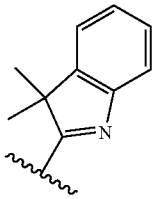 [SMILES: *C1=Nc2ccccc2C1(C)C]

1,3,3-trimethyl-3H-indol-1-ium-2-yl

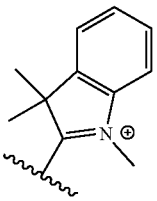 [SMILES: *C1=[N+](C)c2ccccc2C1(C)C]

The term "π* acceptor group" as used herein refers to any group containing a 7E acceptor system capable of accepting electrons.

In certain embodiments, the invention provides a compound of the formula IVa or IVb, wherein $R^1$ is a linear or branched $(C_1-C_8)$alkyl, preferably $(C_1-C_4)$alkyl, more preferably methyl or ethyl.

In certain embodiments, the invention provides a compound of the formula IVa or IVb, wherein $R^2$ and $R^3$ each independently is a branched $(C_3-C_{18})$alkyl or $(C_3-C_7)$cycloalkyl. In other embodiments, $R^2$ and $R^3$ each independently is a branched $(C_3-C_{18})$alkyl or $(C_3-C_7)$cycloalkyl, and together with the carbon atom to which they are attached form a fused, spiro or bridged polycyclic ring. In a particular such embodiment, $R^2$ and $R^3$ together with the carbon atom to which they are attached form adamantyl.

In certain embodiments, the invention provides a compound of the formula IVa or IVb, wherein $R^7$ is H, or an electron acceptor group selected from halogen or —CN attached either ortho or para to the —Y-L-$R^4$ group. In particular such embodiments, $R^7$ is halogen, e.g., $C_1$, or —CN, attached ortho to the —Y-L-$R^4$ group.

In certain embodiments, the invention provides a compound of the formula IVa or IVb, wherein A is —CH=CH-E attached ortho to the —Y-L-$R^4$ group, wherein E is —CN, —COOH, —COO($C_1$-$C_8$)alkyl, e.g., —COO($C_1$-$C_4$)alkyl such as —COOCH$_3$, —COOC$_2$H$_5$, —COOC$_3$H$_7$, —COOCH(CH$_3$)$_2$, or —COOC(CH$_3$)$_3$, 4-pyridinyl, methylpyridinium-4-yl, 3,3-dimethyl-3H-indolyl, or 1,3,3-trimethyl-3H-indol-1-ium-2-yl. In particular such embodiments, E is —CN, —COOH, —COOCH$_3$, —COOC$_2$H$_5$, —COOC$_3$H$_7$, —COOCH(CH$_3$)$_2$, or —COOC(CH$_3$)$_3$.

In certain embodiments, the invention provides a compound of the formula IVa or IVb, wherein $R^1$ is a linear or branched $(C_1-C_8)$alkyl, preferably $(C_1-C_4)$alkyl, more preferably methyl or ethyl; $R^2$ and $R^3$ each independently is selected from a branched $(C_3-C_{18})$alkyl or $(C_3-C_7)$cycloalkyl, and together with the carbon atom to which they are attached form a fused, spiro or bridged polycyclic ring; $R^7$ is H, or an electron acceptor group selected from halogen or —CN, attached either ortho or para to the —Y-L-$R^4$ group; and A is —CH=CH-E attached ortho to the —Y-L-$R^4$ group, wherein E is —CN, —COOH, —COO($C_1$-$C_5$)alkyl, 4-pyridinyl, methylpyridinium-4-yl, 3,3-dimethyl-3H-indolyl, or 1,3,3-trimethyl-3H-indol-1-ium-2-yl. Particular such embodiments are those wherein $R^1$ is methyl; $R^2$ and $R^3$ together with the carbon atom to which they are attached form adamantyl; $R^7$ is H, or is an electron acceptor group selected from halogen or —CN, attached ortho to the —Y-L-$R^4$ group; and E is —CN, —COOH, or —COO($C_1$-$C_4$)alkyl such as —COOCH$_3$, —COOC$_2$H$_5$, —COOC$_3$H$_7$, —COOCH(CH$_3$)$_2$, or —COOC(CH$_3$)$_3$. More particular such embodiments are those wherein E is —CN, —COOH, —COOCH$_3$, or —COOC(CH$_3$)$_3$, i.e., A is acrylonitrile, acrylic acid, methylacrylate or tert-butyl acrylate substituent, respectively, attached ortho to the —Y-L-$R^4$ group.

In certain embodiments, the invention provides a compound of the formula IVa or IVb as defined in any one of the embodiments above, wherein (i) Y is —O—; L is absent; and $R^4$ is H; (ii) Y is —O—; L is either absent or a linker of the formula L1, L2 or L3 as defined above, wherein M is —O— or —NH—; and $R^4$ is a caging group such as those shown in Table 1, e.g., phosphonate, but provided that said caging group is not 4,4,5,5-tetramethyl-1,3,2-dioxaborolanyl or —B(OH)$_2$; (iii) Y is —O—; L is a linker of the formula L1, L2 or L3 as defined above, wherein M is absent; and $R^4$ is 4,4,5,5-tetramethyl-1,3,2-dioxaborolanyl or —B(OH)$_2$; or (iv) Y is absent; L is absent; and $R^4$ is 4,4,5,5-tetramethyl-1,3,2-dioxaborolanyl or —B(OH)$_2$.

In specific such embodiments, the compound disclosed herein is a compound of the formula IVa or IVb, wherein $R^1$ is methyl; $R^2$ and $R^3$ together with the carbon atom to which they are attached form adamantyl; $R^7$ is H, or $C_1$ attached ortho to the —Y-L-$R^4$ group; A is —CH=CH-E attached ortho to the —Y-L-$R^4$ group; and (i) E is —COOC(CH$_3$)$_3$; Y is —O—; L is absent; and $R^4$ is galactosyl (e.g., compounds IVa-1, IVa-2, IVb-1 and IVb-2); (ii) E is —COOCH$_3$ or —CN; Y is —O—; L is absent; and $R^4$ is H (e.g., compounds IVa-3, IVa-4, IVa-5, IVa-6, IVb-3, IVb-4, IVb-5 and IVb-6); (iii) E is —COOCH$_3$ or —CN; Y is —O—; L is L1 wherein M is —O—; and $R^4$ is galactosyl (e.g., compounds IVa-7, IVa-8, IVa-9, IVa-10, IVb-7, IVb-8, IVb-9 and IVb-10); (iv) E is —COOCH$_3$; Y is —O—; L is L1 wherein M is —NH; and $R^4$ is 2,4-dinitrobenzene sulfonate (e.g., compounds IVa-11, IVa-12, IVb-11 and IVb-12); (v) E is —COOH; Y is absent; L is absent; and $R^4$ is 4,4,5,5-tetramethyl-1,3,2-dioxaborolanyl (e.g., compounds IVa-13, IVa-14, IVb-13 and IVb-14); or (vi) E is —COOH; Y is —O—; L is absent; and $R^4$ is phosphonate (e.g., compounds IVa-15, IVa-16, IVb-15 and IVb-16). The specific compounds disclosed herein are shown in Table 7. Compounds IVb-7, IVb-8, IVb-9, IVb-10, IVb-13, IVb-15 and IVb-11 are also referred to in Study 2 herein as Probes 6, 7, 8, 9, 10, 11 and 12, respectively.

TABLE 7
Specific compounds of the formula IVa/IVb described herein
IVa-1 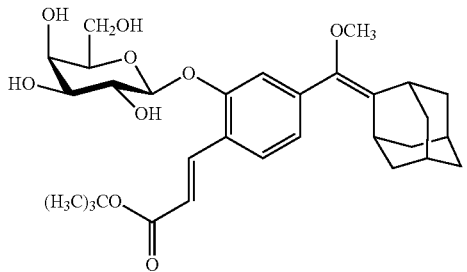 IVb-1 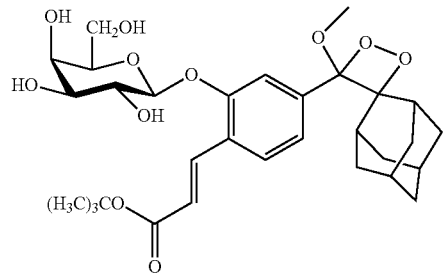
IVa-2 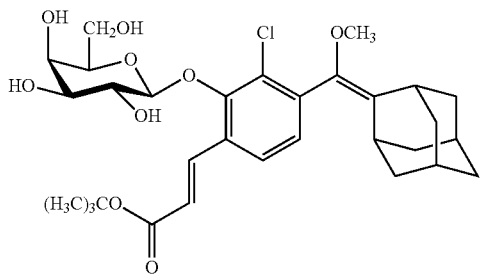 IVb-2 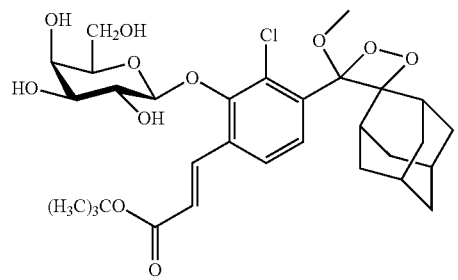
IVa-3 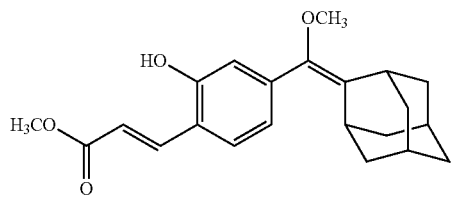 [SMILES: COC(=O)/C=C/c1ccc(C(OC)=C2C3CC4CC(C3)CC2C4)cc1O] IVb-3 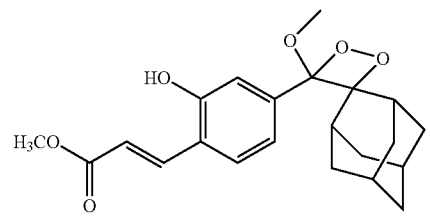 [SMILES: COC(=O)/C=C/c1ccc(C2(OC)OOC23C2CC4CC(C2)CC3C4)cc1O]
IVa-4 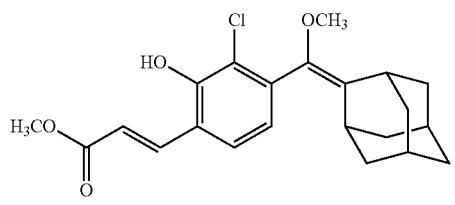 [SMILES: COC(=O)/C=C/c1ccc(C(OC)=C2C3CC4CC(C3)CC2C4)c(Cl)c1O] IVb-4 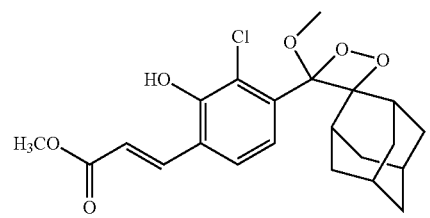 [SMILES: COC(=O)/C=C/c1ccc(C2(OC)OOC23C2CC4CC(C2)CC3C4)c(Cl)c1O]
IVa-5 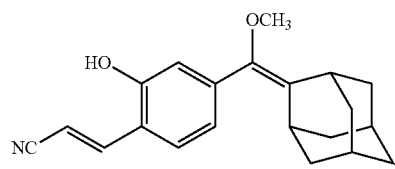 [SMILES: COC(=C1C2CC3CC(C2)CC1C3)c1ccc(/C=C/C#N)c(O)c1] IVb-5 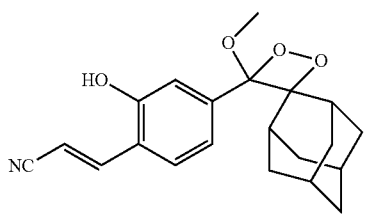 [SMILES: COC1(c2ccc(/C=C/C#N)c(O)c2)OOC12C1CC3CC(C1)CC2C3]
IVa-6 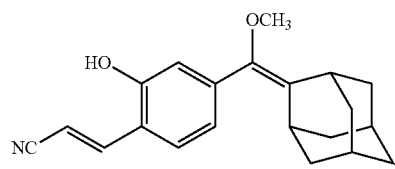 [SMILES: COC(=C1C2CC3CC(C2)CC1C3)c1ccc(/C=C/C#N)c(O)c1] IVb-6 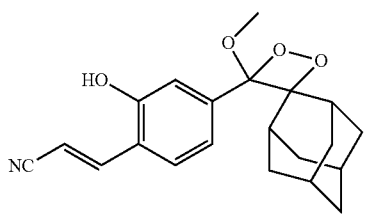 [SMILES: COC1(c2ccc(/C=C/C#N)c(O)c2)OOC12C1CC3CC(C1)CC2C3]

TABLE 7-continued
Specific compounds of the formula IVa/IVb described herein
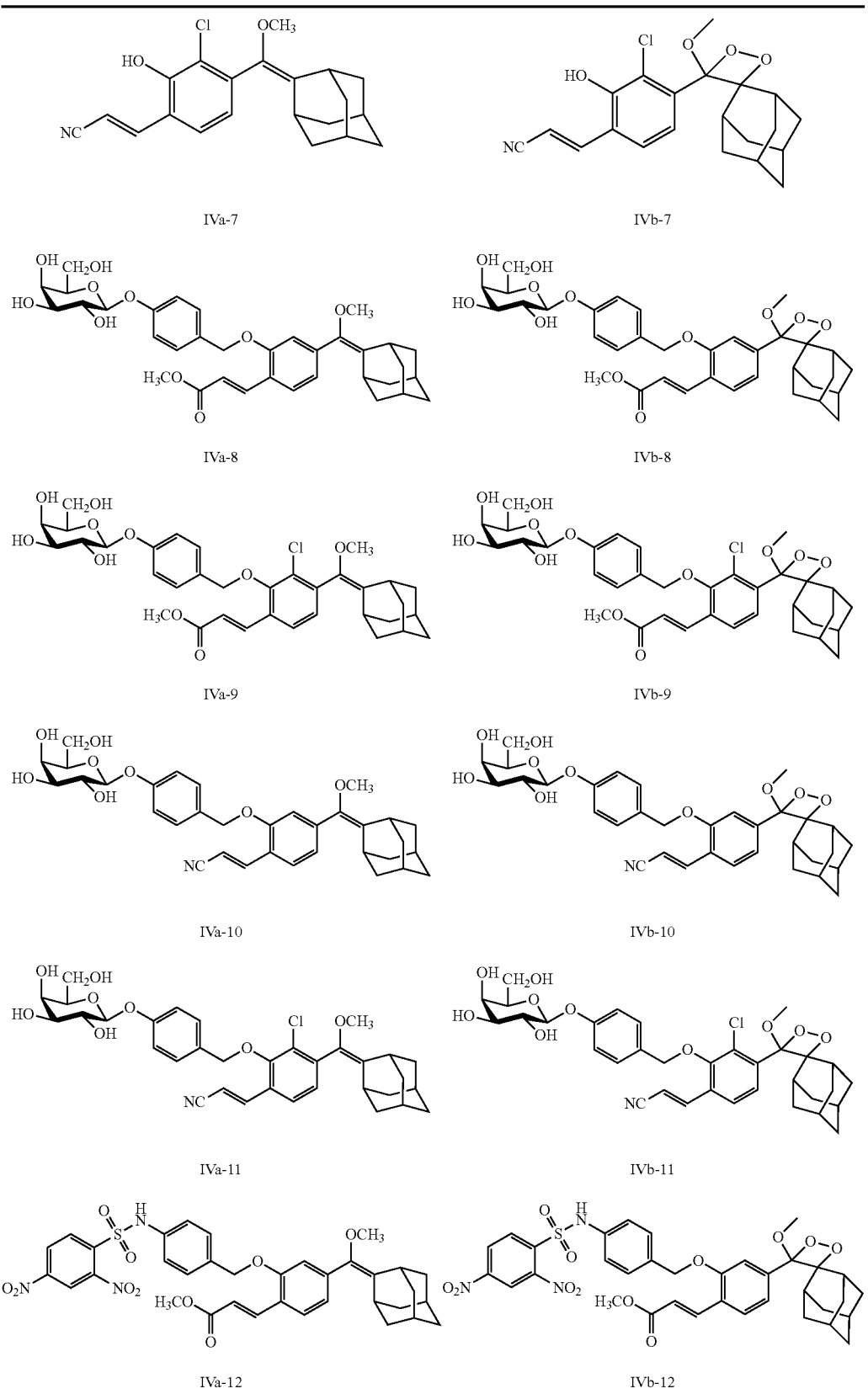

TABLE 7-continued

Specific compounds of the formula IVa/IVb described herein

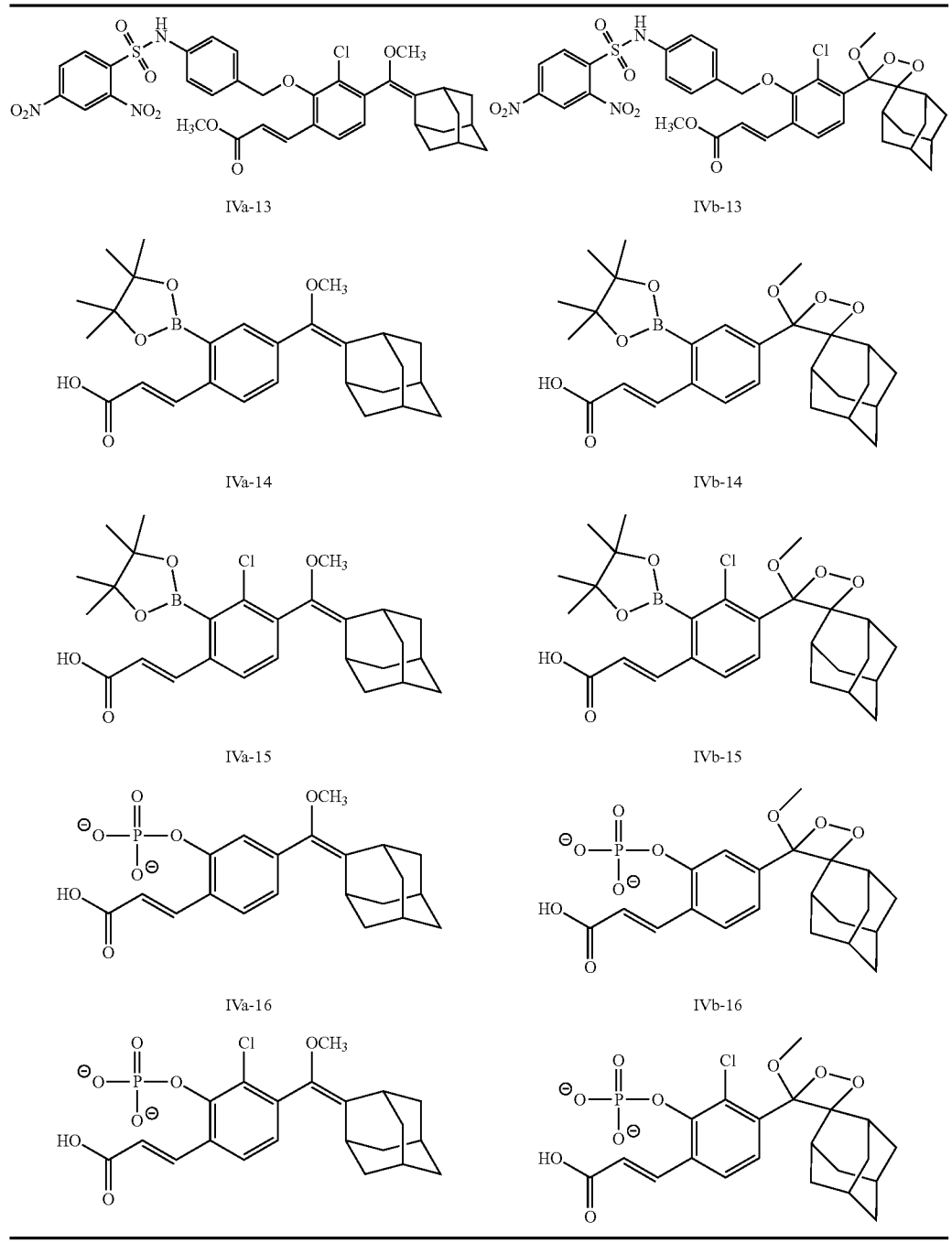

In a further aspect, the present invention provides a composition comprising a carrier, and a dioxetane-based chemiluminescence probe as disclosed herein, i.e., either a fluorophore-tethered dioxetane-based chemiluminescence probe of the formula IIIa/IIIb or a π* acceptor group-containing chemiluminescence probe of the formula IVa/IVb, each as defined in any one of the embodiments above.

In specific embodiments, the composition of the present invention comprises a chemiluminescence probe of the formula IIIa/IIIb selected from those listed in Table 5, or a chemiluminescence probe of the formula IVa/IVb selected from those listed in Table 7.

As shown herein, the composition of the present invention may thus be used for diagnostics and/or in vivo imaging. Triggered chemiluminescence emission can provide a highly sensitive readout of biological analytes. Chemiluminescence does not require light excitation, thereby drastically reducing background from autofluorescence and photoactivation of functional groups. Whereas bioluminescence, i.e., chemiluminescence derived from living systems that express bioluminescent enzymes such as luciferase, has found wide application for preclinical analysis of biological parameters using genetically modified organisms, small molecule chemiluminescence can be used with wild-type animals and opens up exciting opportunities for clinical imaging.

The compositions of the present invention may thus be inter alia pharmaceutical compositions, wherein said carrier is a pharmaceutically acceptable carrier.

As described above, chemiluminescence probes of the formulas IIIa/IIIb and IVa/IVb as disclosed herein have a cleavable caging group ($R^4$), e.g., an enzyme cleavable group, wherein removal of said cleavable group by the analyte of interest, e.g., in the presence of an enzyme capable of cleaving said enzyme cleavable group, generates an unstable phenolate-dioxetane species that decomposes through a chemiexcitation process to produce the excited intermediate, which then further decays to its ground-state through emission of light.

Particular chemiluminescence probes exemplified herein, having β-galactosyl as the caging group, are the fluorophore-tethered dioxetane-based chemiluminescence Probes 2 and 3, and the $\pi^*$ acceptor group-containing chemiluminescence Probes 6-9, and their chemiluminescent kinetic profiles in the presence vs. absent of β-galactosidase is shown in Studies 1 and 2. Additional probes exemplified in Study 2 are the $\pi^*$ acceptor group-containing chemiluminescence Probes 11 and 12, having phosphonate or 2,4-dinitrobenzene sulfonate as the caging group, which are capable of detecting alkaline-phosphatase and GSH, respectively; and the $\pi^*$ acceptor group-containing chemiluminescence Probe 10, having 4,4,5,5-tetramethyl-1,3,2-dioxaborolanyl as the caging group, which is capable of detecting hydrogen peroxide.

Other chemiluminescence probes may have a caging group comprising a peptide moiety consisting of two or more amino acid residues, e.g., a peptide moiety-containing caging group as shown in Table 1. Such peptide moieties may comprise an amino acid sequence cleavable by a specific enzyme, and probes containing such caging groups may thus be used for detecting the presence of said enzyme.

One particular such enzyme is cathepsin B, a lysosomal cysteine protease that plays an important role in intracellular proteolysis and is overexpressed in premalignant lesions and various pathological conditions, as well as in cancers, e.g., in tumor endothelial cells and many other tumor cells in the lysosome (Miller et al., 2009). Cathepsin B-cleavable peptides include, without limiting, peptides comprising the amino acid sequence Phe-Lys, Cit-Val, or Gly-Phe-Leu-Gly. Another particular such enzyme is cathepsin K, a lysosomal cysteine protease involved in bone remodeling and resorption, which is expressed predominantly in osteoclasts and overexpressed extracellularly in bone neoplasms (Segal et al., 2009). Cathepsin K-cleavable peptides include, without being limited to, peptides comprising the amino acid sequence Gly-Gly-Pro-Nle. A further particular such enzyme is legumain, a lysosomal enzyme overexpressed in tumor cells (Stern et al., 2009). Legumain-cleavable peptides include, without limiting, peptides comprising the modified amino acid sequence Cbz-Ala-Ala-Asn-ethylenediamine.

Pharmaceutical compositions according to the present invention may be prepared by conventional techniques, e.g., as described in Remington: The Science and Practice of Pharmacy, 19$^{th}$ Ed., 1995. The compositions can be prepared, e.g., by uniformly and intimately bringing the active agent, i.e., the dioxetane-based chemiluminescence probe, into association with a liquid carrier, a finely divided solid carrier, or both, and then, if necessary, shaping the product into the desired formulation. The compositions may be in liquid, solid or semisolid form and may further include pharmaceutically acceptable fillers, carriers, diluents or adjuvants, and other inert ingredients and excipients. In one embodiment, the pharmaceutical composition of the present invention is formulated as nanoparticles.

A pharmaceutical composition according to the present invention can be formulated for any suitable route of administration, e.g., for parenteral administration such as intravenous, intraarterial, intrathecal, intrapleural, intratracheal, intraperitoneal, intramuscular or subcutaneous administration, topical administration, oral or enteral administration, or for inhalation. In particular embodiments, such a composition is formulated for intravenous or intraperitoneal administration, or for subcutaneous administration, e.g., by an alzet pump implanted subcutaneous.

The pharmaceutical composition of the invention may be in the form of a sterile injectable aqueous or oleaginous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, e.g., water, Ringer's solution and isotonic sodium chloride solution.

The chemiluminescence emission of the probes of the present invention can be detected utilizing any technique or procedure known in the art.

Optical molecular imaging is a promising technique that provides a high degree of sensitivity and specificity in tumor margin detection. Furthermore, existing clinical applications have proven that optical molecular imaging is a powerful intraoperative tool for guiding surgeons performing precision procedures, thus enabling radical resection and improved survival rates. An example of a clinically approved instrument for minimally invasive surgical procedures under fluorescence guidance is the da Vinci Surgical System (Haber et al., 2010). This instrument is featured with a 3D HD vision system for a clear and magnified view inside a patient's body and allows surgeons to perform complex and routine procedures through a few small openings, similar to traditional laparoscopy. In addition, the following systems have already been applied in surgeries for breast cancer, liver metastases and bypassing graft surgery: The Hamamatsu's Photodynamic Eye (PDE™), Artemis™ and Novadaq SPY™ (Novadaq Technologies Inc., Toronto, Canada) (Chi et al., 2014). Several existing intraoperative NIR fluorescence molecular imaging systems were evaluated in clinical trials; including, Fluobeam®, FLARE™ and GXMI Navigator. They have played an important role in operation convenience, improving image assessment and increasing detection depth (Chi et al., 2014).

In recent years, there has been a great progress in the development of cameras and lasers for optical fluorescence imaging in the IR range (Mieog et al., 2011; Troyan et al., 2009). In parallel, there is a vast clinical use of low MW organic dyes such as ICG and methylene blue for determining cardiac output, hepatic function and liver blood flow, and for ophthalmic angiography. In 2015, the fluorescence imaging system, Xiralite®, gained FDA approval for visualization of microcirculation in the hands (for inflammation and perfusion-related disorders).

The invention will now be illustrated by the following non-limiting Examples.

Examples

Study 1. Remarkable Enhancement of Chemiluminescent Signal by Dioxetane-Fluorophore Conjugates: Turn-ON Chemiluminescence Probes with Color Modulation for Sensing and Imaging

Experimental

General. All reactions requiring anhydrous conditions were performed under an argon atmosphere. All reactions were carried out at RT unless stated otherwise. Chemicals and solvents were either analytical reagents (A. R.) grade or purified by standard techniques. TLC: silica gel plates Merck 60 F254: compounds were visualized by irradiation with UV light. Flash chromatography (FC): silica gel Merck 60 (particle size 0.040-0.063 mm), eluent given in parentheses. RP-HPLC: C18 5u, 250×4.6 mm, eluent given in parentheses. Preparative RP-HPLC: C18 5u, 250×21 mm, eluent given in parentheses. $^1$H-NMR spectra were recorded using Bruker Avance operated at 400 MHz. $^{13}$C-NMR spectra were recorded using Bruker Avance operated at 100 MHz. Chemical shifts were reported in ppm on the δ scale relative to a residual solvent (CDCl$_3$: δ=7.26 for $^1$H-NMR and 77.16 for $^{13}$C-NMR, DMSO-d$_6$: δ=2.50 for $^1$H-NMR and 39.52 for $^{13}$C-NMR). Mass spectra were measured on Waters Xevo TQD. Fluorescence and chemiluminescence were recorded on Molecular Devices Spectramax i3x. Images of microplate and mice were recorded on BioSpace Lab PhotonIMAGER™. All reagents, including salts and solvents, were purchased from Sigma-Aldrich.

Compound 1b. 2-chloro-3-hydroxybenzaldehyde (1a, 2000 mg, 12.77 mmol) was dissolved in 20 ml of methanol. Trimethyl orthoformate (2.24 ml, 20.44 mmol) and tertrabutylammonium tribromide (308 mg, 0.64 mmol) were added and the solution was stirred at RT. Reaction was monitored by TLC. Upon completion, reaction mixture was diluted with EtOAc (100 ml) and washed with 0.01M NaHCO$_3$(100 ml). Organic phase was dried over Na$_2$SO$_4$ and concentrated under reduced pressure. Purification by column chromatography (Hex:EtOAc 80:20) afforded 2460 mg (95% yield) of colorless oil. $^1$H NMR (400 MHz, CDCl$_3$): δ 7.22-7.17 (m, 2H), 7.04-6.99 (m, 1H), 5.82 (s, 1H), 5.58 (s, 1H), 3.37 (s, 6H). $^{13}$C NMR (100 MHz, CDCl$_3$): δ 151.65, 135.87, 127.58, 119.90, 119.13, 116.42, 101.03, 53.77. MS (ES-): m/z calc. for C$_9$H$_{11}$ClO$_3$: 202.0; found: 201.1 [M−H]$^-$.

Compound 1c. Phenol 1b (2450 mg, 12.09 mmol) and imidazole (1650 mg, 24.24 mmol) were dissolved in 15 ml of DCM. TBSCl (2180 mg, 14.46 mmol) was added and the solution was stirred at RT. Reaction was monitored by TLC. Upon completion, the white precipitate was filtered-off and the solvent was evaporated under reduced pressure. Purification by column chromatography (Hex:EtOAc 95:5) afforded 3600 mg (94% yield) of colorless oil. $^1$H NMR (400 MHz, CDCl$_3$): δ 7.23 (dd, J=7.8, 1.5 Hz, 1H), 7.14 (t, J=7.9 Hz, 1H), 6.88 (dd, J=8.0, 1.5 Hz, 1H), 5.63 (s, 1H), 3.37 (s, 6H), 1.03 (s, 9H), 0.22 (s, 6H). $^{13}$C NMR (100 MHz, CDCl$_3$): δ 151.81, 137.01, 126.74, 125.01, 120.62, 120.50, 101.29, 53.93, 25.81, 18.48, −4.23. MS (ES+): m/z calc. for C$_{15}$H$_{25}$ClO$_3$Si: 316.1; found: 285.1 [M —CH$_3$O$^-$]$^+$.

Compound 1d. Acetal 1c (3500 mg, 11.04 mmol) and trimethyl phosphite (1.7 ml, 14.41 mmol) were dissolved in 30 ml of DCM. Reaction mixture was cooled to 0° C. and titanium(IV) chloride (1.45 ml, 13.22 mmol) was added dropwise. Reaction was monitored by TLC. Upon completion, the solution was poured into a saturated aqueous solution of NaHCO$_3$(130 ml) at 0° C. After 10 minutes of stirring, 100 ml of DCM was added and the phases were separated. Organic phase was dried over Na$_2$SO$_4$ and concentrated under reduced pressure. Purification by column chromatography (Hex:EtOAc 40:60) afforded 4010 mg (92% yield) of colorless oil. $^1$H NMR (400 MHz, CDCl$_3$): δ 7.27 (dt, J=7.8, 1.9 Hz, 1H), 7.19 (t, J=7.9 Hz, 1H), 6.88 (dt, J=7.9, 1.6 Hz, 1H), 5.19 (d, J=15.7 Hz, 1H), 3.78 (d, J=10.6 Hz, 3H), 3.64 (d, J=10.5 Hz, 3H), 3.35 (s, 3H), 1.02 (s, 9H), 0.22 (s, 6H). $^{13}$C NMR (100 MHz, CDCl$_3$): δ 151.71, 134.03, 127.28, 126.10, 121.89, 120.48, 77.30, 75.60, 58.83, 53.81, 25.77, 18.46, −4.29. MS (ES+): m/z calc. for C$_{16}$H$_{28}$ClO$_5$PSi: 394.1; found: 395.3 [M+H]$^+$.

Compound 1e. Phosphonate 1d (3950 mg, 10.0 mmol) was dissolved in 25 ml of anhydrous THF under argon atmosphere at −78° C. LDA (2.0 M in THF, 6 ml, 12 mmol) was added and the solution was stirred for 20 minutes. A solution of 2-adamantanone (2250 mg, 14.98 mmol) in 20 ml of THF was added, and after 15 minutes of stirring at −78° C. reaction was allowed to warm to RT. Reaction was monitored by TLC. Upon completion, reaction mixture was diluted with EtOAc (150 ml) and washed with brine (150 ml). Organic phase was dried over Na$_2$SO$_4$ and concentrated under reduced pressure. Purification by column chromatography (Hex:EtOAc 95:5) afforded 3560 mg (85% yield) of white solid. $^1$H NMR (400 MHz, CDCl$_3$): δ 7.09 (t, J=8.0 Hz, 1H), 6.89-6.84 (m, 2H), 3.30 (s, 3H), 3.27 (s, 1H), 2.05 (s, 1H), 1.97-1.65 (m, 12H), 1.04 (s, 9H), 0.23 (s, 6H). $^{13}$C NMR (100 MHz, CDCl$_3$): δ 151.98, 140.24, 136.20, 130.69, 126.69, 126.58, 124.93, 120.30, 56.98, 39.28, 39.14, 38.74, 37.32, 32.96, 29.70, 28.58, 28.43, 25.86, 18.54, −4.28. MS (ES+): m/z calc. for C$_{24}$H$_{35}$ClO$_2$Si: 418.2; found: 419.3 [M+H]$^+$.

Compound 1f. Compound 1e (3500 mg, 8.35 mmol) was dissolved in 30 ml of THF. Tetrabutylammonium fluoride (1.0 M in THF, 9.2 ml, 9.2 mmol) was added and the solution was stirred at RT. Reaction was monitored by TLC. Upon completion, reaction mixture was diluted with EtOAc (150 ml) and washed with 1M HCl (100 ml). Organic phase was dried over Na$_2$SO$_4$ and concentrated under reduced pressure. Purification by column chromatography (Hex:EtOAc 85:15) afforded 2420 mg (95% yield) of white solid. $^1$H NMR (400 MHz, CDCl$_3$): δ 7.15 (t, J=7.8 Hz, 1H), 6.99 (dd, J=8.2, 1.3 Hz, 1H), 6.83 (dd, J=7.5, 1.3 Hz, 1H), 5.90 (s, 1H), 3.31 (s, 3H), 3.27 (s, 1H), 2.10 (s, 1H), 2.00-1.64 (m, 12H). $^{13}$C NMR (100 MHz, CDCl$_3$): δ 151.82, 139.77, 135.06, 131.96, 127.39, 123.95, 120.68, 115.60, 57.16, 39.23, 39.14, 38.85, 38.71, 37.18, 32.89, 29.73, 28.46, 28.34. MS (ES-): m/z calc. for C$_{18}$H$_{21}$ClO$_2$: 304.1; found: 303.2 [M−H]$^-$.

Scheme 3: Synthesis of compounds 1b-1f

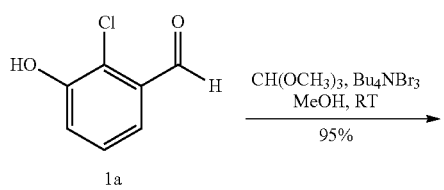

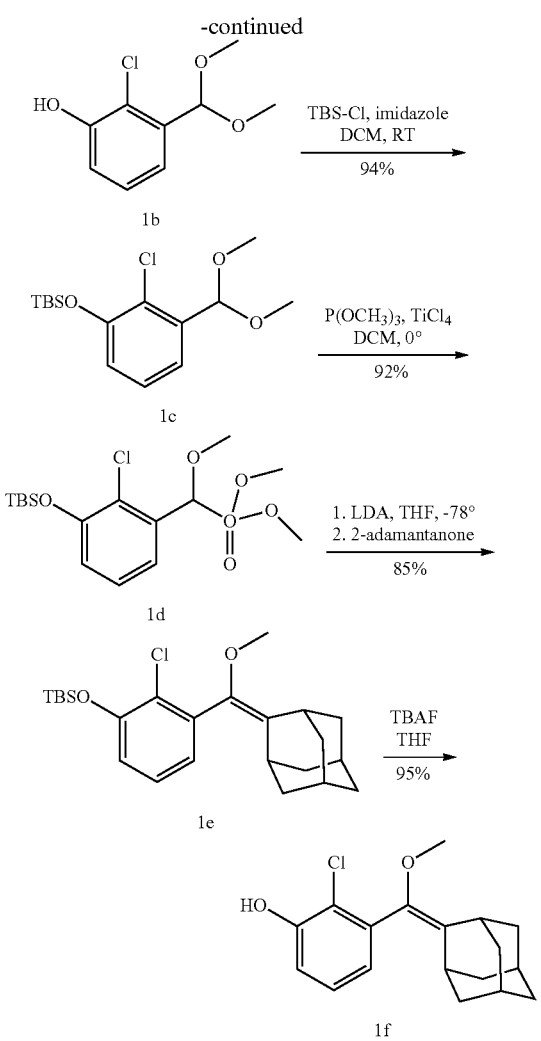

Compound 1g. Phenol 1f (1500 mg, 4.92 mmol) was dissolved in 5 ml of DCM and 10 ml of quinoline. Acetobromo-α-D-galactose (2430 mg, 5.91 mmol) and silver carbonate (1760 mg, 6.38 mmol) were added and the solution was stirred at RT. Reaction was monitored by TLC. Upon completion, reaction mixture was diluted with DCM (120 ml) followed by filtration over celite. The filtrate was washed with 1M HCl (2×100 ml) and brine (100 ml). Organic phase was dried over $Na_2SO_4$ and concentrated under reduced pressure. Purification by column chromatography (Hex:EtOAc 70:30) afforded 2720 mg (87% yield) of white solid. $^1$H NMR (400 MHz, $CDCl_3$): δ 7.17 (d, J=5.1 Hz, 2H), 7.01 (t, J=4.5 Hz, 1H), 5.59 (t, J=9.2 Hz, 1H), 5.47 (dd, J=3.3, 0.7 Hz, 1H), 5.11 (dd, J=10.5, 3.4 Hz, 1H), 4.98 (dd, J=8.0, 2.2 Hz, 1H), 4.31-4.23 (m, 1H), 4.20-4.13 (m, 1H), 4.08-4.03 (m, 1H), 3.33 (s, 1H), 3.26 (s, 3H), 2.19 (s, 3H), 2.08 (s, 3H), 2.07 (s, 3H), 2.01 (s, 3H), 2.00-1.66 (m, 13H). $^{13}$C NMR (100 MHz, $CDCl_3$): δ 170.51, 170.39, 170.32, 169.57, 152.99, 139.74, 136.42, 131.54, 127.08, 126.82, 125.32, 118.07, 100.97, 71.24, 70.77, 68.32, 66.95, 61.45, 57.45, 57.07, 39.29, 39.19, 38.84, 38.68, 37.19, 32.88, 29.78, 28.46, 28.30, 20.99, 20.80, 20.73. MS (ES+): m/z calc. for $C_{32}H_{39}ClO_{11}$: 634.2; found: 635.3 [M+H]$^+$.

Compound 1h. Compound 1g (2000 mg, 3.15 mmol), bis(pinacolato)diboron (1440 mg, 5.67 mmol), (1,5-cyclooctadiene)(methoxy)iridium(I) dimer (42 mg, 0.063 mmol) and BBBPY (34 mg, 0.127 mmol) were dissolved in 20 ml of anhydrous THF in a sealed tube. Reaction mixture was stirred at 80° C. for 2 hours, and was monitored by $^1$H-NMR (appearance of two aromatic hydrogens at 7.48 and 7.43 ppm and disappearance of the aromatic hydrogens of 1g). Upon completion, the solvent was evaporated under reduced pressure. The crude product was passed through silica gel column (Hex:EtOAc 65:35) to afford 2130 mg (89% yield) of white solid that was taken to the next step without further purification.

Compound 1j. Arylboronate ester 1h (2100 mg, 2.76 mmol), benzyl bromide 1i (Jacobson et al., 1988) (950 mg, 3.04 mmol) and potassium carbonate (950 mg, 6.87 mmol) were dissolved in 20 ml of anhydrous 1,4-dioxane. The solution was thoroughly degassed by bubbling of argon and then tetrakis(triphenylphosphine)palladium(0) (320 mg, 0.28 mmol) was added. The flask was sealed and the solution was stirred at 120° C. for 2 hours. Reaction was monitored by TLC. Upon completion, the solvent was evaporated under reduced pressure. Purification by column chromatography (Hex:EtOAc 40:60) afforded 950 mg (40% yield) of white solid. $^1$H NMR (400 MHz, $CDCl_3$): δ 8.06 (d, J=8.3 Hz, 2H), 7.30 (d, J=8.3 Hz, 2H), 7.00 (s, 1H), 6.82 (s, 1H), 5.55 (t, J=9.2 Hz, 1H), 5.44 (d, J=2.8 Hz, 1H), 5.09 (dd, J=10.5, 3.4 Hz, 1H), 4.94 (dd, J=7.8, 2.6 Hz, 1H), 4.19-4.13 (m, 2H), 4.06-3.96 (m, 3H), 3.31 (s, 1H), 3.24 (s, 3H), 2.89 (s, 4H), 2.17 (s, 3H), 2.07 (s, 3H), 2.02 (s, 3H), 2.00 (s, 3H), 1.98-1.63 (m, 13H). $^{13}$C NMR (100 MHz, $CDCl_3$): δ 170.42, 170.34, 170.24, 169.54, 169.38, 161.73, 152.93, 147.95, 138.59, 136.73, 136.51, 131.10, 129.31, 127.73, 127.52, 123.57, 123.50, 118.93, 100.88, 71.18, 70.66, 68.28, 66.89, 61.37, 57.52, 57.14, 41.58, 39.17, 39.09, 38.82, 38.61, 37.13, 32.99, 32.94, 29.74, 29.69, 28.38, 28.28, 25.77, 24.93, 24.67, 20.96, 20.75, 20.69. MS (ES+): m/z calc. for $C_{44}H_{48}ClNO_{15}$: 865.3; found: 888.4 [M+Na]$^+$.

Scheme 4: Synthesis of compounds 1g-1k

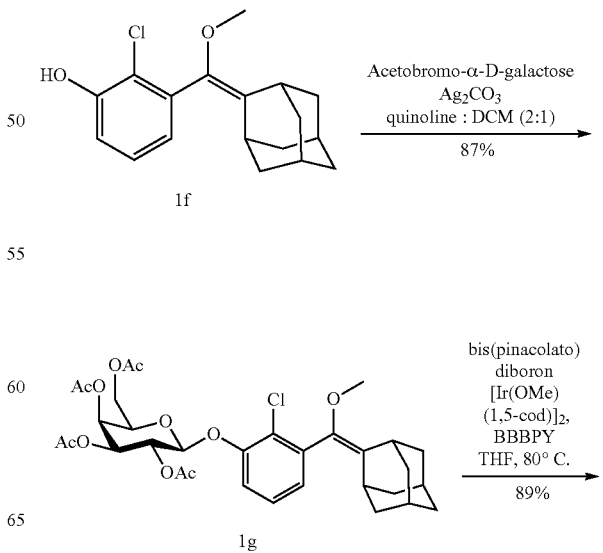

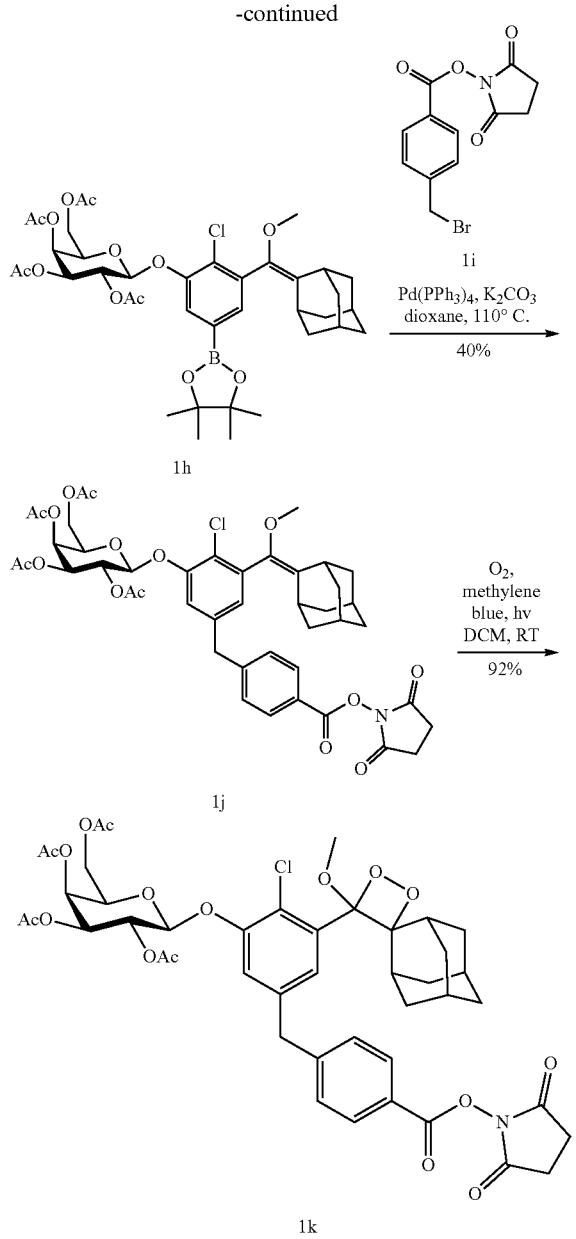

Compound 1k. Enol ether 1j (250 mg, 0.29 mmol) and few milligrams of methylene blue were dissolved in 20 ml of DCM. Oxygen was bubbled through the solution while irradiating with yellow light. Reaction was monitored by TLC. Upon completion, the solvent was concentrated under reduced pressure. Purification by column chromatography (Hex:EtOAc 35:65) afforded 238 mg (92% yield) of white solid. The product was isolated as a mixture of diastereomers. $^1$H NMR (400 MHz, CDCl$_3$): δ 8.06 (d, J=7.9 Hz, 2H), 7.75-7.67 (m, 1H), 7.31 (d, J=7.5 Hz, 2H), 7.12-7.02 (m, 1H), 5.59-5.49 (m, 1H), 5.42 (s, 1H), 5.07 (d, J=10.3 Hz, 1H), 4.87 (d, J=7.8 Hz, 1H), 4.14-4.10 (m, 2H), 4.08 (s, 2H), 4.03-3.95 (m, 1H), 3.22-3.10 (m, 3H), 3.02-2.94 (m, 1H), 2.88 (s, 4H), 2.32-2.21 (m, 1H), 2.15 (s,3H), 2.07-1.95 (m, 9H), 1.93-1.53 (m, 12H). $^{13}$C NMR (100 MHz, CDCl$_3$): δ 170.32, 170.22, 170.11, 169.41, 169.32, 161.66, 153.87, 147.63, 139.21, 133.92, 131.12, 129.29, 128.62, 123.61, 120.10, 111.81, 100.95, 96.42, 71.28, 70.54, 68.32, 68.22, 66.84, 66.79, 61.31, 61.23, 49.75, 41.75, 36.60, 33.84, 33.73, 33.64, 32.67, 32.31, 31.63, 31.52, 26.21, 26.00, 25.75, 22.70, 20.90, 20.68, 20.62, 14.17. MS (ES+): m/z calc. for C$_{44}$H$_{48}$ClNO$_{17}$: 897.3; found: 920.7 [M+Na]$^+$.

Probe 1. Enol ether 1g (100 mg, 0.157 mmol) and few milligrams of methylene blue were dissolved in 10 ml of DCM. Oxygen was bubbled through the solution while irradiating with yellow light. Reaction was monitored by TLC. Upon completion, the solvent was concentrated under reduced pressure and the crude product was passed through silica gel column (Hex:EtOAc 60:40) to remove methylene blue. The solvent was evaporated and the product was dissolved in McOH (3 ml). Potassium carbonate (87 mg, 0.63 mmol) was added and the solution was stirred at RT. Reaction was monitored by RP-HPLC. Purification by RP-HPLC (30-100% ACN in water, 20 min) afforded 67 mg (85% yield) of white solid. The product was isolated as a mixture of diastereomers. $^1$H NMR (400 MHz, CDCl$_3$): δ 7.79 (d, J=7.3 Hz, 1H), 7.30 (t, J=7.8 Hz, 1H), 7.22 (d, J=8.1 Hz, 1H), 4.89-4.72 (m, 1H), 4.34-4.19 (m, 5H), 4.15-4.07 (m, 1H), 3.91-3.77 (m, 3H), 3.64 (m, 1H), 3.20-3.04 (m, 3H), 2.96 (s, 1H), 2.28-2.17 (m, 1H), 2.01-1.46 (m, 12H). $^{13}$C NMR (100 MHz, CDCl$_3$): δ 153.52, 133.82, 127.55, 122.27, 118.89, 111.91, 102.45, 96.22, 74.51, 73.24, 71.20, 69.06, 61.46, 49.73, 36.66, 34.01, 33.57, 32.71, 32.30, 31.72, 26.20, 25.97, 22.79, 14.26. MS (ES-): m/z calc. for C$_{24}$H$_3$ClO$_9$: 498.2; found: 543.3 [M+HCOO$^-$]$^-$ Scheme 5: Synthesis of Probe 1

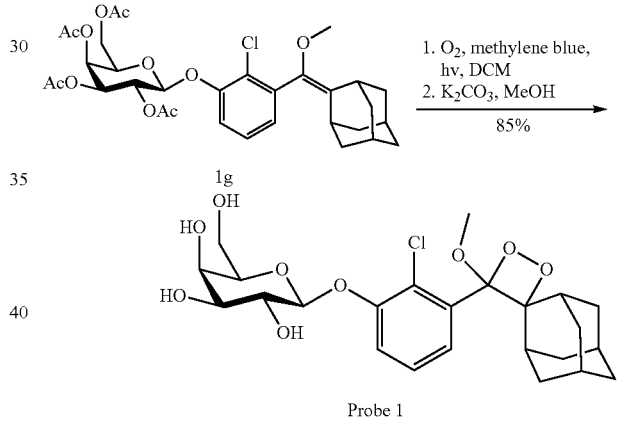

Probe 1

Compound 2b. Fluorescein isothiocyanate 2a (150 mg, 0.385 mmol) and N-Boc-ethylenediamine (68 mg, 0.42 mmol) were dissolved in 2 ml of DMF. 3 drops of Et$_3$N were added and the solution was stirred at RT. Reaction was monitored by TLC. Upon completion the solvent was evaporated under reduced pressure. Purification by column chromatography (Hex:EtOAc 25:75) afforded 192 mg (91% yield) of orange solid. $^1$H NMR (400 MHz, DMSO): δ 10.45-9.76 (m, 3H), 8.21 (s, 1H), 8.05 (s, 1H), 7.74 (d, J=6.4 Hz, 1H), 7.18 (d, J=8.2 Hz, 1H), 6.95 (s, 1H), 6.68 (s, 2H), 6.63-6.53 (m, 4H), 3.48-3.35 (m, 2H), 3.22-3.09 (m, 2H), 1.38 (s, 9H). $^{13}$C NMR (100 MHz, DMSO): δ 180.70, 168.54, 159.54, 155.87, 151.92, 147.30, 141.19, 129.68, 129.07, 126.60, 124.13, 116.72, 112.63, 109.74, 102.28, 77.86, 43.83, (two peaks of ethylenediamine linker are hidden under solvent signal), 28.26. MS (ES+): m/z calc. for C$_{28}$H$_{27}$N$_3$O$_7$S: 549.2; found: 550.3 [M+H]$^+$.

Compound 2c. Compound 2b (40 mg, 0.073 mmol) was dissolved in 2 ml of 1:1 mixture of TFA and DCM. Reaction was stirred at RT and monitored by TLC. Upon completion, the solvent was removed under reduced pressure and the product was taken to the next step without further purification.

Scheme 6: Synthesis of compounds 2b-2c and Probe 2

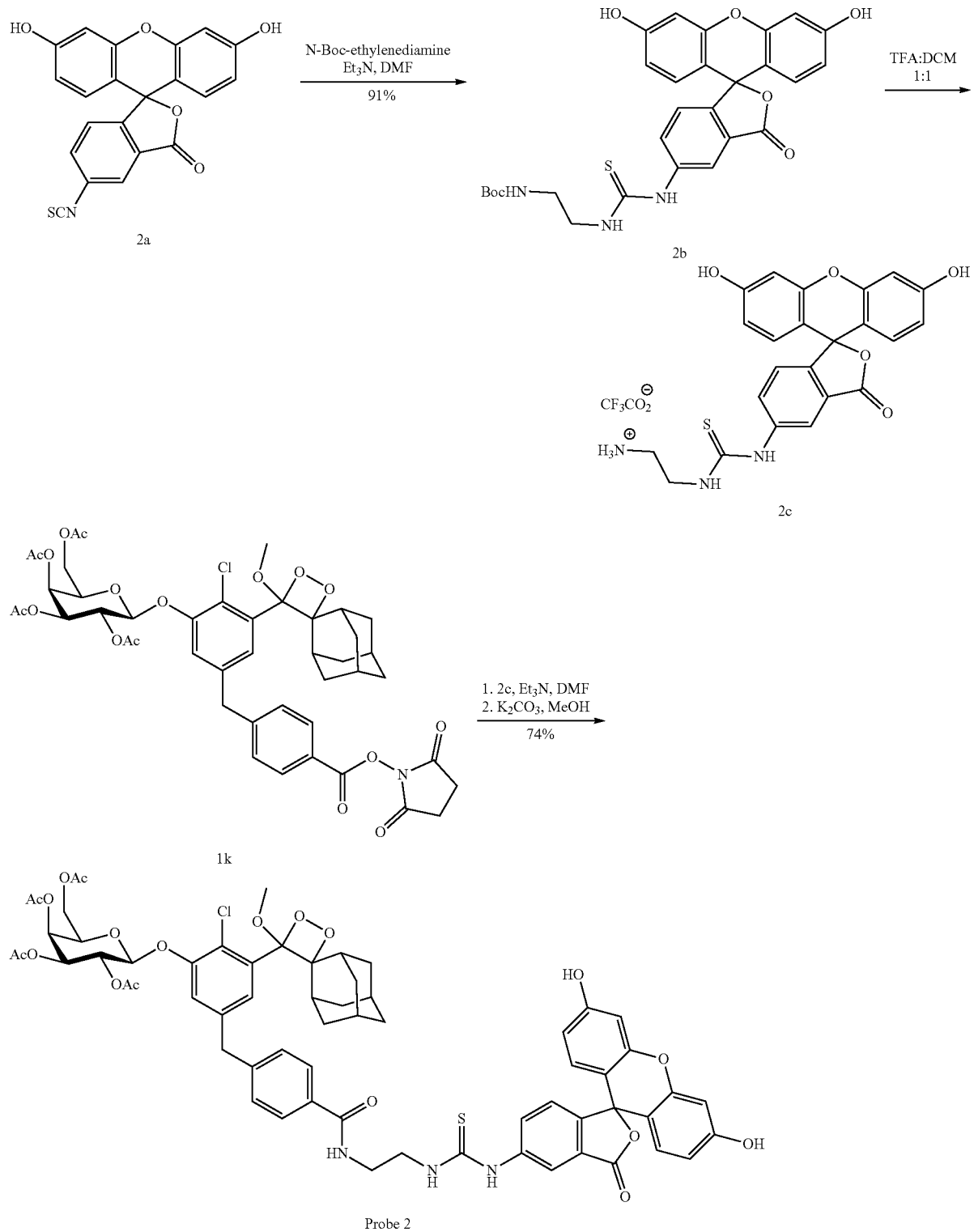

Probe 2. Amine-functionalized fluorescein 2c (41 mg, 0.073 mmol) and NHS ester 1k (65.5 mg, 0.073 mmol) were dissolved in 1 ml of DMF. The flask was kept in the dark by covering it with an aluminum foil and 2 drops of Et₃N were added. Reaction was stirred at RT and was monitored by RP-HPLC. Upon completion, the solvent was evaporated under reduced pressure and the resulting yellow solid was dissolved in 1.5 ml of McOH. Potassium carbonate (40 mg, 0.29 mmol) was added and removal of sugar acetates was monitored by RP-HPLC. Upon completion the product was purified by RP-HPLC (30-100% ACN in water, 20 min) to afford 57 mg (74% yield) of yellow solid. The product was isolated as a mixture of diastereomers. $^1$H NMR (400 MHz, DMSO): δ 10.33-9.85 (m, 3H), 8.59 (s, 1H), 8.22 (d, J=1.7 Hz, 1H), 8.16 (s, 1H), 7.81 (d, J=7.6 Hz, 2H), 7.76-7.69 (m, 1H), 7.45 (s, 1H), 7.37-7.28 (m, 3H), 7.17 (d, J=8.3 Hz, 1H), 6.67 (d, J=2.3 Hz, 2H), 6.63-6.52 (m, 4H), 5.04-4.85 (m, 1H), 4.21-3.94 (m, 5H=2H of benzylic singlet +3H of the sugar moiety, under broad H$_2$O peak), 3.78-3.38 (m, 11H), 3.08-2.99 (m, 3H), 2.84 (s, 1H), 2.32-2.16 (m, 1H), 1.94-1.35 (m, 12H). $^{13}$C NMR (100 MHz, DMSO): δ 180.74, 168.45, 166.56, 159.48, 153.62, 153.38, 151.88, 147.29, 143.99, 141.15, 140.26, 132.33, 132.03, 129.77, 129.31, 129.01, 128.49, 127.54, 126.57, 125.51, 124.07, 118.17, 118.03, 117.87, 116.88, 112.57, 111.51, 109.72, 102.23, 101.05, 100.38, 95.27, 75.59, 73.54, 70.22, 70.13, 67.97, 60.13, 59.74, 51.43, 49.22, 43.57, 38.46, 35.89, 33.21, 32.89, 31.91, 31.75, 31.05, 30.75, 28.99, 28.24, 26.83, 25.49, 25.16. MS (ES-): m/z calc. for $C_{55}H_{54}ClN_3O_{15}S$: 1063.3; found: 1062.7 [M−H]$^−$.

Compound 3b. Compound 3a (Karton-Lifshin et al., 2012) (180 mg, 0.30 mmol), N-Boc-ethylenediamine (96 mg, 0.60 mmol) and 2-(1H-benzotriazol-1-yl)-1,1,3,3-tetramethyluronium hexafluorophosphate (HBTU) (228 mg, 0.60 mmol) were dissolved in 3 ml of DMF. Triethylamine (120 μL, 0.86 mmol) was added and reaction mixture was stirred at RT. Reaction was monitored by RP-HPLC (10-90% ACN in water, 20 min). Upon completion, the solvent was evaporated under reduced pressure. Crude product was dissolved in 5 ml of H$_2$O, few drops of McOH and few drops of AcOH. Purification by RP-HPLC (10-90% ACN in water, 20 min) afforded 187 mg (84% yield) of yellow solid. $^1$H NMR (400 MHz, DMSO): δ 8.88 (d, J=6.7 Hz, 4H), 8.69 (s, 1H), 8.33 (s, 2H), 8.31-8.19 (m, 6H), 7.53 (d, J=16.2 Hz, 2H), 6.96 (s, 1H), 4.28 (s, 6H), 3.35 (dd, J=11.9, 6.0 Hz, 2H), 3.15 (dd, J=11.9, 5.9 Hz, 2H), 1.37 (s, 9H). $^{13}$C NMR (100 MHz, DMSO): δ 165.45, 157.39, 155.83, 152.51, 145.25, 135.09, 128.47, 126.54, 124.30, 124.06, 123.69, 77.75, 46.97 (two peaks of ethylenediamine linker are hidden under solvent signal), 28.26 (TFA signals are not shown). MS (ES+): m/z calc. for $C_{30}H_{35}N_4O_4^+$ (quinone form): 515.3; found: 515.5.

Compound 3c. Compound 3b (60 mg, 0.081 mmol) was dissolved in 2 ml of 1:1 mixture of TFA and DCM. Reaction was stirred at RT and monitored by RP-HPLC (10 90% ACN in water, 20 min). Upon completion, the solvent was removed under reduced pressure and the product was taken to the next step without further purification.

Probe 3. Amine-functionalized QCy 3c (60 mg, 0.081 mmol) and NHS ester 1k (72.5 mg, 0.081 mmol) were dissolved in 1 ml of DMF. The flask was kept in the dark by covering it with an aluminum foil and 2 drops of Et$_3$N were added. Reaction was stirred at RT and was monitored by RP-HPLC. Upon completion, the solvent was evaporated under reduced pressure and the resulting yellow solid was dissolved in 1.5 ml of McOH. Potassium carbonate (45 mg, 0.33 mmol) was added and removal of sugar acetates was monitored by RP-HPLC. Upon completion the product was purified by RP-HPLC (30-100% ACN in water, 20 min) to afford 83 mg (82% yield) of yellow solid. The product was isolated as a mixture of diastereomers. $^1$H NMR (400 MHz, DMSO): δ 8.88 (d, J=6.7 Hz, 4H), 8.77 (s, 1H), 8.63 (s, 1H), 8.34 (s, 2H), 8.29-8.21 (m, 6H), 7.81 (d, J=7.9 Hz, 2H), 7.53 (d, J=16.2 Hz, 2H), 7.44 (s, 1H), 7.36-7.30 (m, 3H), 5.04-4.88 (m, 1H), 4.70-4.50 (m, 3H of the sugar moiety, under broad H$_2$O peak), 4.28 (s, 6H), 4.06 (s, 2H), 3.72 (d, J=2.7 Hz, 1H), 3.65-3.37 (m, 10H), 3.10-2.99 (m, 3H), 2.83 (s, 1H), 2.24 (d, J=12.0 Hz, 1H), 1.96-1.21 (m, 12H). $^{13}$C NMR (100 MHz, DMSO): δ 166.40, 165.56, 157.25, 152.45, 145.25, 144.02, 140.35, 135.01, 132.47, 132.03, 128.54, 128.46, 127.54, 126.62, 125.49, 124.35, 124.03, 123.67, 117.95, 117.82, 111.55, 101.01, 100.31, 95.30, 75.56, 73.58, 70.25, 67.98, 60.14, 49.22, 46.99, 40.53, 35.91, 33.21, 32.90, 31.93, 31.78, 31.06, 30.75, 25.52, 25.17 (TFA signals are not shown). MS (ES+): m/z calc. for $C_{57}H_{62}ClN_4O_{12}^+$ (quinone form): 1029.4; found: 1029.8.

Scheme 7: Synthesis of compounds 3b-3c and Probe 3

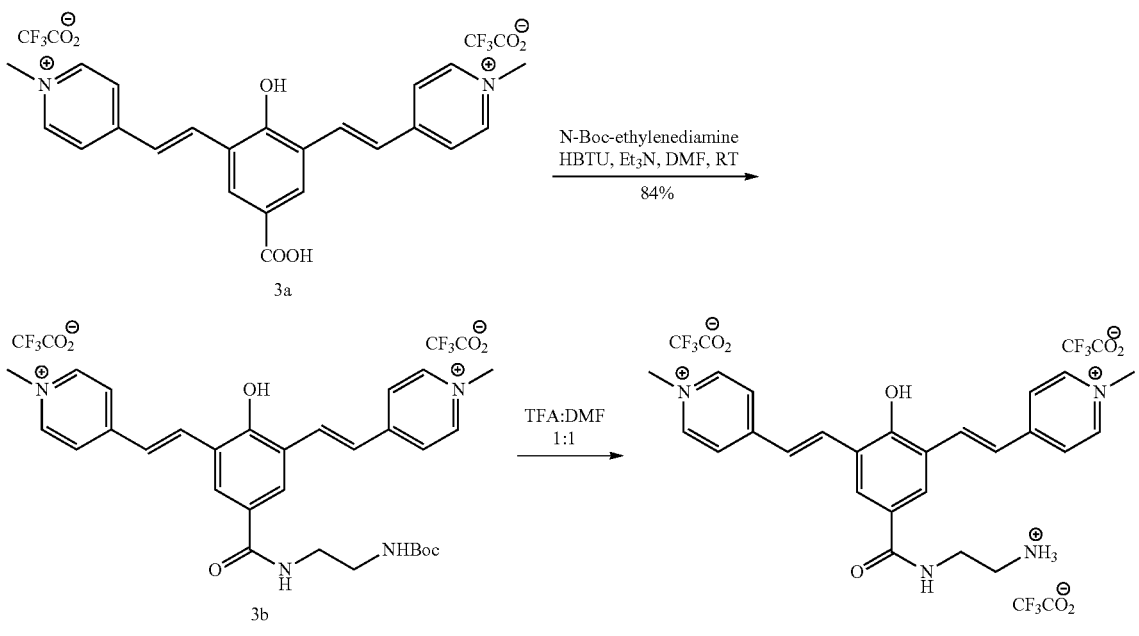

-continued

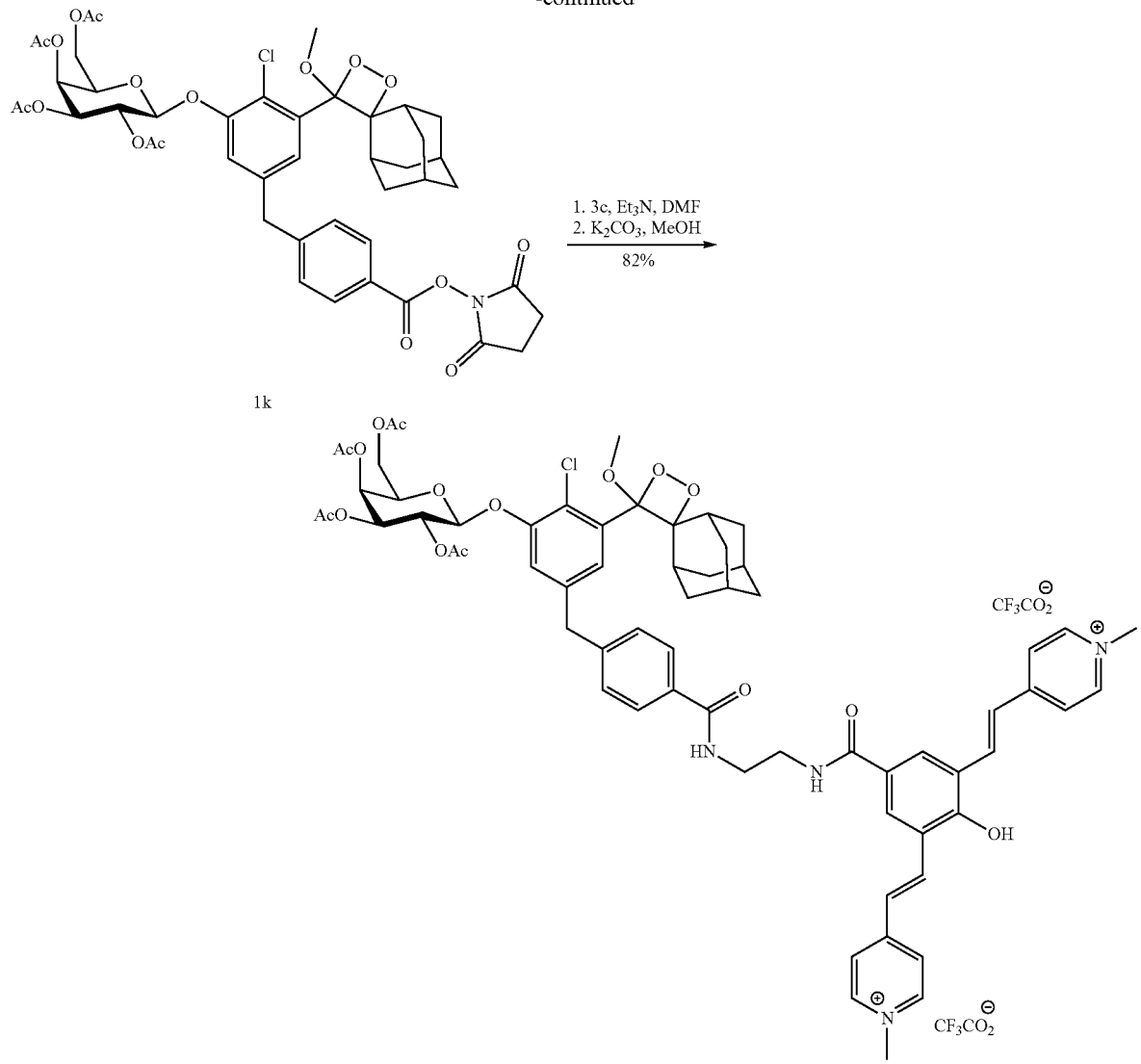

Probe 3

In vivo evaluations. All animal procedures were performed in compliance with Tel-Aviv University, Sackler School of Medicine guidelines and protocols approved by the institutional animal care and use committee.

Six 7-weeks old BALB/c female mice (Harlan Laboratories Israel Ltd., Jerusalem, Israel) were anesthetized using a mixture of ketamine (100 mg/kg) and xylazine (12 mg/kg) injected subcutaneously. Then, mice were injected intraperitoneally or subcutaneously with 50 µL of the probe solution, previously incubated in PBS 7.4 (in the presence or absence of β-galactosidase) for 30 minutes. The mice were imaged and chemiluminescence was monitored for up to 15 min by intravital non-invasive bioluminescence imaging system (Photon Imager; Biospace Lab, Paris, France) Images were obtained by Photo-Acquisition software (Biospace Lab) and analyzed by M3Vision Software (Biospace Lab).

Optical imaging holds several advantages over other imaging modalities (e.g., radiography, magnetic resonance imaging and ultrasound). Fluorescent molecular probes at the NIR range, possess good spatial resolution and greater depth penetration than other wavelengths. In vivo imaging is required for determining the limit of detection and signal penetration in live tissues. This data cannot be obtained by in vitro methods. These preliminary experiments use the minimal number of animals to evaluate our new probe in terms of proof of concept (Redy-Keisar et al., 2015b). At the end of the experiment, mice were euthanized by cervical dislocation.

Chemiluminescence microscopy imaging of β-galactosidase activity. Chemiluminescence images were acquired using Olympus LV200 inverted microscope fitted with an EMCCD camera (Hamamatsu $C_{9100}$-13). HEK293 LacZ stable cells (amsbio SC003) and HEK293-WT cells (control) were grown on 35 mm glass bottom petri dishes at 37° C. for 24 h. Cell culture medium was changed to Molecular Probes® Live Cell Imaging Solution containing 5 µM of Probe 3. Cells were incubated for another 20 minutes at 37° C. Thereafter, images were recorded with 20 minutes exposure time.

Results and Discussion

Design and synthesis of fluorophore-tethered dioxetane probes. The general structure of the dioxetane-fluorophore conjugate and its activation mechanism are presented in Scheme 8. Removal of the trigger by the analyte of interest initiates the CIEEL mechanism, which leads to energy transfer from the excited benzoate to the dye, resulting in excitation of the fluorophore. Thus, light emission should occur from a highly emissive species (the fluorophore) at its corresponding wavelength.

We sought to develop a practical synthetic pathway that allows modular attachment of a fluorophore to the phenolic ring. Dioxetane is usually prepared by reaction of singlet oxygen with a double bond. Since conditions for production of singlet oxygen are not always compatible with the presence of a fluorophore, we developed a late-stage functionalization chemistry that allows attachment of the fluorophore after preparation of the dioxetane. The synthesis of a dioxetane-fluorophore conjugate designed for activation by β-galactosidase (as a model enzyme) is shown in Scheme 9. Commercially available aldehyde 1a was protected with trimethyl orthoformate to give acetal 1b, followed by additional protection of the phenol group with TBSCl to afford compound 1c. The latter was reacted with trimethylphosphite to produce phosphonate 1d, which was condensed with 2-adamantanone via the Wittig-Horner reaction to give enol ether 1e. Deprotection of the TBS group of 1e gave phenol 1f, which was alkylated with a bromo-galactose derivative to afford compound 1g. Hartwig-Miyaura C—H borylation (Ishiyama et al., 2002) of 1g afforded phenylboronic ester 1h, which was coupled with benzyl bromide 1i via Suzuki coupling reaction to give compound 1j. Oxidation of 1j with singlet oxygen gave NHS-ester-functionalized dioxetane 1k. This NHS-ester readily reacts with various amine-functionalized dyes to afford dioxetane-fluorophore conjugate 1m.

Scheme 8: Chemiluminescent activation pathway of dioxetane-tethered fluorophore

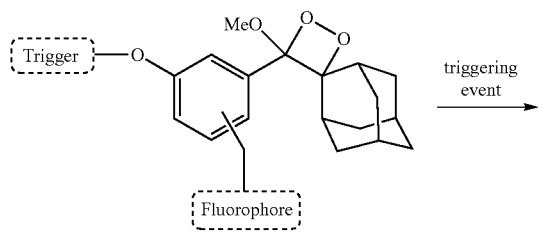

Following the synthetic strategy presented in Scheme 9, we prepared three different chemiluminescent probes (Probes 1-3, see Schemes 5-7) for monitoring of β-galactosidase activity. Probes 2 and 3 are composed of dioxetane tethered with the fluorogenic dyes fluorescein and QCy (Karton-Lifshin et al., 2011; Karton-Lifshin et al., 2012), respectively. Probe 1 is a basic Schaap-dioxetane without a tethered dye. The chlorine substituent on the phenolic ring was introduced in order to decrease the pKa of the phenol released after cleavage of the β-galactosidase substrate. Such a pKa should allow the chemiexcitation pathway of the dioxetane to occur under physiological conditions.

Scheme 9: Synthetic strategy for dioxetane-fluorophore conjugates

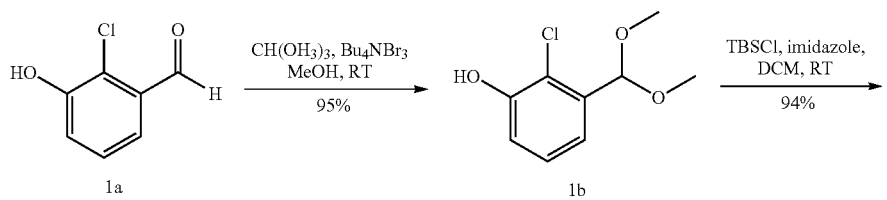

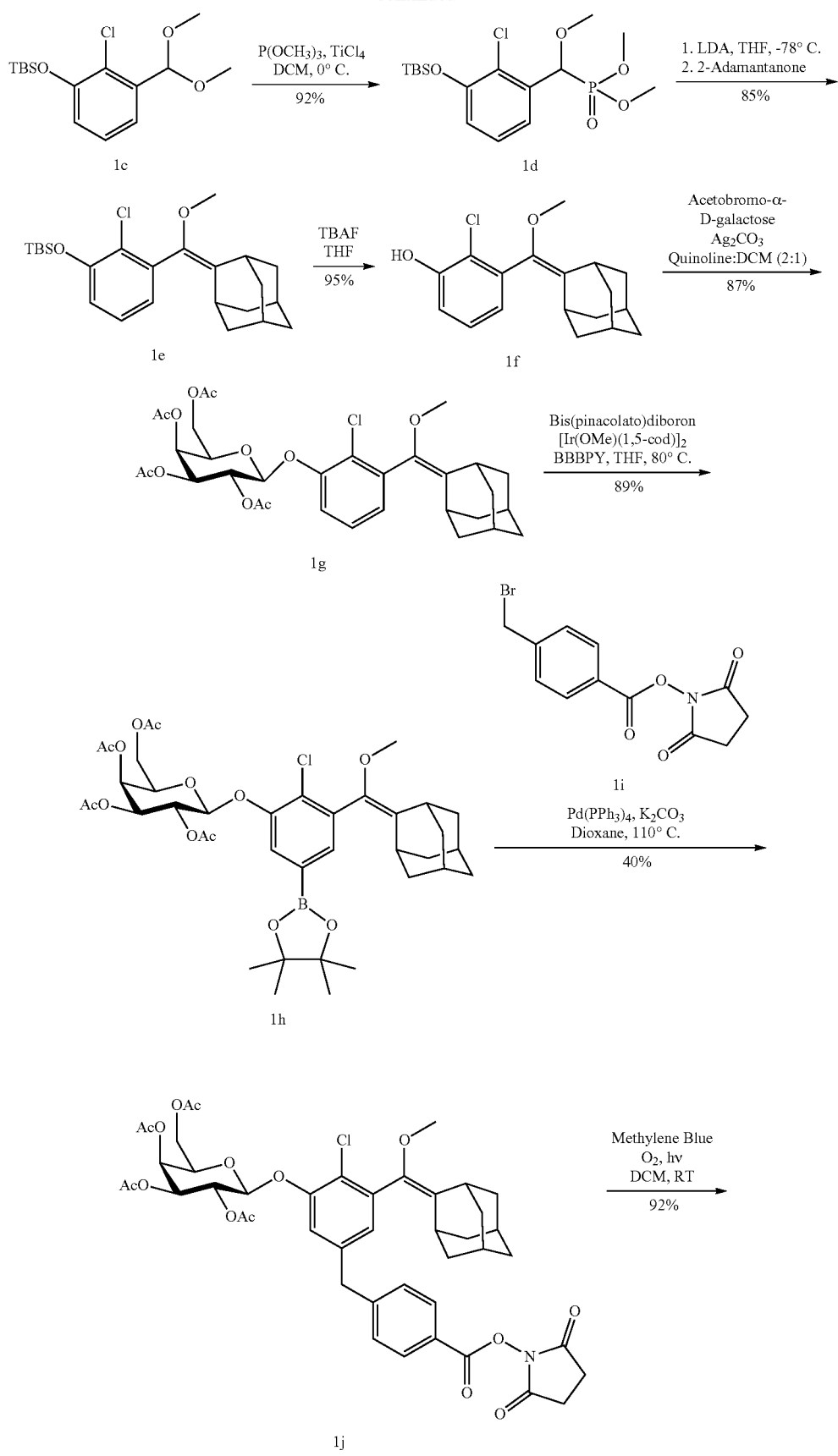

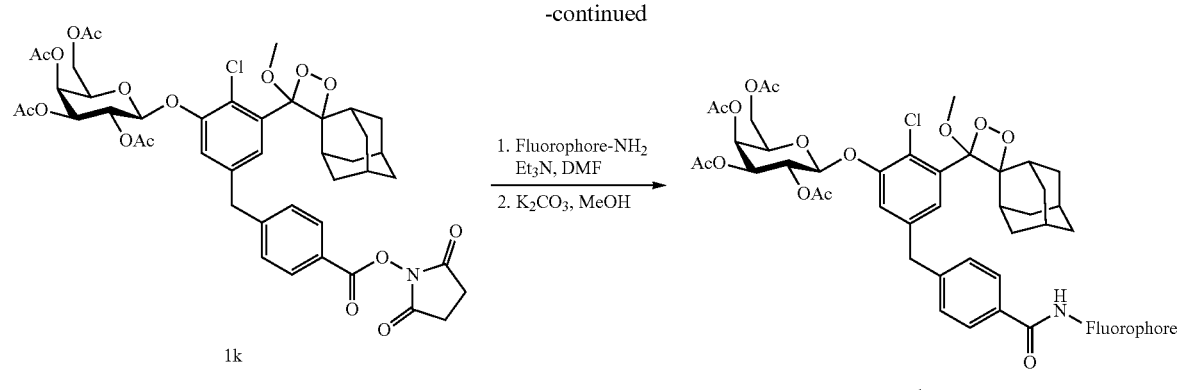

Figure 1:
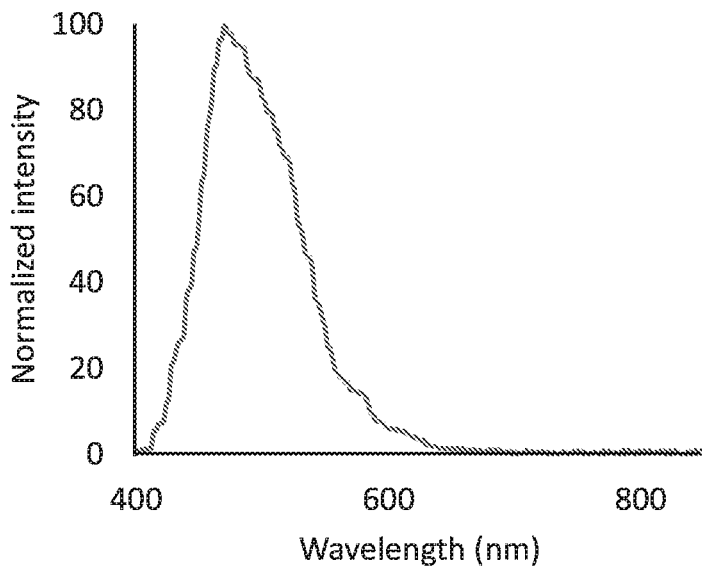
FIG. 1 shows chemiluminescent emission spectrum of 1 μM Probe 1,$\lambda_{max}$=470 nm, recorded in PBS, pH 7.4, in the presence of 1.5 units/mL β-galactosidase.
Figure 2:
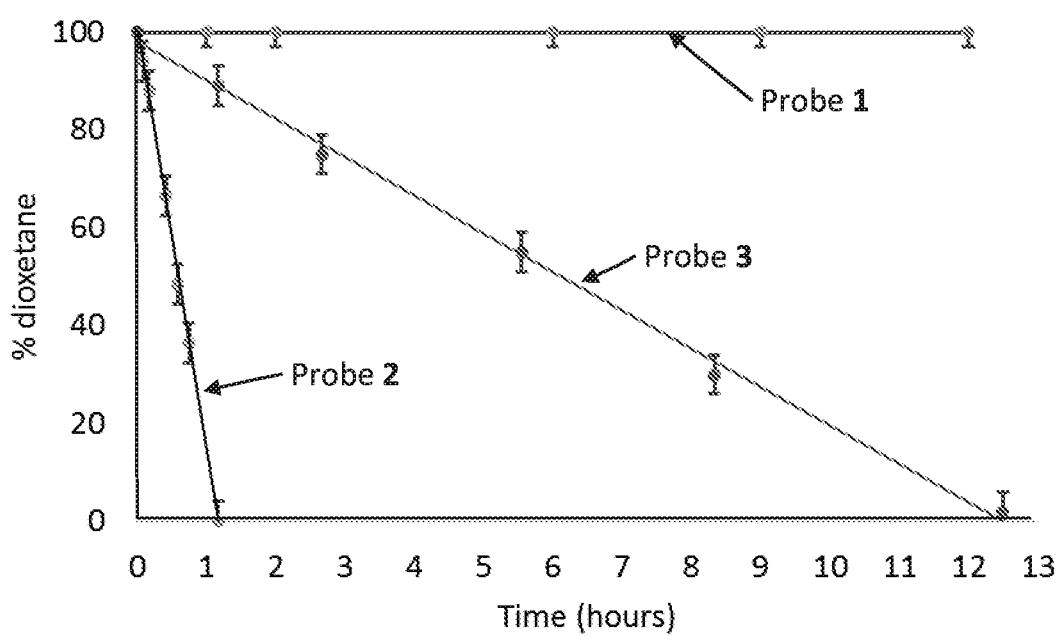
FIG. 2 shows decomposition of Probes 1, 2 and 3 under normal room illumination conditions. Probes (300 μM) were incubated in PBS (100 mM), pH 7.4, at ambient temperature.

Light-induced decomposition of dioxetane-dye conjugates. While working on the synthesis of the dioxetane-fluorophore conjugates, we encountered an unexpected phenomenon. Although Probe 1 seemed to be photostable, Probes 2 and 3 appeared to decompose under normal room illumination conditions. We measured the photostability of the probes in aqueous solution (PBS, pH 7.4) under normal room illumination. The light-induced decomposition was monitored over several hours by a RP-HPLC assay (FIG. 2).

Figure 3:
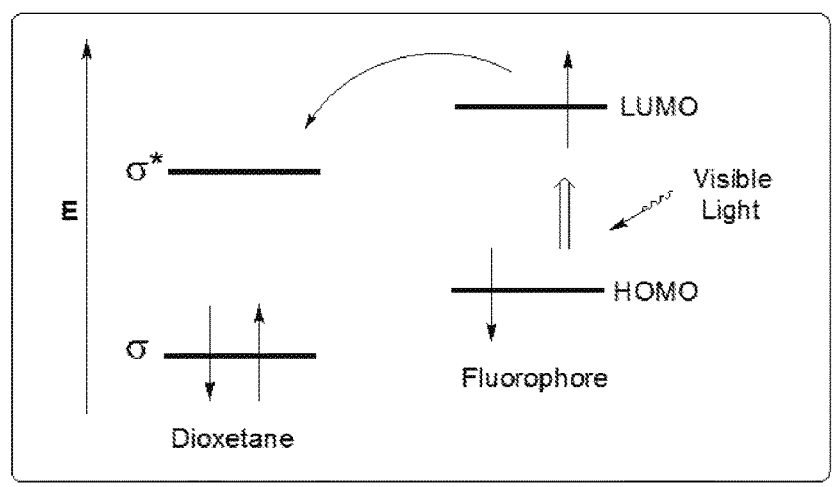
FIG. 3 illustrates a proposed pathway for visible-light-induced decomposition of dioxetane-fluorophore conjugates.
Figure 3:
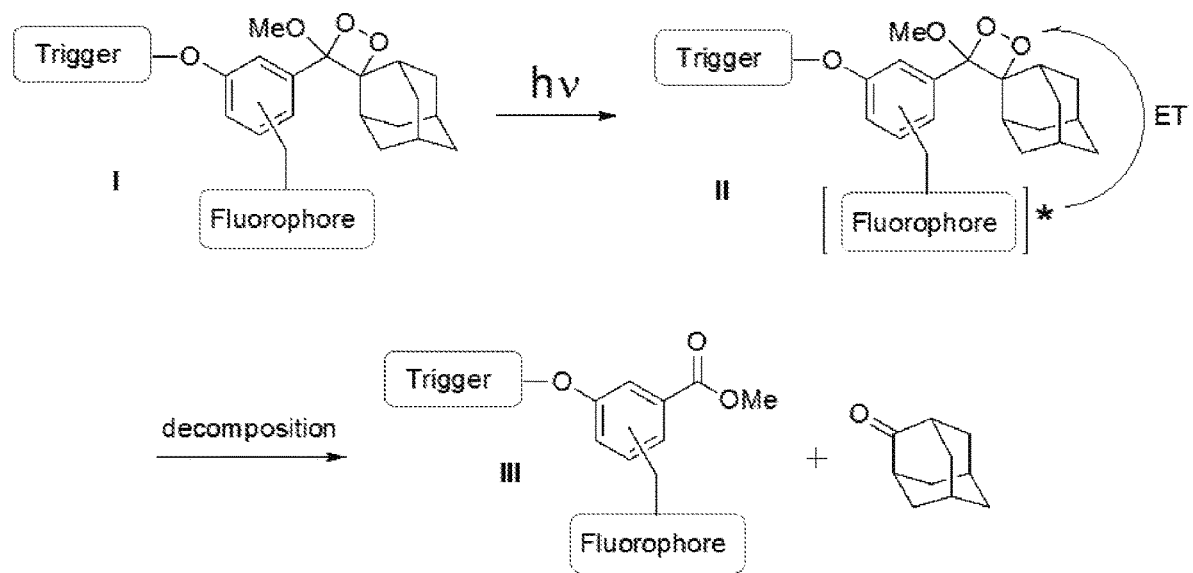

Probe 1 was unaffected by light over a 12 h period. Probe 3 exhibited significantly higher photostability than Probe 2. The light-induced decomposition half-life of Probe 2 was 45 min, whereas the half-life of Probe 3 was about 6 h. No decomposition of any of the probes was observed when the solutions were kept in the dark. A possible mechanism for lightinduced decomposition of the dioxetane-fluorophore conjugates might involve electron transfer from the excited dye to the peroxy-dioxetane bond (Wakimoto et al., 2015). FIG. 3 illustrates a possible light-induced decomposition mechanism. The fluorophore of conjugate I is excited by visible light to form excited species II. Electron transfer from the LUMO of the excited fluorophore to the antibonding 6* orbital of 0-0 peroxide bond results in bond cleavage and subsequent decomposition of the dioxetane into benzoate III and adamantanone. The observed light instability of Probes 2 and 3 underlines the advantage of our late-stage functionalization strategy over previous reported synthetic methods for dioxetane-fluorophore conjugates. The oxidation of the enol ether to the dioxetane is usually performed by singlet oxygen generated from oxygen by a light source and a photosensitizer. Such conditions, 1f applied after the conjugation of the fluorophore, could lead to decomposition of the dioxetane. We were able to avoid light-induced decomposition by using late-stage functionalization chemistry that allows attachment of the fluorophore only after preparation of the dioxetane.

Figure 4:
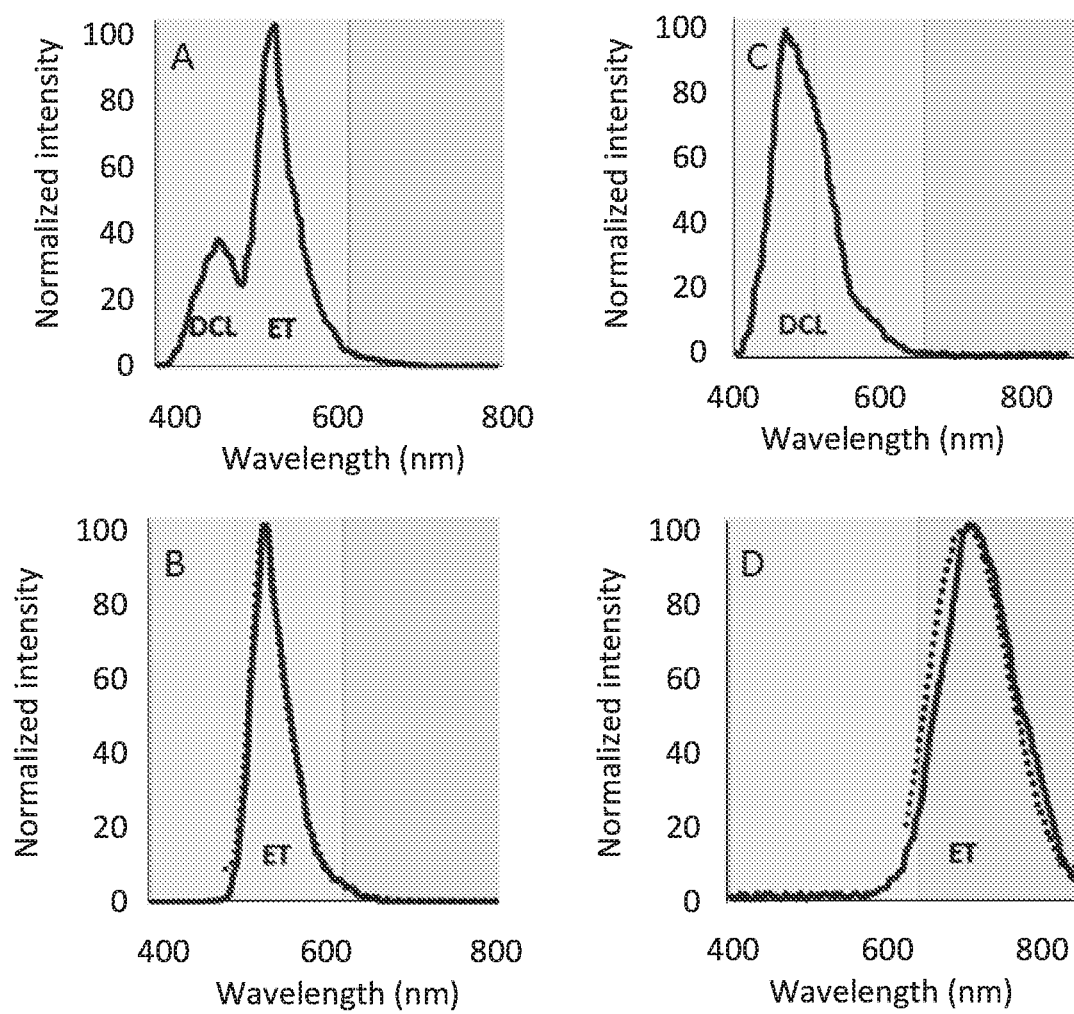
FIG. 4 shows chemiluminescence emission spectra of 1 μM (panel A) 1:1 mixture of Probe 1 and fluorescein derivative 2b, $\lambda_{max}$=470 nm, 535 nm; (panel B) Probe 2, $\lambda_{max}$=535 nm; (panel C) 1:1 mixture of Probe 1 and QCy derivative 3b, $\lambda_{max}$=470 nm; and (panel D) Probe 3,$\lambda_{max}$=714 nm. Spectra were recorded in PBS (100 mM), pH 7.4, in the presence of 1.5 units/mL β-galactosidase (continuous lines). Dotted line is the fluorescence emission spectrum (DCL—direct chemiluminescence).

Energy transfer observed for dioxetane-dye conjugate vs. a mixture of dioxetane and a dye. We first wanted to evaluate the efficiency of energy transfer in the dioxetane-fluorophore conjugates in comparison to a 1:1 mixture of Probe 1 and a dye, upon activation with β-galactosidase. The obtained chemiluminescence emission spectra are shown in FIG. 4. In the case of fluorescein, two emission maxima were obtained for the dioxetane-dye mixture (FIG. 4, panel A) at wavelengths of 470 and 535 nm. These wavelengths correspond to the direct chemiluminescence of Probe 1 and to the emission of fluorescein resulting from energy transfer, respectively. On the other hand, Probe 2 (dioxetane-fluorescein conjugate), upon activation by β-galactosidase, decomposed to emit greenish light with maximum emission wavelength of 535 nm exclusively (FIG. 4, panel B). The observed chemiluminescence spectrum of the probe was almost identical to its fluorescence spectrum (dotted line); indicating a complete energy transfer to the fluorescein acceptor. In the case of QCy, only blue emission with maximum wavelength of 470 nm was obtained for the dioxetane-dye mixture (FIG. 4, panel C). This emission corresponds to the direct chemiluminescence of Probe 1. On the other hand, Probe 3 (QCy-tethered dioxetane) decomposed to emit NIR light with maximum emission wavelength of 714 nm (FIG. 4, panel D). Similarly, as observed for Probe 2, the chemiluminescence spectrum of Probe 3 was found to be almost identical to its fluorescence spectrum (dotted line). This observation clearly supports the energy transfer mechanism illustrated in Scheme 8, and properly demonstrates the significance of covalent conjugation between the dioxetane and the dye.

Figure 5:
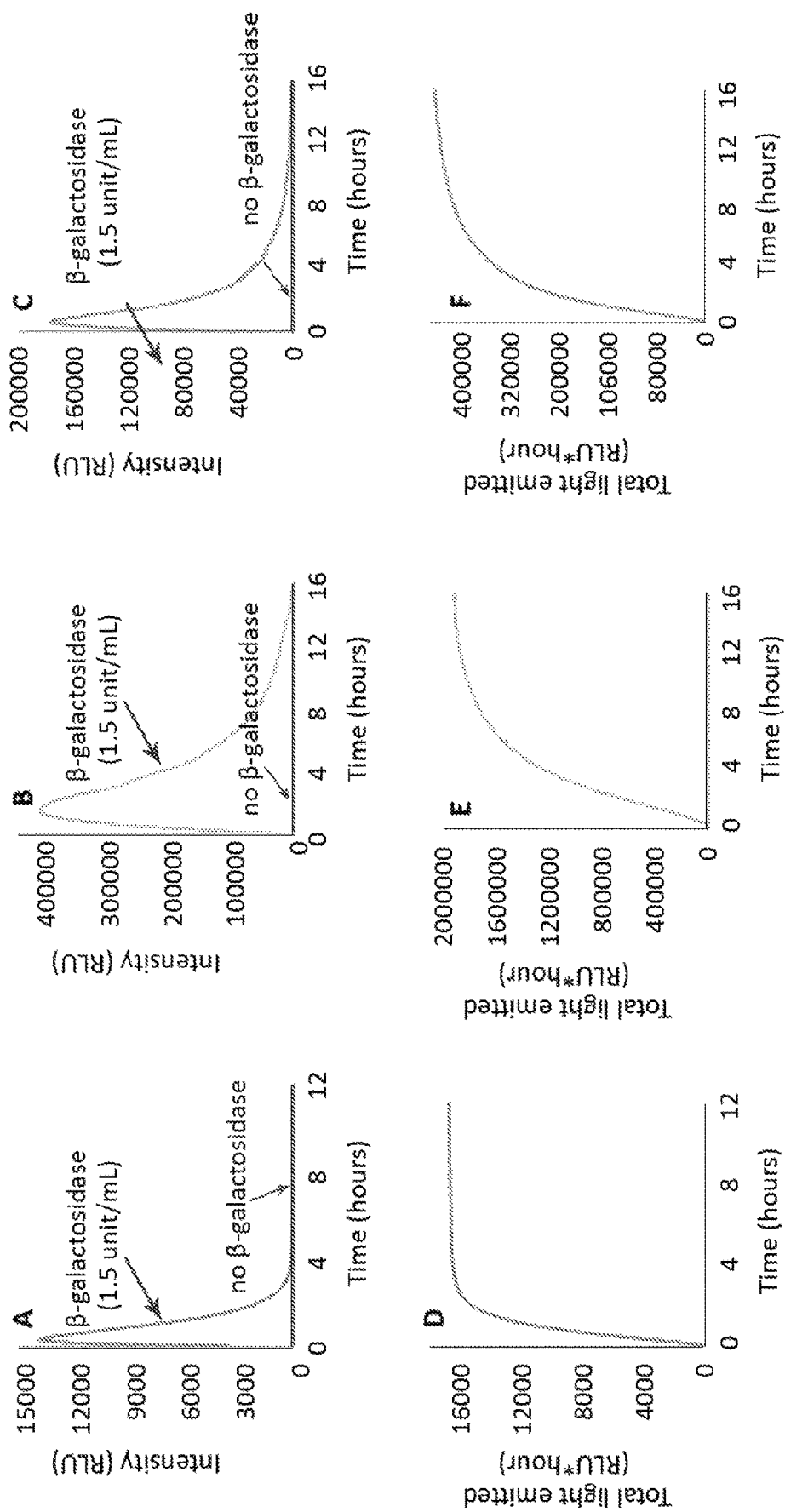
FIG. 5 shows (panels A-C) chemiluminescent kinetic profiles of 1 μM (A) Probe 1, (B) Probe 2, and (C) Probe 3 in PBS (100 mM), pH 7.4, in the presence of 1.5 units/mL β-galactosidase and in the absence of β-galactosidase. Panels D-F show total photon counts emitted from (D) Probe 1, (E) Probe 2, and (F) Probe 3 in the presence of β-galactosidase.

Chemiluminescence parameters measured for Probes 1, 2 and 3 and their ability to detect and image β-galactosidase. Next, we measured the light emission of the probes, as a function of time, in the presence and in the absence of β-galactosidase. The probes exhibited a typical chemiluminescent kinetic profile in the presence β-galactosidase with an initial signal increase to a maximum followed by a slow decrease to zero (FIG. 5, panels A-C). No light emission was observed from the probes in the absence of β-galactosidase. FIG. 5, panels D-F, show the total photon counts emitted from each of the probes. The measured chemiluminescence parameters obtained for Probes 1, 2 and 3 are summarized in Table 8.

The chemiluminescence quantum yield ($\phi_{CL}$) of probes 2 and 3 was calculated using that of Probe 1 as a known standard (Edwards et al., 1994). Probes 2 and 3 exhibited significantly higher light emission than the emission exhibited by Probe 1 (114-fold for Probe 2 and 27-fold for Probe 3). In addition, Probes 2 and 3 had longer half-lives of light emission under identical conditions.

TABLE 8

Chemiluminescent parameters obtained for Probes 1-3

| Probe | $\lambda_{max}$ [nm] | $T_{1/2}$ [min] | $\Phi_{CL}$ | Relative $\Phi_{CL}$ |
|---|---|---|---|---|
| 1 | 470 | 40 | $3.3 \times 10^{-5}$ | 1 |
| 2 | 535 | 170 | $3.8 \times 10^{-3}$ | 114 |
| 3 | 714 | 100 | $9.0 \times 10^{-4}$ | 27.2 |

Figure 6:
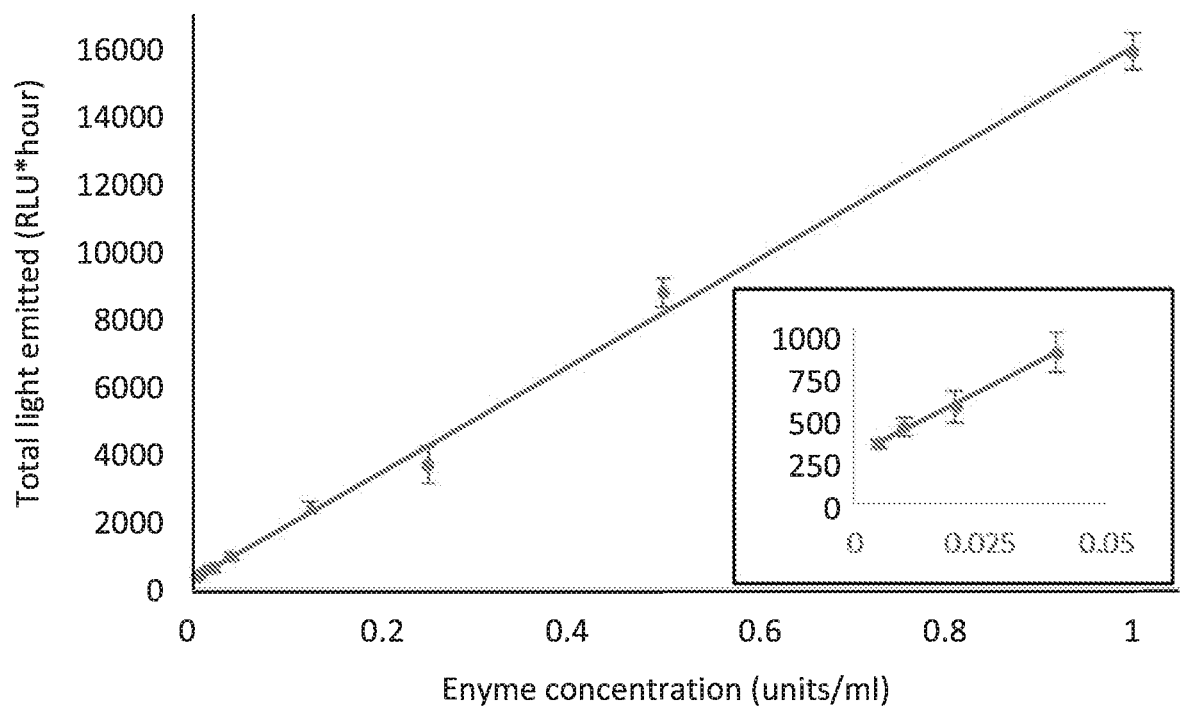
FIG. 6 shows total light emitted from 10 μM Probe 2 in PBS (100 mM), pH 7.4, over a period of 1 h, with different concentrations of β-galactosidase. The inset focuses on light emitted from Probe 2 upon incubation with the lowest concentrations of β-galactosidase.

Probe 2 exhibited brighter chemiluminescence than the other probes since its energy transfer is resulted with an excited fluorescein species (a dye with 90% fluorescence quantum yield). We therefore selected Probe 2 and demonstrated its ability to detect β-galactosidase (FIG. 6). The probe was incubated with different concentrations of β-galactosidase and total chemiluminescence emission was collected over 1 h period. Linear correlation was observed between enzyme concentrations and integrated chemiluminescence signal, enabling quantification of enzyme concentration. We determined a detection limit (blank control+3 SD) of $4.0 \times 10^{-3}$ units/mL.

Figure 7A:
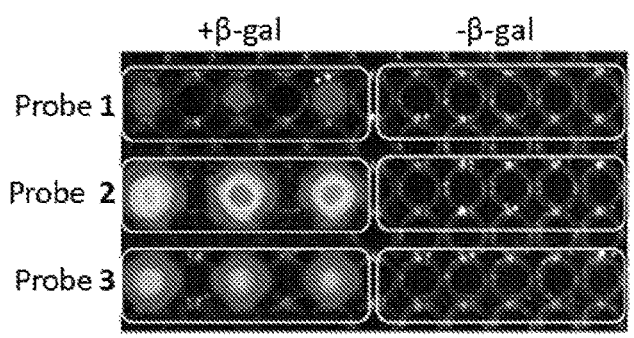
FIGS. 7A-7D show (7A) solution images obtained from 1 μM Probes 1, 2 and 3 incubated in PBS, pH 7.4, in the presence and in the absence of β-galactosidase (gal); (7B) quantification of signal intensities obtained in solution in the presence of β-galactosidase; (7C) whole-body images obtained 15 min following subcutaneous injection of Probes 2 and 3 [50 μL, 1 μM in PBS (100 mM), pH 7.4, after 30 min pre-incubation with or without 1.5 units/mL β-galactosidase]; and (7D) quantification of signal intensities in whole-body images in the presence of β-galactosidase (quantitative data are based on repeated imaging experiments with three mice).
Figure 7B:
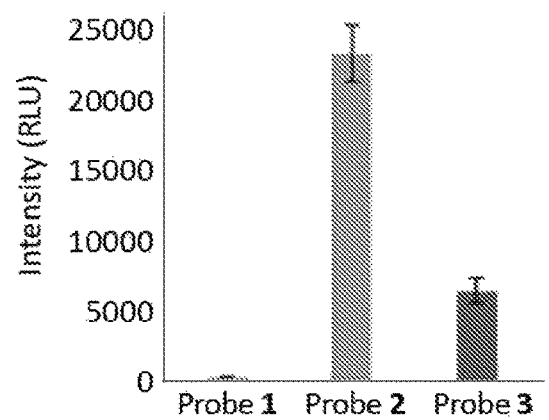
Figure 7C:
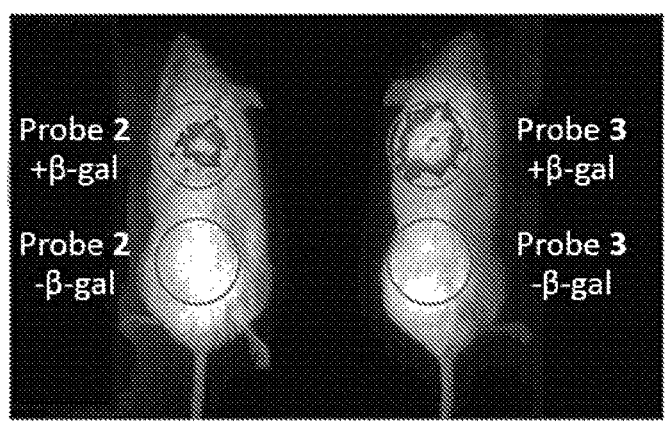
Figure 7D:
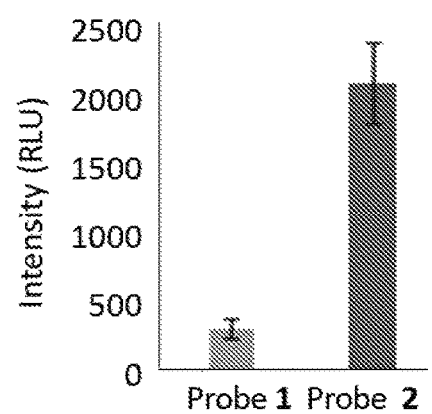

The ability of Probes 2 and 3 to image β-galactosidase activity was initially evaluated in aqueous solution (PBS, pH 7.4) using Probe 1 as a control (FIG. 7A). In the absence of β-galactosidase, no chemiluminescence was observed from any of the probes; however, in the presence of the enzyme, Probes 2 and 3 emitted light with much stronger intensity than that of Probe 1 (about 100-fold for Probe 2 and 25-fold for Probe 3, FIG. 7B). Probes 2 and 3 were selected for further evaluation in vivo; notably, Probe 3 emits light within the NIR region. This region of light is optimal for in vivo imaging applications since NIR photons penetrate organic tissues (Weissleder, 2001; Gnaim and Shabat 2014; Kisin-Finfer et al., 2014; Redy-Keisar et al., 2014; Redy-Keisar et al., 2015a-b). Probes 2 and 3 were incubated with β-galactosidase and then injected subcutaneously to mice. Under such conditions, clear chemiluminescence images were obtained for both probes (FIG. 7C); however, the signal intensity obtained from Probe 3 was about 6-fold higher than that obtained from Probe 2 (FIG. 7D). No chemiluminescence signal was obtained from the probes without preincubation with β-galactosidase.

Figure 8:
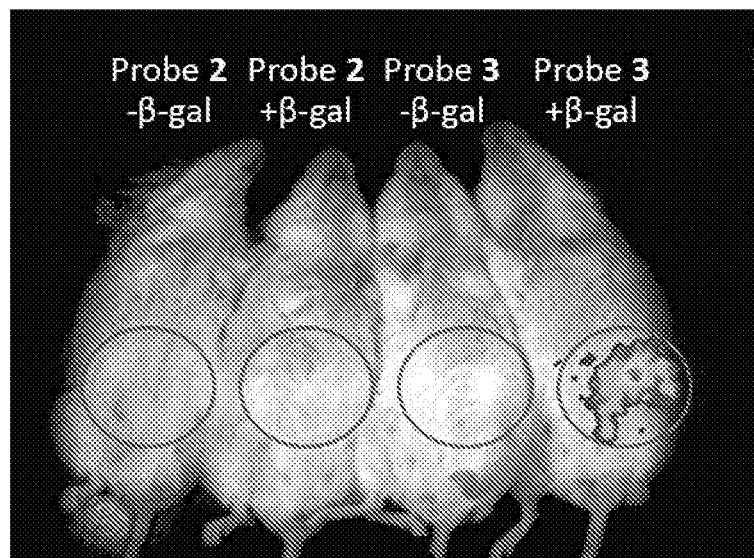
FIG. 8 shows whole-body images obtained 15 min following intraperitoneal injection of Probes 2 and 3 [50 μL, 1 μM in PBS (100 mM), pH 7.4, after a 30 min pre-incubation with or without 1.5 units/mL β-galactosidase].

In order to further compare the in vivo chemiluminescence signals of Probes 2 and 3, the probes (with and without ex vivo incubation with β-galactosidase) were injected into mice via the intraperitoneal route. Remarkably, Probe 3 produced a strong chemiluminescence in vivo image, whereas no chemiluminescence signal was observed for Probe 2 (FIG. 8). These observations clearly demonstrate the in vivo imaging advantage of the NIR chemiluminescence produced by Probe 3 vs. that of the green wavelength produced by Probe 2.

In previous examples that used Schaap's dioxetanes for in vivo imaging (Cao et al., 2015; Cao et al., 2016; Liu and Mason, 2010), a surfactant-dye adduct (Emerald-II enhancer) was added to the injected solution in order to allow detection of the chemiluminescence signal. The use of multi-component system for in vivo imaging has its obvious limitations, especially when the animal is treated systemically. As we demonstrated in FIG. 8, bright image was obtained from the QCy-tethered dioxetane (Probe 3), following ex vivo activation with β-galactosidase and intraperitoneal injection into mice. Here we established the proof of concept of the dioxetane-fluorophore conjugates to act as turn-ON chemiluminescent probes for in vivo imaging. In the next step, we intend to study the capability of the probes to image real pathological events, such as cancer and inflammation. Yet, to demonstrate imaging based on real endogenous activity, we next sought to image cells that endogenously overexpressed β-galactosidase.

Figure 9:
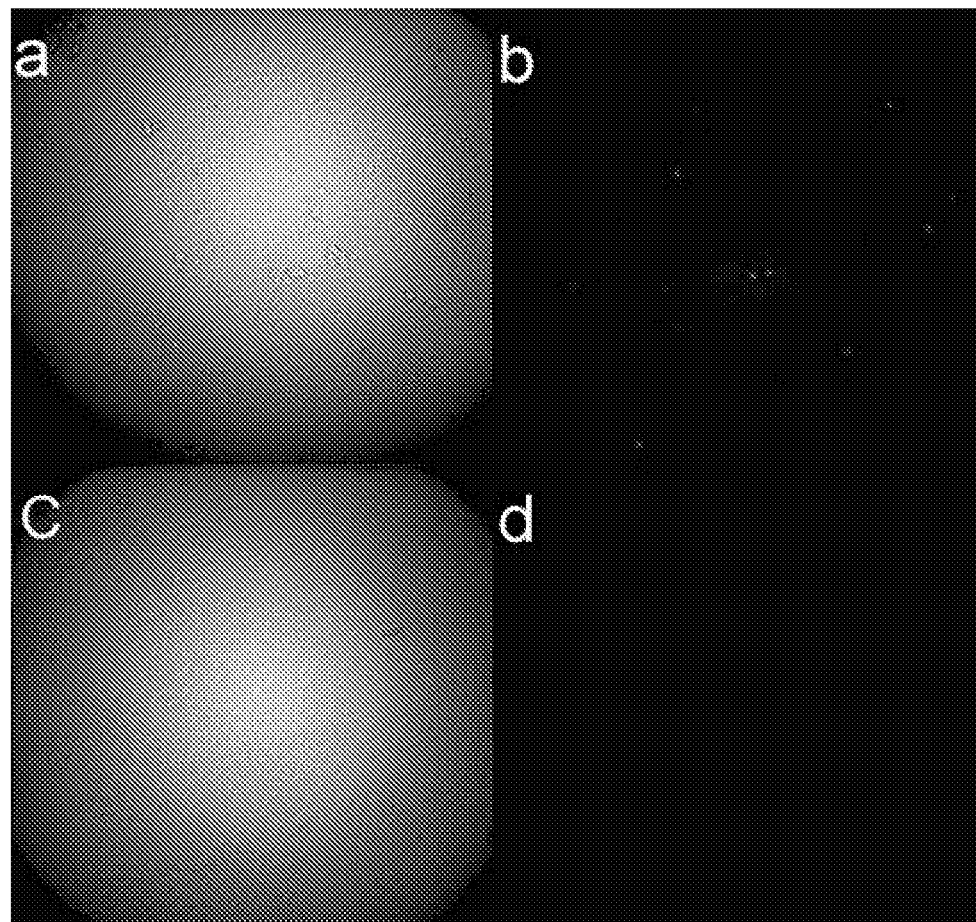
FIG. 9 shows transmitted light image (panel a) and chemiluminescence microscopy of HEK293-LacZ stable cells (panel b); and transmitted light image (panel c) and chemiluminescence microscopy of HEK293-WT cells (panel d). Images were obtained following 20 min incubation with cell culture medium containing Probe 3 (5 μM).

Cell imaging using chemiluminescence microscopy by Probe 3. While fluorescence microscopy is a well-known established method for cell imaging, bioluminescence microscopy has recently been emerged (Bauer, 2013). Instrumentation improvements led to the development of the LV200 microscope by Olympus. The setup of this microscope has significantly improved the ability to localize and quantify luminescence probes at single cell resolution. So far, only luciferin was demonstrated as a probe to image cells transfected by the luciferase gene. We sought to evaluate the ability of Probe 3 to image cells with overexpression of β-galactosidase by using the LV200 microscope. HEK293 (transfected by LacZ) and HEK293-WT (control) cells were incubated with Probe 3 and then imaged by the LV200 (FIG. 9) using a 20× objective (NA 0.75). Probe 3 was able to produce chemiluminescence images of the HEK293-LacZ cells (FIG. 9, panel b), while no chemiluminescence signal at all was observed by the HEK293-WT cells (FIG. 9, panel d).

Figure 10:
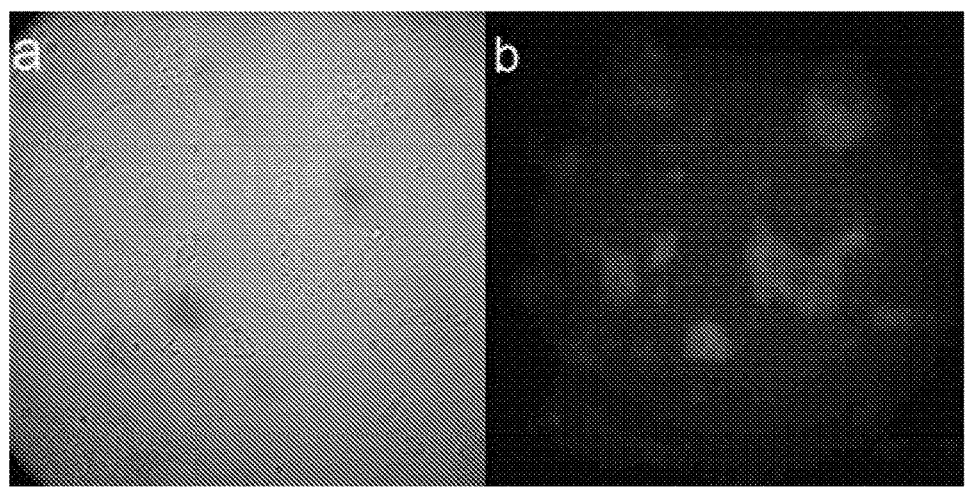
FIG. 10 shows transmitted light image (panel a) and chemiluminescence microscopy of HEK293-LacZ stable cells, fixed with formaldehyde (4% for 20 min) (panel b). Images were obtained following 20 min incubation with cell culture medium containing Probe 3 (5 μM).

To improve the image quality, the HEK293-LacZ cells were fixed by using 4% formaldehyde and permeabilized with 0.1% Triton X-100. The cells were then incubated with Probe 3 and imaged by the microscope using a 60× objective (NA 1.42). As can be seen in FIG. 10 (panel a, transmitted light; panel b, chemiluminescence), the cells became visible, exhibiting a clear chemiluminescence emission.

Although the quality of the obtained images is not high yet, as far as we know, these are the first chemiluminescence cell images produced by a turn-ON small-molecule probe that is not related to luciferin. This approach should allow imaging other enzymatic/chemical reactivities in cells by replacing the triggering group of the probe with the appropriate analyteresponsive substrates. The synthetic strategy developed in this work enables convenient synthesis of various chemiluminescence probes. For example, a lipase or an esterase probe can be prepared by incorporation of an appropriate ester triggering group instead of the β-galactose one. Similarly, the synthesis of proteases probes can be achieved by using a short specific peptide as triggering substrate. Of course, incorporation of certain substrates could be more challenging than others; however, the use of orthogonal protecting groups should assist in solving synthetic difficulties.

CONCLUSIONS

In summary, we have developed a simple and practical synthetic route for preparation of turn-ON fluorophore-tethered dioxetane chemiluminescent probes. The effectiveness of the synthesis is based on a late-stage functionalization of a dioxetane precursor by Hartwig-Miyaura C—H borylation, followed by subsequent Suzuki coupling and oxidation to dioxetane. The obtained intermediate is composed of a reactive NHS-ester-dioxetane ready for conjugation with any fluorophore-amine derivative. We also reported the phenomenon of light-induced decomposition of dioxetane-fluorophore conjugates, which highlights the advantage of our synthetic method. The chemiluminescent emission of the fluorophoretethered dioxetane probes was significantly amplified in comparison to a classic dioxetane probe through an energytransfer mechanism. The synthesized probes produced light of various colors that matched the emission wavelength of the excited tethered fluorophore. Using our synthetic route, we synthesized two fluorophore-tethered dioxetane probes designed for activation by β-galactosidase and conjugated with green (fluorescein) and NIR (QCy) fluorescent dyes. Both probes were able to provide chemiluminescence in vivo images following subcutaneous injection after activation by β-galactosidase. However, a chemiluminescence image following intraperitoneal injection was observed only by the NIR probe. These are the first in vivo images produced by Schaap's dioxetane-based chemiluminescence probes with no need of any additive.

The NIR probe was also able to image cells, by chemiluminescence microscopy, based on endogenous activity of β-galactosidase. Such probes could be used for in vivo imaging of reporter genes, enzymes, and chemical analytes. We anticipate that our practical synthetic methodology for dioxetane-tethered building blocks will be useful for preparation of various chemiluminescent probes suitable for numerous applications.

Study 2. Chemiluminescence Cell Imaging by a Non-Luciferin Based Small-Molecule Probe: Striking Substituent Effect on the Emissive Species Experimental General. All reactions requiring anhydrous conditions were performed under an argon atmosphere. All reactions were carried out at RT unless stated otherwise. Chemicals and solvents were either A. R. grade or purified by standard techniques. TLC: silica gel plates Merck 60 F254: compounds were visualized by irradiation with UV light. Column chromatography: silica gel Merck 60 (particle size 0.040-0.063 mm), eluent given in parentheses. RP-HPLC: C18 5u, 250×4.6 mm, eluent given in parentheses. Preparative RP-HPLC: C18 5u, 250×21 mm, eluent given in parentheses. $^1$H-NMR spectra were recorded using Bruker Avance operated at 400 MHz. $^{13}$C-NMR spectra were recorded using Bruker Avance operated at 100 MHz. Chemical shifts were reported in ppm on the δ scale relative to a residual solvent (CDCl$_3$: δ=7.26 for $^1$H-NMR and 77.16 for $^{13}$C-NMR, DMSO-d$_6$: δ=2.50 for $^1$H-NMR and 39.52 for $^{13}$C-NMR). Mass spectra were measured on Waters Xevo TQD. Fluorescence and chemiluminescence were recorded on Molecular Devices Spectramax i3×. Fluorescence quantum yield was determined using Hamamatsu Quantaurus-QY. All reagents, including salts and solvents, were purchased from Sigma-Aldrich.

Benzoate 5a. 2-Chloro-3-hydroxybenzaldehyde (1a, 312 mg, 2 mmol) was dissolved in McOH (5 mL). Oxone (615 mg, 2 mmol) and In(OTf)$_3$ (112 mg, 0.22 mmol) were added at RT. The reaction mixture was heated to reflux and monitored by RP-HPLC. After the reaction was completed the mixture was filtered and the filtrate was concentrated using a rotary evaporator. Purification by column chromatography (Hex:EtOAc 30:70) afforded benzoate 5a as a white solid (339 mg, 92% yield). $^1$H NMR (400 MHz, CDCl$_3$) δ 7.44 (dd, J=7.5, 1.8 Hz, 1H), 7.24 (t, J=7.5 Hz, 1H), 7.18 (dd, J=8.1, 1.8 Hz, 1H), 6.08 (s, 1H), 3.93 (s, 3H). $^{13}$C NMR (101 MHz, CDCl$_3$) δ 166.11, 152.59, 130.27, 127.87, 123.60, 119.74, 52.82. MS (ES-): m/z calc. for C$_8$H$_7$ClO$_3$:186.0; found: 185.0 [M−H]$^-$.

Compound 4b. To a stirred solution of benzoate 4a (1.52 g, 10 mmol) in EtOH (4 mL) was added I2 (1.02 g, 4 mmol) in one portion. The reaction was heated to reflux before an aqueous solution (2 mL) of HIO$_3$ (352 Ong. 2 mmol) was added. The mixture was refluxed for 1 hour before it was cooled to RT. The product was recovered by filtration and washed with water to give compound 4b as a white solid. (2.11 g, 76% yield). $^1$H NMR (400 MHz, CDCl$_3$) δ 7.75 (d, J=8.2 Hz, 1H), 7.47 (d, J=1.9 Hz, 1H), 7.24 (dd, J=8.2, 1.9 Hz, 1H), 3.88 (s, 3H). $^{13}$C NMR (101 MHz, CDCl$_3$) δ 167.34, 156.30, 139.41, 131.76, 122.61, 115.64, 91.51, 52.74. MS (ES-): m/z calc. for C$_8$H$_7$ClIO$_3$:277.9; found: 276.9 [M−H]$^-$.

Compound 4c. A mixture of compound 4b (1.39 g, 5 mmol) and TEMP (1.52 IA 0.05 mmol) in toluene (100 ml) was heated to 100° C. Then, SO$_2$C$_{12}$ (404 pi, 5 minor) dissolved in toluene (50 ml) was added dropwise. The mixture was stirred at 100° C. for 1 hour. Upon completion, the reaction was cooled to RI and the product was recovered by filtration and washed with toluene to give compound 4c as a white solid (1.12 g, 72% yield). $^1$H NMR (400 MHz, CDCl$_3$) δ 7.69 (d, J=8.3 Hz, 1H), 7.18 (d, J=8.3 Hz, 1H), 6.48 (s, 1H), 3.92 (s, 3H). $^{13}$C NMR (101 MHz, CDCl$_3$) δ 165.57, 152.17, 137.40, 130.52, 124.47, 118.97, 88.07, 52.98. MS (ES-): m/z calc. for C$_8$H$_6$ClIO$_3$:311.9; found: 310.9 [M−H]$^-$.

Scheme 11: Synthesis of compounds 4b and 4c

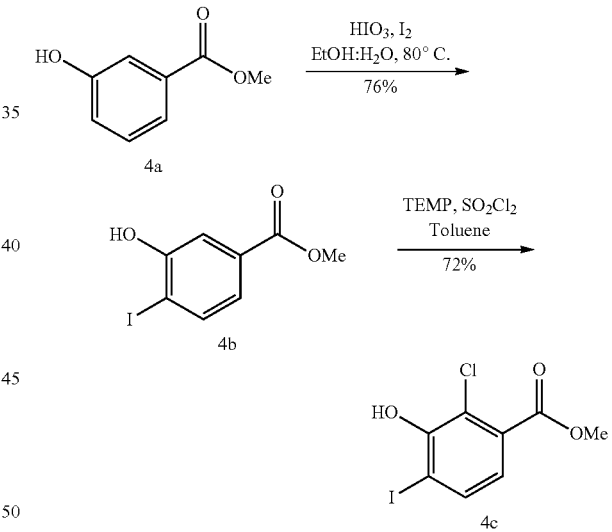

Scheme 10: Synthesis of benzoate 5a

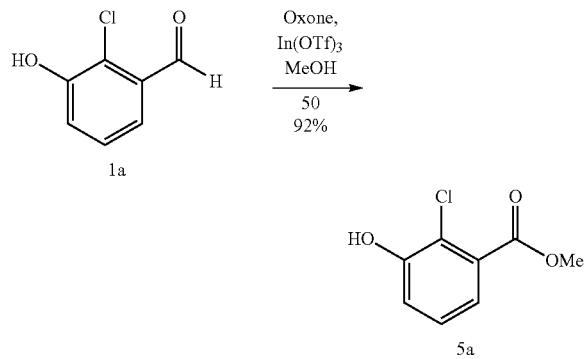

General procedure: Heck reaction of iodophenols with methyl acrylate (benzoates 6a and 7a). Iodophenol (1eq), methyl acrylate (3eq) and Et$_3$N (4.2eq) were dissolved in anhydrous ACN. Then Pd(OAc)$_2$ (0.05eq) and P(o-tol)$_3$ (0.01eq) were added. The flask was sealed and the solution was stirred at 120° C. Reaction was monitored by TLC (Hex:EtOAc 80:20). Upon completion, reaction mixture was diluted with EtOAc and washed with saturated NH$_4$Cl. The organic phase was dried over Na$_2$SO$_4$ and concentrated under reduced pressure. The residue was purified by column chromatography on silica gel (Hex:EtOAc 85:15) to afford the corresponding phenol acrylate.

Benzoate 6a. Compound 4b (200 mg, 0.72 mmol) was reacted according to general procedure. The product was obtained as a white solid (130 mg, 77% yield). $^1$H NMR (400 MHz, CDCl$_3$) δ 7.90 (d, J=16.2 Hz, 1H), 7.46-7.34 (m, 3H), 6.60 (d, J=16.2 Hz, 1H), 3.83 (s, 3H), 3.78 (s, 3H). $^{13}$C NMR (101 MHz, CDCl$_3$) δ 165.66, 149.22, 130.74, 130.17, 129.71, 127.97, 125.27, 123.11, 121.36, 119.82, 52.99. MS (ES-): m/z calc. for C$_{12}$H$_{12}$O$_5$: 236.1; found: 235.1 [M–H]$^-$.

Benzoate 7a. Compound 4c (200 mg, 0.64 mmol) was reacted according to general procedure. The product was obtained as a white solid (115 mg, 67% yield). $^1$H NMR (400 MHz, CDCl$_3$) δ 7.91 (d, J=16.2 Hz, 1H), 7.38 (d, J=8.2 Hz, 1H), 7.33 (d, J=8.2 Hz, 1H), 6.57 (d, J=16.2 Hz, 1H), 3.87 (d, J=0.5 Hz, 3H), 3.71 (s, 3H). $^{13}$C NMR (101 MHz, CDCl$_3$) δ 167.51, 165.49, 151.22, 142.50, 138.57, 130.25, 126.93, 126.60, 123.18, 122.04, 52.95, 52.19. MS (ES-): m/z calc. for C$_{12}$H$_{11}$ClO$_5$: 270.0; found: 269.1 [M–H]$^-$.

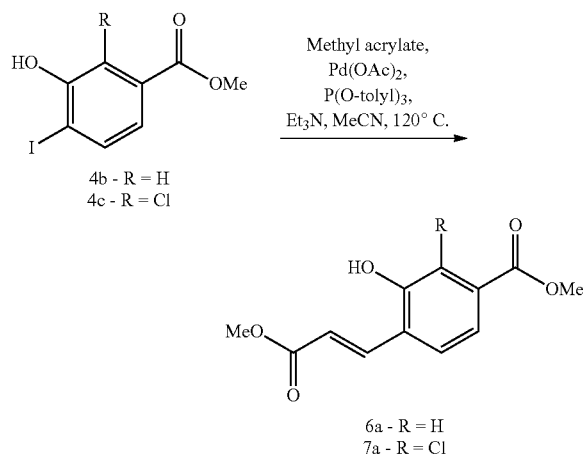

Scheme 12: Synthesis of benzoates 6a and 7a

General procedure: Heck reaction of iodophenols with acrylonitrile (benzoates 8a and 9a). Iodophenol (1eq), acrylonitrile (3eq) and Et$_3$N (1.5eq) were dissolved in anhydrous ACN. Then Pd(OAc)$_2$ (0.05eq) was added and the flask was sealed. The mixture was heated to 120° C. under microwave irradiation. Reaction was monitored by TLC (Hex:EtOAc 80:20). Upon completion, reaction mixture was diluted with EtOAc and washed with saturated NH$_4$Cl. The organic phase was dried over Na$_2$SO$_4$ and concentrated under reduced pressure. The residue was purified by column chromatography on silica gel (Hex:EtOAc 80:20) to afford the corresponding phenol acrylate.

Benzoate 8a. Compound 4b (200 mg, 0.72 mmol) was reacted according to general procedure. The product was obtained as a white solid (118 mg, 81% yield). $^1$H NMR (400 MHz, CDCl$_3$) δ 7.55 (d, J=16.7 Hz, 1H), 7.45 (dd, J=8.1, 1.5 Hz, 1H), 7.42 Scheme 12: Synthesis of benzoates 6a and 7a Methyl acrylate, (d,1.5 Hz 1H), 7.32 (d, J=8.1 Hz, 1H), 6.27 (d, J=16.7 Hz, 1H), 3.87 (s, 3H). $^{13}$C NMR (101 MHz, MeOD) δ 165.04, 155.39, 144.50, 131.48, 127.72, 123.59, 118.79, 117.04, 115.07, 96.86, 50.13. MS (ES-): m/z calc. for C$_{11}$H$_9$O$_5$: 203.1; found: 202.1 [M–H]$^-$.

Benzoate 9a. Compound 4c (200 mg, 0.64 mmol) was reacted according to the general procedure. The product was obtained as a white solid (1.04 mg, 69% yield). $^1$H NMR (400 MHz, MeOD) δ 7.69 (d, J=16.8 Hz, 1H), 7.49 (d, J=8.2 Hz, 1H), 7.28 (d, J=8.2 Hz, 1H), 6.41 (d, J=16.8 Hz, 1H), 3.90 (s, 1H). $^{13}$C NMR (101 MHz, MeOD) δ 166.15, 152.77, 145.25, 132.97, 126.46, 125.62, 121.47, 120.67, 118.23, 99.40, 52.00. MS (ES-): m/z calc. for C$_{11}$H$_8$ClNO$_3$: 237.0; found: 236.0 [M–H]$^-$.

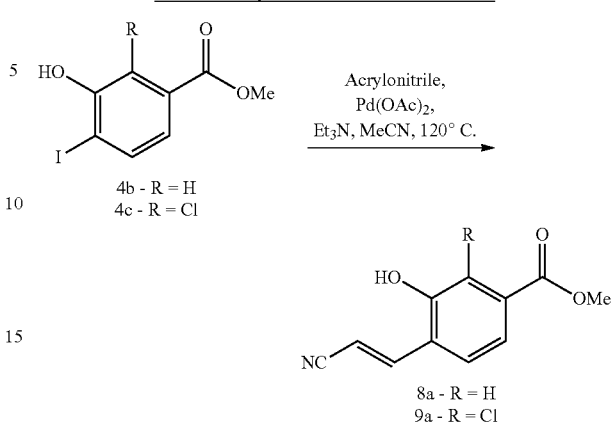

Scheme 13: Synthesis of benzoates 8a and 9a

Compound 4e. 3-Hydroxybenzaldehyde dimethyl acetal 4d (Gopinath et al., 2002) (2580 mg, 15.36 mmol) and imidazole (1568 mg, 23.04 mmol) were dissolved in 15 ml of DCM. TBSCl (2764 mg, 18.42 mmol) was added and the solution was stirred for 30 minutes at RT and monitored by TLC. Upon completion, the white precipitate was filtered-off and the solvent was evaporated under reduced pressure. Purification by column chromatography (Hex:EtOAc 95:5) afforded compound 4e as a colorless oil (4070 mg, 94% yield). $^1$H NMR (400 MHz, CDCl$_3$): δ 7.26 (t, J=7.8 Hz, 1H), 7.04 (d, J=7.6 Hz, 1H), 6.94 (t, J=2.0 Hz, 1H), 6.80 (dd, J=8.1, 2.3 Hz, 1H), 5.34 (s, 1H), 3.32 (s, 6H), 0.99 (s, 9H), 0.20 (s, 6H). $^{13}$C NMR (100 MHz, CDCl$_3$): δ 155.73, 139.71, 129.30, 120.22, 119.85, 118.58, 102.94, 52.74, 25.81, 18.32, –4.30.

Compound 4f. Acetal 4e (4070 mg, 14.43 mmol) and trimethyl phosphite (2.56 ml, 21.65 mmol) were dissolved in 40 ml of DCM. Reaction mixture was cooled to 0° C. and titanium(IV) chloride (2.38 ml, 21.65 mmol) was added dropwise. Reaction was monitored by TLC. Upon completion, the solution was poured into a saturated aqueous solution of NaHCO$_3$ (130 ml) at 0° C. After 10 minutes of stirring, 100 ml of DCM was added and the phases were separated. Organic phase was dried over Na$_2$SO$_4$ and concentrated under reduced pressure. Purification by column chromatography (Hex:EtOAc 30:70) afforded compound 4f as a colorless oil (3745 mg, 72% yield). $^1$H NMR (400 MHz, CDCl$_3$): δ 7.21 (t, J=7.8 Hz, 1H), 6.99 (d, J=7.5 Hz, 1H), 6.92 (d, J=1.9 Hz, 1H), 6.80 (d, J=8.1 Hz, 1H), 4.47 (d, J=15.6 Hz, 1H), 3.68 (d, J=10.6 Hz, 3H), 3.64 (d, J=10.5 Hz, 3H), 3.36 (s, 3H), 0.96 (s, 9H), 0.18 (s, 6H). $^{13}$C NMR (100 MHz, CDCl$_3$): δ 155.91, 135.59, 129.57, 121.17, 120.54, 119.67, 80.88, 79.20, 58.66, 53.76, 25.74, 18.29, –4.39. MS (ES+): m/z calc. for C$_{16}$H$_{29}$O$_5$PSi: 360.1; found: 361.1 [M+H]$^+$.

Compound 4g. Phosphonate 4f (3745 mg, 10.38 mmol) was dissolved in 25 ml of anhydrous THF under argon atmosphere at –78° C. LDA (2.0 M in THF, 6 ml, 12 mmol) was added and the solution was stirred for 20 minutes. A solution of 2-adamantanone (1863 mg, 12.46 mmol) in 20 ml of THF was added, and after 15 minutes of stirring at –78° C. reaction was allowed to warm to RT. Reaction was monitored by TLC. Upon completion, reaction mixture was diluted with EtOAc (150 ml) and washed with brine (150 ml). Organic phase was dried over Na$_2$SO$_4$ and concentrated under reduced pressure. Purification by column chromatography (Hex:EtOAc 95:5) afforded compound 4g as a colorless oil (3200 mg, 80% yield). $^1$H NMR (400 MHz, CDCl$_3$): δ 7.09 (t, J=8.0 Hz, 1H), 6.89-6.84 (m, 2H), 3.30 (s, 3H), 3.27 (s, 1H), 2.05 (s, 1H), 1.97-1.65 (m, 12H), 1.04 (s, 9H), 0.23 (s, 6H). $^{13}$C NMR (100 MHz, CDCl$_3$): δ 151.98, 140.24, 136.20, 130.69, 126.69, 126.58, 124.93, 120.30, 56.98, 39.28, 39.14, 38.74, 37.32, 32.96, 29.70, 28.58, 28.43, 25.86, 18.54, −4.28. MS (ES+): m/z calc. for C$_{24}$H$_{35}$ClO$_2$Si: 418.2; found: 419.3 [M+H]$^+$.

Compound 4h. Compound 4g (3200 mg, 8.3 mmol) was dissolved in 30 ml of THF. Tetrabutylammonium fluoride (1.0 M in THF, 9.2 ml, 9.2 mmol) was added and the solution was stirred at RT. Reaction was monitored by TLC. Upon completion, reaction mixture was diluted with EtOAc (150 ml) and washed with 1M HCl (100 ml). Organic phase was dried over Na$_2$SO$_4$ and concentrated under reduced pressure. Purification by column chromatography (Hex:EtOAc 85:15) afforded compound 4h as white solid (2130 mg, 95% yield). $^1$H NMR (400 MHz, CDCl$_3$) δ 7.21 (t, J=7.8 Hz, 1H), 6.88 (d, J=7.5 Hz, 1H), 6.82 (s, 1H), 6.79-6.71 (m, 1H), 5.30 (s, 1H), 3.31 (s, 3H), 3.23 (s, 1H), 2.65 (s, 1H), 2.04-1.69 (m, 12H). $^{13}$C NMR (100 MHz, CDCl$_3$) δ 155.8, 142.8, 136.7, 132.4, 129.1, 121.8, 115.9, 114.6, 57.7, 39.1, 39.0, 37.1, 32.2, 30.3, 28.2 ppm. MS (ES-): m/z calc. for C$_{18}$H$_{22}$O$_2$: 270.2; found: 269.3 [M−H]$^−$.

Compound 4i. Compound 4h (2130 mg, 7.9 mmol) was dissolved in 150 ml of Toluene and cooled to 0° C. N-Iodosuccinimide (1777 mg, 7.9 mmol) was added in portions. Reaction was monitored by TLC. Upon completion, reaction was quenched with saturated Na$_2$S$_2$O$_3$, diluted with EtOAc (250 ml) and washed with brine (200 ml). The organic phase was dried over Na$_2$SO$_4$ and concentrated under reduced pressure. The residue was purified by column chromatography on silica gel (Hex:EtOAc 85:15) to afford compound 4i as a white solid (2439 mg, 78% yield). $^1$H NMR (400 MHz, CDCl$_3$) δ 7.62 (dd, J=8.1, 0.4 Hz, 1H), 6.96 (d, J=1.4 Hz, 1H), 6.65 (ddd, J=8.1, 1.8, 0.5 Hz, 1H), 5.42 (d, J=0.6 Hz, 1H), 3.30 (t, J=2.4 Hz, 3H), 3.22 (s, 1H), 2.63 (s, 1H), 2.00-1.67 (m, 12H). $^{13}$C NMR (101 MHz, CDCl$_3$) δ 154.66, 142.32, 138.02, 137.84, 133.01, 123.68, 115.86, 84.21, 77.42, 77.10, 76.79, 58.01, 39.22, 39.08, 37.16, 32.33, 30.33, 28.29. MS (ES-): m/z calc. for C$_{18}$H$_{21}$IO$_2$: 396.1; found: 395.1 [M−H]$^−$.

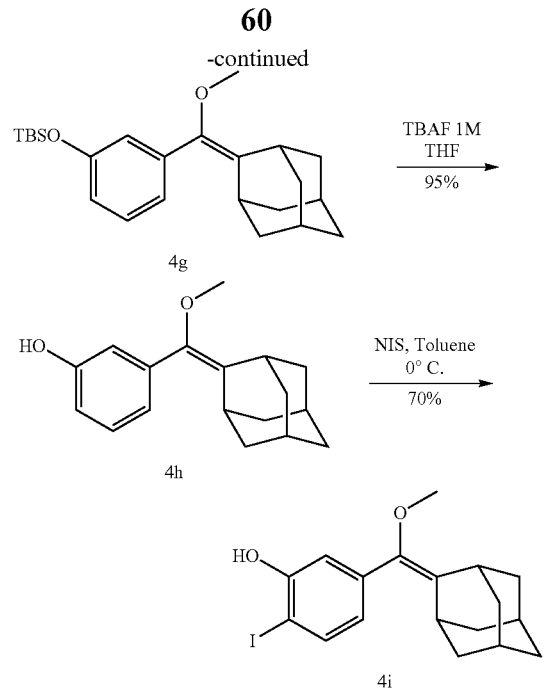

Compound 4j. Compound 1f (2420 mg, 7.9 mmol) was dissolved in 150 ml of toluene and cooled to 0° C. N-Iodosuccinimide (1777 mg, 7.9 mmol) was added in portions. Reaction was monitored by TLC. Upon completion, the solvent was evaporated under reduced pressure. Purification by column chromatography (Hex:EtOAc 80:20) afforded compound 4j as a white solid (1531 mg, 45% yield). $^1$H NMR (400 MHz, CDCl$_3$) δ 7.61 (d, J=8.1 Hz, 1H), 6.62 (d, J=8.1 Hz, 1H), 6.15 (s, 1H), 3.30 (s, 3H), 3.25 (s, 1H), 2.09 (s, 1H), 2.01-1.64 (m, 12H). $^{13}$C NMR (101 MHz, CDCl$_3$) δ 151.17, 139.21, 136.77, 135.75, 132.68, 125.27, 120.05, 82.22, 57.30, 39.10, 38.67, 37.09, 32.91, 29.72, 28.38. MS (ES-): m/z calc. for C$_{18}$H$_{20}$C$_1$IO$_2$: 430.0; found: 429.3 [M−H]$^−$.

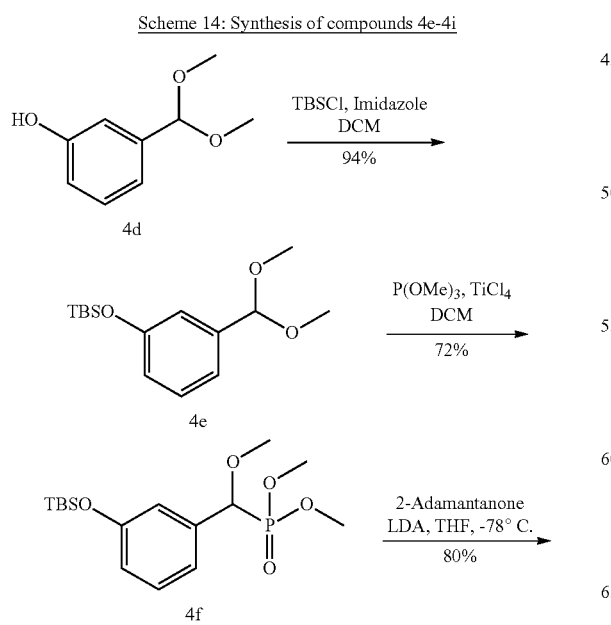

Scheme 14: Synthesis of compounds 4e-4i

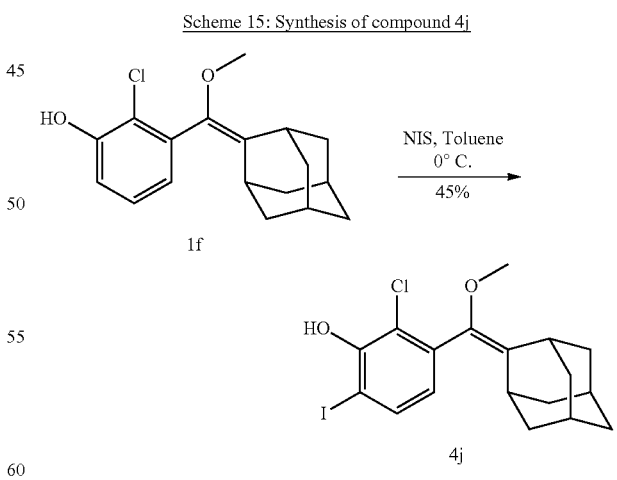

Scheme 15: Synthesis of compound 4j

General procedure: Heck reaction of iodophenols with methyl acrylate (compounds 6c and 7c). Iodophenol (1eq), methyl acrylate (3eq), and Et$_3$N (1.5eq) were dissolved in anhydrous ACN. Then Pd(OAc)$_2$ (0.05eq) and P(o-tol)$_3$ (0.01eq) were added. The flask was sealed and the solution was stirred at 120° C. Reaction was monitored by TLC (Hex:EtOAc 80:20). Upon completion, reaction mixture was diluted with EtOAc and washed with saturated NH$_4$Cl. The organic phase was dried over Na$_2$SO$_4$ and concentrated under reduced pressure. The residue was purified by column chromatography on silica gel (Hex:EtOAc 85:15) to afford the corresponding phenol acrylate.

Compound 6c. Compound 4i (395 mg, 1 mmol) was reacted according to the general method. The product was obtained as a pale yellow solid (248 mg, 70% yield). $^1$H NMR (400 MHz, CDCl$_3$) δ 7.99 (d, J=16.1 Hz, 1H), 7.43 (d, J=8.4 Hz, 1H), 6.95-6.74 (m, 2H), 6.74-6.45 (m, 2H), 3.82 (s, 3H), 3.33 (s, 3H), 3.23 (s, 1H), 2.70 (s, 1H), 2.06-1.72 (m, 12H). $^{13}$C NMR (101 MHz, CDCl$_3$) δ 168.57, 155.44, 142.50, 140.28, 138.92, 134.09, 128.94, 122.22, 121.01, 118.11, 116.70, 58.17, 51.87, 39.30, 39.15, 37.17, 32.45, 30.54, 28.30. MS (ES-): m/z calc. for C$_{22}$H$_{26}$O$_4$: 354.2; found: 353.2 [M-H]$^-$.

Compound 7c. Compound 4j (430 mg, 1 mmol) was reacted according to the general method. The product was obtained as a pale yellow solid (271 mg, 70% yield). $^1$H NMR (400 MHz, CDCl$_3$) δ 7.94 (d, J=16.2 Hz, 1H), 7.38 (d, J=8.0 Hz, 1H), 6.86 (d, J=8.0 Hz, 1H), 6.61 (d, J=16.2 Hz, 1H), 6.28 (s, 1H), 3.84 (s, 3H), 3.35 (s, 3H), 3.27 (d, J=4.9 Hz, 1H), 2.12 (s, 1H), 2.02-1.66 (m, 12H). $^{13}$C NMR (101 MHz, CDCl$_3$) δ 232.43, 206.72, 173.51, 167.74, 150.65, 139.23, 136.60, 132.96, 126.80, 123.82, 123.70, 121.97, 121.54, 119.77, 95.27, 57.41, 51.86, 39.19, 38.89, 37.09, 32.95, 32.03, 29.78, 28.37, 24.44. MS (ES-): m/z calc. for C$_{22}$H$_{25}$ClO$_4$: 388.14; found: 387.4 [M-H]$^-$.

obtained as a pale yellow solid (129 mg, 80% yield). $^1$H NMR (400 MHz, CDCl$_3$) δ 7.81 (s, 1H), 7.61 (d, J=16.7 Hz, 1H), 7.32 (d, J=8.0 Hz, 1H), 7.01 (s, 1H), 6.89 (d, J=7.9 Hz, 1H), 6.22 (d, J=16.7 Hz, 1H), 3.39 (s, 3H), 3.25 (s, 1H), 2.73 (s, 1H), 1.86 (m, J, 12H). $^{13}$C NMR (101 MHz, CDCl$_3$) δ 156.44, 147.09, 142.23, 139.48, 135.29, 129.47, 122.16, 120.55, 119.58, 116.79, 96.71, 77.68, 77.36, 77.05, 58.45, 39.43, 39.29, 37.24, 32.69, 30.84, 29.98, 28.39. MS (ES-): m/z calc. for C$_{21}$H$_{23}$NO$_2$: 321.17; found: 320.2 [M-H]$^-$.

Compound 9c. Compound 4j (200 mg, 0.45 mmol) was reacted according to the general method. The product was obtained as a pale yellow solid (77 mg, 48% yield). $^1$H NMR (400 MHz, CDCl$_3$) δ 7.47 (d, J=16.8 Hz, 1H), 7.16 (d, J=8.0 Hz, 1H), 6.77 (d, J=8.0 Hz, 1H), 6.36 (s, 1H), 6.07 (d, J=16.8 Hz, 1H), 3.20 (s, 3H), 3.15 (s, 1H), 1.99 (s, 1H), 1.90-1.50 (m, 12H). $^{13}$C NMR (101 MHz, CDCl$_3$) δ 150.65, 145.45, 139.19, 137.55, 133.46, 126.82, 123.84, 121.80, 121.12, 118.66, 98.63, 77.48, 77.16, 76.84, 57.49, 38.82, 37.03, 32.97, 29.79, 28.31. MS (ES-): m/z calc. for C$_{21}$H$_{22}$ClNO$_2$: 355.13; found: 354.3 [M-H]$^-$.

Scheme 17: Synthesis of compounds 8c-9c

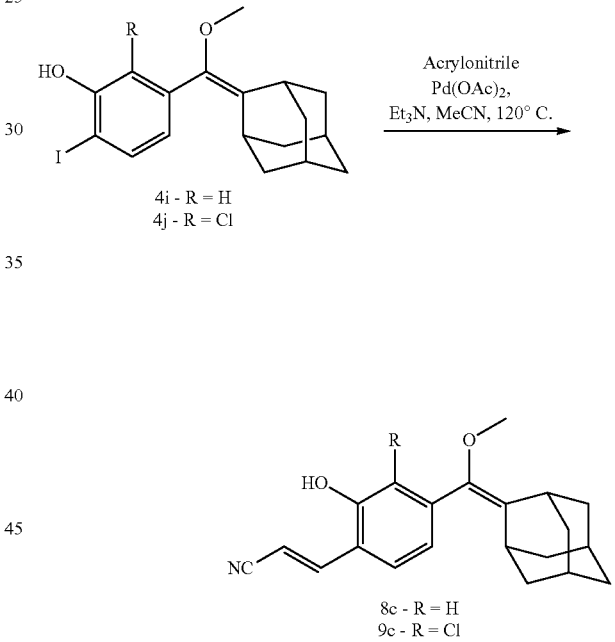

4i - R = H
4j - R = Cl

8c - R = H
9c - R = Cl

Scheme 16: Synthesis of compounds 6c-7c

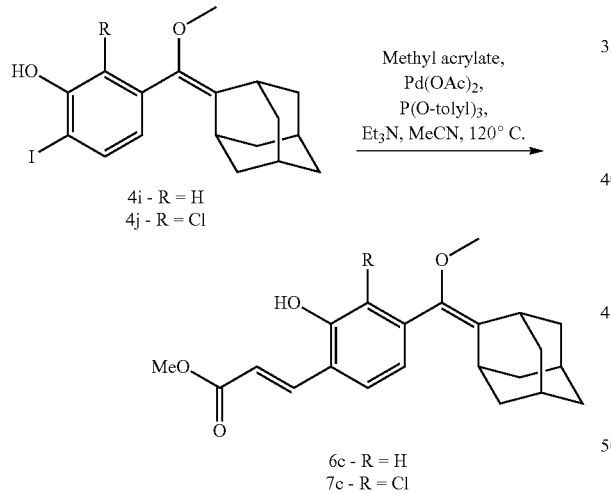

4i - R = H
4j - R = Cl

6c - R = H
7c - R = Cl

General procedure: Heck reaction of iodophenols with acrylonitrile (compounds 8c and 9c). Iodophenol (1eq), acrylonitrile (3eq) and Et$_3$N (1.5eq) were dissolved in anhydrous ACN. Then Pd(OAc)$_2$ (0.05eq) was added and the flask was sealed. The mixture was heated to 120° C. under microwave irradiation. Reaction was monitored by TLC (Hex:EtOAc 80:20). Upon completion, reaction mixture was diluted with EtOAc and washed with saturated NH$_4$Cl. The organic phase was dried over Na$_2$SO$_4$ and concentrated under reduced pressure. The residue was purified by column chromatography on silica gel (Hex:EtOAc 80:20) to afford the corresponding phenol acrylate.

Compound 8c. Compound 4i (200 mg, 0.5 mmol) was reacted according to the general method. The product was Phenol 5b. Enol ether 1f (100 mg 0.3 mmol) and few milligrams of methylene blue were dissolved in 20 ml of DCM. Oxygen was bubbled through the solution while irradiating with yellow light. The reaction was monitored by RP-HPLC. After completion, the reaction mixture was concentrated by evaporation under reduced pressure. The crude product was purified by preparative RP-HPLC (gradient of ACN in water). The product was obtained as a white solid. $^1$H NMR (400 MHz, DMSO) δ 10.34 (s, 1H), 7.38 (d, J=7.2 Hz, 1H), 7.27 (t, J=7.9 Hz, 1H), 7.08 (dd, J=8.0, 1.3 Hz, 1H), 3.07 (s, 3H), 2.85 (s, 1H), 2.27 (d, J=12.2 Hz, 1H), 1.93 (s, 1H), 1.72-1.05 (m, 11H). $^{13}$C NMR (101 MHz, DMSO) δ 154.23, 132.16, 127.40, 123.00, 118.02, 111.59, 95.19, 49.14, 35.97, 33.23, 32.95, 31.82, 31.75, 31.12, 30.80, 25.55, 25.24. (101 mg, 92% yield). MS (ES+): m/z calc. for C$_{18}$H$_{21}$ClO$_4$: 336.1; found: 337.3 [M+H]$^+$.

Scheme 18: Synthesis of phenol 5b

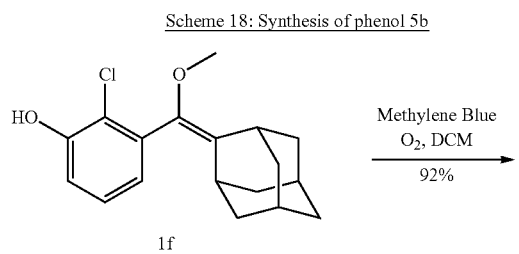

General procedure: dioxetane formation (compounds 6b-9b). Enol ether and few milligrams of methylene blue were dissolved in 20 ml of DCM. Oxygen was bubbled through the solution while irradiating with yellow light. The reaction was monitored by RP-HPLC. After completion, the reaction mixture was concentrated by evaporation under reduced pressure. The crude product was purified by preparative RP-HPLC (gradient of ACN in water).

Phenol 6b. Compound 6c (90 mg, 0.25 mmol) was reacted according to the general procedure. The product was obtained as a white solid (70 mg, 71% yield). $^1$H NMR (400 MHz, DMSO) δ 10.54 (s, 1H), 7.84 (d, J=16.2 Hz, 1H), 7.71 (d, J=8.1 Hz, 1H), 7.19 (s, 1H), 6.96 (s, 1H), 6.67 (d, J=16.2 Hz, 1H), 3.70 (s, 3H), 3.10 (s, 3H), 2.88 (s, 1H), 1.82-1.38 (m, 10H), 1.25 (d, J=12.9 Hz, 1H), 0.99 (d, J=12.8 Hz, 1H). $^{13}$C NMR (101 MHz, DMSO) δ 167.56, 157.19, 139.75, 137.98, 129.52, 118.76, 111.80, 95.15, 52.00, 50.26, 36.24, 34.65, 33.29, 32.97, 32.31, 31.62, 25.94, 25.81. MS (ES-): m/z calc. for $C_{22}H_{26}O_6$: 386.2; found: 385.2 [M−H]$^−$.

Phenol 7b. Compound 7c (60 mg, 0.15 mmol) was reacted according to the general procedure. The product was obtained as a white solid (20 mg, 31% yield). $^1$H NMR (400 MHz, DMSO) δ 10.14 (s, 1H), 7.91 (d, J=16.2 Hz, 1H), 7.80 (d, J=8.4 Hz, 1H), 7.47 (d, J=8.3 Hz, 1H), 6.71 (d, J=16.1 Hz, 1H), 3.72 (s, 3H), 3.09 (s, 3H), 2.86 (s, 1H), 2.22 (d, J=12.2 Hz, 1H), 1.79-1.27 (m, 12H). $^{13}$C NMR (101 MHz, DMSO) δ 167.20, 139.09, 134.17, 126.77, 124.05, 120.45, 111.89, 95.94, 52.16, 49.86, 36.47, 33.57, 32.48, 32.23, 31.67, 31.42, 26.09, 25.78. MS (ES-): m/z calc. for $C_{22}H_{25}ClO_6$: 420.1; found: 419.2 [M−H]$^−$.

Phenol 8b. Compound 8c (100 mg, 0.31 mmol) was reacted according to the general procedure. The product was obtained as a white solid (55 mg, 50% yield). $^1$H NMR (400 MHz, DMSO) δ 10.76 (s, 1H), 7.65 (d, J=16.7 Hz, 2H), 7.18 (s, 1H), 7.02 (s, 1H), 6.49 (d, J=16.8 Hz, 1H), 3.11 (s, 3H), 2.89 (s, 1H), 2.03 (s, J=27.8, 9.6 Hz, 1H), 1.85-1.40 (m, 10H), 1.26 (d, J=13.2 Hz, 1H), 0.93 (d, 1H). $^{13}$C NMR (101 MHz, DMSO) δ 172.34, 156.84, 146.10, 138.37, 129.68, 119.63, 111.58, 97.96, 95.01, 55.30, 50.14, 36.07, 34.49, 33.12, 32.82, 32.15, 31.45, 25.78, 25.64. MS (ES-): m/z calc. for $C_{21}H_{23}NO_4$: 353.2; found: 352.2 [M−H]$^−$.

Phenol 9b. Compound 9c (120 mg, 0.35 mmol) was reacted according to the general procedure. The product was obtained as a white solid (52 mg, 38% yield). $^1$H NMR (400 MHz, CDCl$_3$) δ 7.70 (d, J=8.1 Hz, 1H), 7.60 (d, J=16.8 Hz, 1H), 7.42 (d, J=8.3 Hz, 1H), 6.61 (d, J=5.4 Hz, 1H), 6.23 (d, J=16.8 Hz, 1H), 3.21 (s, 3H), 3.01 (s, 1H), 2.01 (s, 1H), 1.89-1.37 (m, 12H). $^{13}$C NMR (101 MHz, CDCl$_3$) δ 150.69, 144.77, 134.74, 126.82, 124.84, 122.80, 118.18, 111.40, 99.99, 96.28, 49.68, 36.42, 34.01, 33.42, 32.79, 32.08, 31.49, 26.04, 25.70. MS (ES-): m/z calc. for $C_{21}H_{21}ClNO_4$: 387.1; found: 386.2 [M−H]$^−$.

Scheme 19: Synthesis of phenols 6b-9b

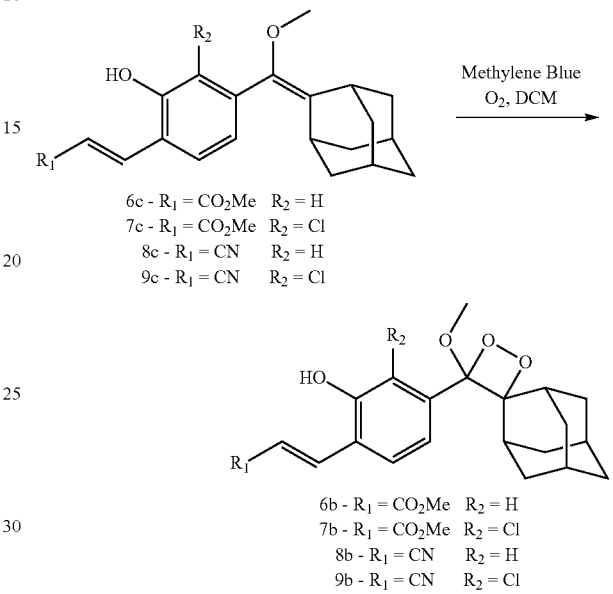

Compound 41. Compound 4k (Redy-Keisar et al., 2014) (1.0 g, 2.2 mmol) and NaI (1.0 g, 6.7 mmol) were dissolved in 2 mL ACN and cooled to 0° C. After 10 min, TMS-C$_1$ (837 μl, 6.7 mmol) was added. The reaction mixture stirred for 30 minutes at RT and monitored by TLC (Hex:EtOAc 70:30). After completion, the reaction mixture diluted with EtOAc, and was washed with saturated NH$_4$C$_1$. The organic layer was separated, washed with brine, dried over Na$_2$SO$_4$ and evaporated under reduced pressure. The crude product was purified by column chromatography on silica gel (Hex:EtOAc 70:30) to afford compound 41 as a white solid (1.08 g, 87% yield). $^1$H NMR (400 MHz, CDCl$_3$) δ 7.31 (d, J=8.6 Hz, 2H), 6.91 (d, J=8.6 Hz, 2H), 5.56-5.35 (m, 2H), 5.09 (dd, J=10.4, 3.4 Hz, 1H), 5.03 (d, J=7.9 Hz, 1H), 4.44 (s, 2H), 4.25-4.02 (m, 1H), 2.18 (s, 3H), 2.04 (s, 6H), 2.02 (s, 3H). $^{13}$C NMR (101 MHz, CDCl$_3$) δ 170.45, 169.70, 156.61, 134.52, 130.36, 117.45, 99.68, 71.33, 71.07, 68.82, 67.10, 61.64, 20.97, 5.67. MS (ES-): m/z calc. for $C_{21}H_{25}IO_{10}$: 564.1; found: 587.2 [M+Na]$^+$.

Scheme 20: Synthesis of compound 4l

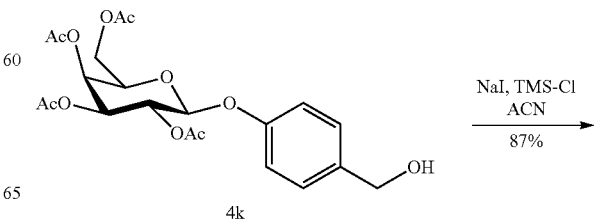

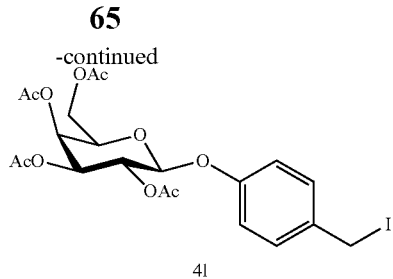

41

General procedure for S$_N$2, benzyl ether formation (compounds 6d-9d). Enol ether (1eq) was dissolved in 1 mL dry DMF and cooled to 0° C. K$_2$CO$_3$ (1.2eq) was added and the solution stirred at 0° C. for 10 minutes, before compound 41 (1eq) was added. The reaction mixture stirred for 30 minutes at RT and monitored by TLC (Hex:EtOAc 50:50). After completion, the reaction mixture diluted with EtOAc (100 ml) and was washed with saturated NH$_4$C$_1$ (100 ml). The organic layer was separated, washed with brine, dried over Na$_2$SO$_4$ and evaporated under reduced pressure. The crude product was purified by column chromatography on silica gel (Hex:EtOAc 50:50).

Compound 6d. Compound 6c (100 mg, 0.28 mmol) was reacted according to the general procedure. The product was obtained as a white solid (186 mg, 84% yield). $^1$H NMR (400 MHz, CDCl$_3$) δ 8.03 (d, J=16.2 Hz, 1H), 7.49 (d, J=8.0 Hz, 1H), 7.36 (d, J=8.5 Hz, 2H), 7.02 (d, J=8.5 Hz, 2H), 6.94-6.88 (m, J=7.5 Hz, 2H), 6.52 (d, J=16.1 Hz, 1H), 5.53-5.43 (m, 2H), 5.12 (d, J=3.4 Hz, 1H), 5.10 (s, 2H), 5.05 (d, J=7.9 Hz, 1H), 4.26-4.04 (m, 4H), 3.78 (s, 3H), 3.25 (s, 3H), 3.23 (s, 1H), 2.63 (s, 1H), 2.18 (s, 3H), 2.08 (d, J=5.6 Hz, 3H), 2.06 (s, 3H), 2.01 (s, 3H), 1.99-1.69 (m, 12H). $^{13}$C NMR (101 MHz, CDCl$_3$) δ 170.48, 170.36, 170.25, 169.52, 168.06, 157.08, 156.79, 142.95, 139.90, 139.03, 133.59, 131.46, 129.00, 128.38, 122.85, 122.32, 118.09, 117.13, 113.32, 99.72, 71.11, 70.91, 69.82, 68.66, 66.92, 61.41, 58.03, 51.70, 39.28, 39.11, 37.15, 32.41, 30.46, 28.27, 20.83, 20.76, 20.69 MS (ES+): m/z calc. for C$_{43}$H$_{50}$O$_4$: 790.3; found: 813.6 [M+Na]$^+$.

Compound 7d. Compound 7c (200 mg, 0.51 mmol) was reacted according to the general procedure. The product was obtained as a white solid (273 mg, 65% yield). $^1$H NMR (400 MHz, CDCl$_3$) δ 7.87 (d, J=16.2 Hz, 1H), 7.43-7.36 (m, 3H), 7.03 (d, J=8.0 Hz, 1H), 6.97 (d, J=8.6 Hz, 2H), 6.41 (d, J=16.2 Hz, 1H), 5.42-5.40 (m, J=3.7 Hz, 2H), 5.03 (d, 1H), 4.93-4.85 (m, 2H), 4.21-4.09 (m, 4H), 3.75 (s, 3H), 3.26 (s, 3H), 3.23 (s, 1H), 2.09-1.62 (m, 24H). $^{13}$C NMR (101 MHz, CDCl$_3$) δ 170.42, 170.32, 170.15, 169.47, 167.12, 157.24, 153.68, 139.43, 138.86, 138.19, 132.43, 131.01, 130.45, 130.11, 129.81, 129.64, 127.87, 125.13, 119.89, 116.99, 99.62, 75.62, 72.79, 71.06, 70.85, 68.67, 66.96, 61.44, 60.42, 57.26, 51.83, 39.20, 38.64, 37.05, 32.94, 29.70, 28.35, 20.76, 20.70, 14.23. MS (ES+): m/z calc. for C$_{43}$H$_{49}$ClO$_{14}$: 824.3; found: 847.7 [M+Na]$^+$.

Compound 8d. Compound 8c (129 mg, 0.4 mmol) was reacted according to the general procedure. The product was obtained as a white solid (263 mg, 87% yield). $^1$H NMR (400 MHz, CDCl$_3$) δ 7.59 (d, J=16.8 Hz, 1H), 7.41 (d, J=7.5 Hz, 1H), 7.31 (d, J=8.0 Hz, 2H), 7.26-7.24 (m, 2H), 7.05 (d, J=8.4 Hz, 2H), 6.05 (d, J=16.8 Hz, 1H), 5.11 (m, J=8.7 Hz, 2H), 4.85 (d, J=7.6 Hz, 1H), 3.98 (s, 1H), 3.88-3.77 (m, 2H), 3.62 (dd, J=7.9, 4.9 Hz, 1H), 3.15 (s, 2H), 2.96 (s, 1H), 2.01 (s, 1H), 1.83-1.12 (m, 12H). $^{13}$C NMR (101 MHz, CDCl$_3$) δ 170.65, 170.55, 170.41, 169.73, 157.34, 157.22, 146.30, 142.93, 140.22, 134.44, 131.06, 130.35, 129.53, 128.81, 122.57, 122.05, 119.49, 117.42, 113.33, 99.81, 96.85, 71.33, 71.08, 70.23, 68.84, 67.13, 61.63, 58.31, 39.46, 39.29, 37.30, 32.65, 30.69, 29.95, 28.42, 20.95, 20.88. MS (ES-): m/z calc. for C$_{42}$H$_{47}$NO$_{12}$: 757.31; found: 802.6 [M+HCOO]$^-$.

Compound 9d. Compound 9c (77 mg, 0.22 mmol) was reacted according to the general procedure. The product was obtained as a pale yellow solid (160 mg, 90% yield). $^1$H NMR (400 MHz, CDCl$_3$) δ 7.32 (d, J=16.8 Hz, 1H), 7.19 (d, J=8.5 Hz, 2H), 7.16 (d, J=8.1 Hz, 1H), 6.92 (d, J=8.0 Hz, 1H), 6.87 (d, J=8.6 Hz, 2H), 5.73 (d, J=16.8 Hz, 1H), 5.37-5.26 (m, 2H), 5.00-4.92 (m, 2H), 4.81 (d, J=6.5 Hz, 1H), 4.09-3.89 (m, 4H), 3.15 (s, 6H), 3.10 (s, 1H), 2.01 (s, 4H), 1.93-1.45 (m, 21H). $^{13}$C NMR (101 MHz, CDCl$_3$) δ 170.43, 170.33, 170.17, 169.53, 157.42, 153.30, 144.91, 139.31, 139.20, 132.99, 130.58, 130.44, 130.13, 130.01, 128.87, 128.01, 124.52, 118.11, 117.23, 99.64, 98.22, 75.72, 71.09, 70.86, 68.65, 66.95, 61.42, 57.40, 39.21, 39.04, 38.65, 37.02, 33.01, 29.75, 28.33, 28.18, 20.81, 20.73, 20.66. MS (ES-): m/z calc. for C$_{42}$H$_{46}$ClNO$_{12}$: 791.27; found: 836.8 [M+HCOO]$^-$.

Probe 5. Was synthesized from compound 1g in Scheme 9, by deoxygenation of the double bond and removal of the acetyl groups from the galactose moiety.

Scheme 21: Molecular structure of Probe 5

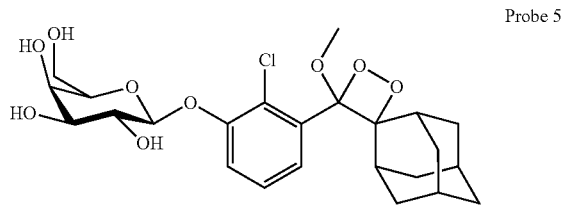

Probe 5

General procedure for acetate deprotection and dioxetane formation (Probes 6-9). The acetate protected sugar-enol-ether was dissolved in McOH (3 ml). Potassium carbonate (4.2eq) was added and the solution was stirred at RT. The Reaction was monitored by RP-HPLC. Upon completion, the reaction mixture was diluted with EtOAc (100 ml) and washed with brine (100 ml). The organic phase was dried over Na$_2$SO$_4$ and concentrated under reduced pressure. The crude product was further reacted without purification. The crude product and few milligrams of methylene blue were dissolved in 20 ml of DCM. Oxygen was bubbled through the solution while irradiating with yellow light. The reaction was monitored by RP-HPLC. After completion, the reaction mixture was concentrated by evaporation under reduced pressure. The crude product was purified by preparative RP-HPLC (gradient of ACN in water).

Probe 6. Compound 6d (133 mg, 0.22 mmol) was reacted according to general procedure. The product obtained as a white solid (64 mg, 63% yield). $^1$H NMR (400 MHz, MeOD) δ 8.01 (d, J=16.2 Hz, 1H), 7.66 (d, J=7.9 Hz, 1H), 7.33 (d, J=8.1 Hz, 2H), 7.08 (d, J=8.3 Hz, 2H), 6.58 (d, J=16.2 Hz, 1H), 5.24 (s, 2H), 4.81 (d, J=7.9 Hz, 1H), 3.87 (d, J=3.3 Hz, 1H), 3.81-3.68 (m, 4H), 3.67-3.59 (m, 1H), 3.54 (dd, J=9.7, 3.3 Hz, 1H), 3.12 (s, 3H), 2.89 (s, 1H), 1.80-1.38 (m, 12H). $^{13}$C NMR (101 MHz, MeOD) δ 169.27, 139.28, 138.05, 128.32, 119.56, 116.61, 111.59, 101.62, 95.28, 75.56, 73.49, 70.85, 69.63, 68.78, 60.97, 48.89, 35.99, 34.35, 33.18, 32.62, 31.91, 31.72, 31.25, 26.14, 25.87. MS (ES-): m/z calc. for C$_{34}$H$_{40}$O$_2$: 654.3; found: 653.4 [M-H]$^-$.

Probe 7. Compound 7d (273 mg 0.33 mmol) was reacted according to general procedure. The product obtained as a white solid (90 mg, 40% yield). $^1$H NMR (400 MHz, MeOD) δ 7.87 (d, J=8.4 Hz, 1H), 7.83 (d, J=16.3 Hz, 1H), 7.74 (d, J=8.4 Hz, 1H), 7.33 (d, J=8.5 Hz, 2H), 7.09 (d, J=8.4 Hz, 2H), 6.55 (d, J=16.2 Hz, 1H), 4.93 (s, 2H), 4.83 (d, J=8.4 Hz, 1H), 3.90 (d, J=3.3 Hz, 1H), 3.82-3.77 (m, 4H), 3.77-3.73 (m, 2H), 3.72-3.65 (m, 1H), 3.57 (dd, J=9.7, 3.4 Hz, 1H), 3.17 (s, 3H), 2.95 (s, 1H), 1.97 (s, 1H), 1.88-1.35 (m, 12H). $^{13}$C NMR (101 MHz, MeOD) δ 167.22, 158.35, 138.22, 131.78, 130.48, 129.58, 128.64, 125.19, 120.57, 116.45, 101.57, 95.86, 75.83, 75.64, 73.50, 70.89, 68.87, 61.07, 51.12, 48.65, 48.31, 36.26, 33.71, 32.26, 31.82, 31.57, 31.31, 26.33, 25.96. MS (ES+): m/z calc. for $C_{35}H_{41}ClO_{12}$: 688.2; found: 711.5 [M+Na]+.

Probe 8. Compound 8d (130 mg 0.17 mmol) was reacted according to general procedure. The product obtained as a white solid (69 mg, 65% yield). $^1$H NMR (400 MHz, CDCl$_3$) δ 7.56 (d, J=16.8 Hz, 1H), 7.40 (d, J=7.9 Hz, 1H), 7.28 (d, J=7.9 Hz, 2H), 7.21 (br, 1H), 7.07 (d, J=7.0 Hz, 2H), 6.01 (d, J=16.8 Hz, 1H), 5.02 (dd, J=22.2, 11.2 Hz, 2H), 4.90 (s, 1H), 4.21-3.66 (m, 10H), 3.15 (s, 3H), 2.98 (s, 1H), 2.06 (s, 1H), 1.86-1.40 (m, 10H). 13C NMR (101 MHz, CDCl$_3$) δ 157.56, 145.99, 139.54, 130.22, 129.73, 128.92, 119.11, 117.39, 111.89, 101.55, 98.18, 95.91, 74.65, 73.60, 71.25, 70.73, 61.59, 50.29, 36.52, 35.03, 33.47, 32.51, 31.95, 31.76, 26.21, 26.06. MS (ES-): m/z calc. for $C_{34}H_{39}NO_{10}$: 621.3; found: 644.4 [M+Na]+.

Probe 9. Compound 9d (160 mg, 0.2 mmol) was reacted according to general procedure. The product obtained as a white solid (61 mg, 46% yield). $^1$H NMR (400 MHz, MeOD) δ 7.86 (d, J=8.3 Hz, 1H), 7.66 (d, J=8.4 Hz, 1H), 7.45 (d, J=16.9 Hz, 1H), 7.26 (d, J=8.4 Hz, 2H), 7.10 (d, J=8.4 Hz, 2H), 6.17 (d, J=16.8 Hz, 1H), 4.98 (s, 2H), 3.90 (d, J=3.1 Hz, 1H), 3.84-3.63 (m, 10H), 3.58 (dd, J=9.6, 3.1 Hz, 1H), 3.17 (s, 3H), 2.95 (s, 1H), 2.36 (d, J 12.4 Hz, 1H), 1.94 (s, 1H), 1.87-1.45 (m, 10H). $^{13}$C NMR (101 MHz, MeOD) δ 156.95, 142.68, 134.37, 129.90, 129.08, 127.72, 127.11, 123.05, 116.09, 115.07, 109.88, 100.02, 97.64, 94.30, 74.29, 74.10, 71.92, 69.34, 67.33, 59.54, 47.13, 46.75, 46.54, 46.33, 46.11, 45.90, 45.69, 45.48, 34.68, 32.16, 32.01, 30.76, 30.24, 30.02, 29.74, 24.76, 24.39. MS (ES+): m/z calc. for $C_{34}H_{38}ClNO_{10}$: 655.2; found: 700.5 [M+HCOO]−.

Compound 10a. Enol ether 6c (500 mg, 1.41 mmol) and triethylamine (0.49 ml, 3.5 mmol) were dissolved in 5 ml of DCM and cooled to 0° C. Trifluoromethanesulfonic anhydride (0.29 ml, 1.7 mmol) was added. Reaction mixture was monitored by TLC. Upon completion, reaction mixture was diluted with DCM (100 ml) and washed with brine (100 ml). Organic phase was dried over Na$_2$SO$_4$ and concentrated under reduced pressure. Purification by column chromatography (Hex:EtOAc 80:20) afforded compound 7a as a yellow oil (562 mg, 82% yield). $^1$H NMR (400 MHz, CDCl$_3$) δ 7.86 (d, J=16.0 Hz, 1H), 7.67 (d, J=8.1 Hz, 1H), 7.37 (dd, J=8.1, 1.1 Hz, 1H), 7.31 (d, J=1.4 Hz, 1H), 6.51 (d, J=16.0 Hz, 1H), 3.83 (s, 3H), 3.32 (s, 3H), 3.25 (s, 1H), 2.69 (s, 1H), 2.02-1.74 (m, 12H). $^{13}$C NMR (101 MHz, CDCl$_3$) δ 166.44, 147.46, 141.38, 139.76, 135.98, 135.85, 129.08, 127.75, 126.42, 122.66, 121.60, 58.27, 51.96, 39.06, 38.98, 36.90, 32.30, 31.55, 30.54, 28.05, 22.61, 14.07. $^{19}$F NMR (376 MHz, CDCl$_3$) δ −73.69. MS (ES+): m/z calc. for $C_{23}H_{25}F3O_6S$: 486.1; found: 489.3 [M+H]+.

Scheme 22: Synthesis of compound 6d-9d and Probes 6-9

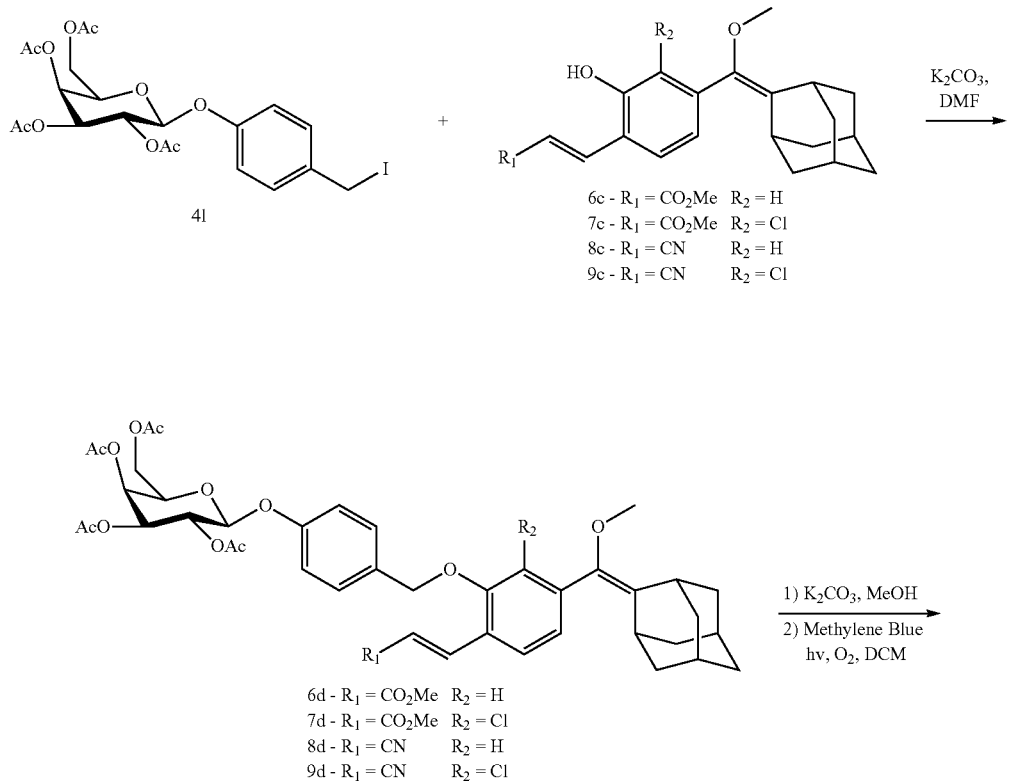

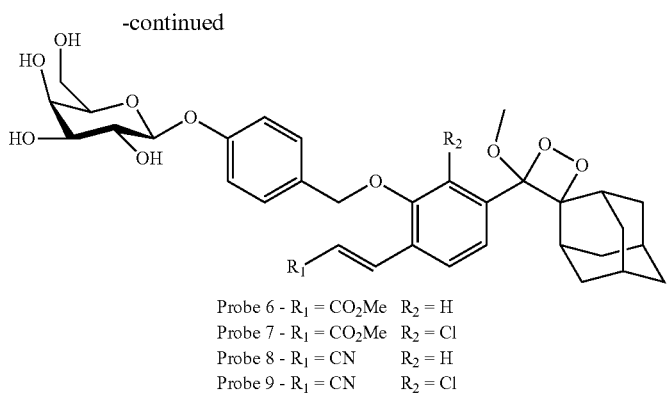

Probe 6 - R₁ = CO₂Me  R₂ = H
Probe 7 - R₁ = CO₂Me  R₂ = Cl
Probe 8 - R₁ = CN     R₂ = H
Probe 9 - R₁ = CN     R₂ = Cl Compound 10b. Compound 10a (562 mg, 1.16 mmol), bis(pinacolato)diboron (589 mg, 2.32 mmol), potassium acetate (341 mg, 3.48 mmol), [1,1'-bis(diphenylphosphino)ferrocene]dichloropalladium(II) (170 mg, 0.23 mmol) were dissolved in 20 ml of dry dioxane and stirred at 120° C. under argon. Reaction was monitored by RP-HPLC. Upon completion, reaction mixture was diluted with EtOAc (100 ml) and washed with Brine. Organic phase was dried over Na₂SO₄ and concentrated under reduced pressure. Purification by column chromatography (Hex:EtOAc 70:30) afforded compound 10b as a yellow oil (441 mg, 82% yield). ¹H NMR (400 MHz, CDCl₃) δ 8.53 (d, J=16.0 Hz, 1H), 7.77 (d, J=1.7 Hz, 1H), 7.66 (d, J=8.1 Hz, 1H), 7.37 (dd, J=8.1, 1.6 Hz, 1H), 6.39 (d, J=16.0 Hz, 1H), 3.80 (s, 3H), 3.29 (s, 3H), 3.25 (s, 1H), 2.63 (s, 1H), 2.01-1.75 (m, 12H), 1.38 (s, 12H). ¹³C NMR (101 MHz, CDCl₃) δ 167.83, 145.63, 143.09, 139.00, 136.84, 136.38, 133.18, 131.96, 125.41, 118.30, 84.28, 58.11, 51.70, 39.21, 39.15, 37.27, 32.38, 31.69, 30.39, 29.80, 28.36, 24.93, 22.76, 14.24. MS (ES+): m/z calc. for C₂₈H₃₅O₇P: 464.3; found: 465.4 [M+H]⁺.

Probe 10. Borane 10b (441 mg, 0.95 mmol), NaOH 114 mg, 2.8 mmol) were dissolved in 5 ml of 4:1 solution THF:H₂O. Reaction mixture was stirred at 40° C. overnight and was monitored by RP-HPLC. Upon completion, the reaction mixture diluted with EtOAc (100 ml) and was washed with saturated solution of 0.5M HCl (100 ml). The organic layer was separated, washed with brine, dried over Na₂SO₄ and evaporated under reduced pressure. The crude residue and few milligrams of methylene blue were dissolved in 20 ml of DCM. Oxygen was bubbled through the solution while irradiating with yellow light. The reaction was monitored by RP-HPLC. Upon completion, the solvent was concentrated under reduced pressure and the product was purified by preparative RP-HPLC (gradient of ACN in water). The product was obtained as a white solid (201 mg, 47% yield). ¹H NMR (400 MHz, MeOD) δ 8.53 (d, J=16.0 Hz, 1H), 7.81 (d, J=8.1 Hz, 1H), 6.41 (d, J=16.0 Hz, 1H), 3.11 (s, 3H), 2.92 (s, 1H), 2.00 (s, 1H), 1.87-1.48 (m, 12H), 1.32 (s, 12H). ¹³C NMR (101 MHz, MeOD) δ 169.03, 144.93, 141.56, 135.21, 125.64, 120.20, 111.64, 95.07, 84.36, 74.54, 48.93, 36.04, 34.43, 33.27, 32.61, 31.94, 31.76, 31.27, 29.46, 26.18, 26.00, 24.85, 23.98, 23.84, 23.72. MS (ES-): m/z calc. for C₂₇H₃₅BO₇: 482.30; found: 399.2 [M-pinacol]⁻.

Scheme 23: Synthesis of compounds 10a-10b and Probe 10

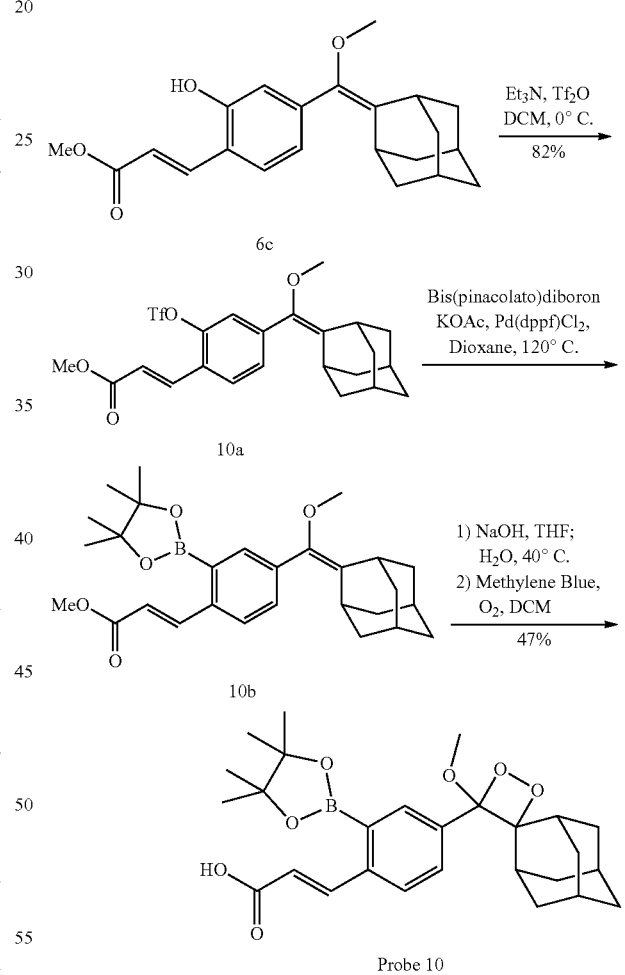

Compound 11a. Enol ether 6c (200 mg, 0.56 mmol) was dissolved in 2 ml of DCM and DMAP (136 mg, 1.12 mmol) was added and the solution was stirred at RT. Triallyl phosphite (0.25 ml, 1.23 mmol) was dissolved in 2 ml of DCM and cooled to 0° C. Iodine (284 mg, 1.12 mmol) was added and reaction stirred to homogeneity. The iodine solution was pipetted to the phenol solution. The reaction was monitored by TLC. Upon completion, reaction mixture was diluted with DCM (100 ml) and washed with brine (100 ml). The organic phase was dried over $Na_2SO_4$ and concentrated under reduced pressure. Purification by column chromatography (Hex:EtOAc 70:30) afforded compound 11a as a yellow oil (162 mg, 56% yield). $^1$H NMR (400 MHz, $CDCl_3$) δ 7.96 (d, J=16.1 Hz, 1H), 7.57 (d, J=8.1 Hz, 1H), 7.41-7.34 (m, 1H), 7.17 (d, J=8.1 Hz, 1H), 6.47 (d, J=16.1 Hz, 1H), 6.05-5.86 (m, 2H), 5.38 (dd, J=17.1, 1.4 Hz, 2H), 5.33-5.22 (m, 2H), 4.77-4.63 (m, 4H), 3.81 (s, 3H), 3.33 (s, 3H), 3.24 (s, 1H), 2.70 (s, 1H), 2.03-1.75 (m, 12H). $^{13}$C NMR (101 MHz, $CDCl_3$) δ 167.25, 149.04, 142.23, 139.25, 138.13, 134.45, 131.97, 127.48, 126.09, 124.95, 121.20, 119.41, 118.89, 69.12, 58.16, 51.78, 39.18, 39.05, 37.09, 32.33, 30.48, 28.20. $^{31}$P NMR (162 MHz, $CDCl_3$) δ -5.79. MS (ES+): m/z calc. for $C_{28}H_{35}O_7P$: 514.2; found: 537.3 $[M+Na]^+$.

Probe 11. Phosphate 11a (166 mg, 0.3 mmol) was dissolved in 1 ml of ACN. Pyrrolidine (0.153 ml, 1.86 mmol), triphenyl phosphine (16 mg, 0.06 mmol), tetrakis(triphenylphosphine) palladium(0) (17 mg, 0.015 mmol) was added and the solution was stirred at RT. After completion the precipitant was filtered and washed 3 times with ACN to give a yellowish solid. The crude solid and NaOH (30 mg, 0.76 mmol) were dissolved in 2 ml of 4:1 THF:$H_2O$ solution. Reaction mixture was stirred at 40° C. overnight and was monitored by RP-HPLC. Upon completion, the reaction mixture was neutralized with 1M $HCl_{(aq)}$ and the solvent was evaporated under reduce pressure. The crude residue and few milligrams of methylene blue were dissolved in 20 ml of DCM. Oxygen was bubbled through the solution while irradiating with yellow light. The reaction was monitored by RP-HPLC. Upon completion the solvent was concentrated under reduced pressure and the product was purified by RP-HPLC (10-75% ACN, ammonium carbonate 5 mM Buffer, 20 min) to afford Probe 11 as a white solid (41 mg, 35% yield). $^{31}$P NMR (162 MHz, $D_2O$) 8-2.11. MS (ES-): m/z calc. for $C_2,H_{25}O_9P$: 452.1; found: 451.2 $[M-H]^-$.

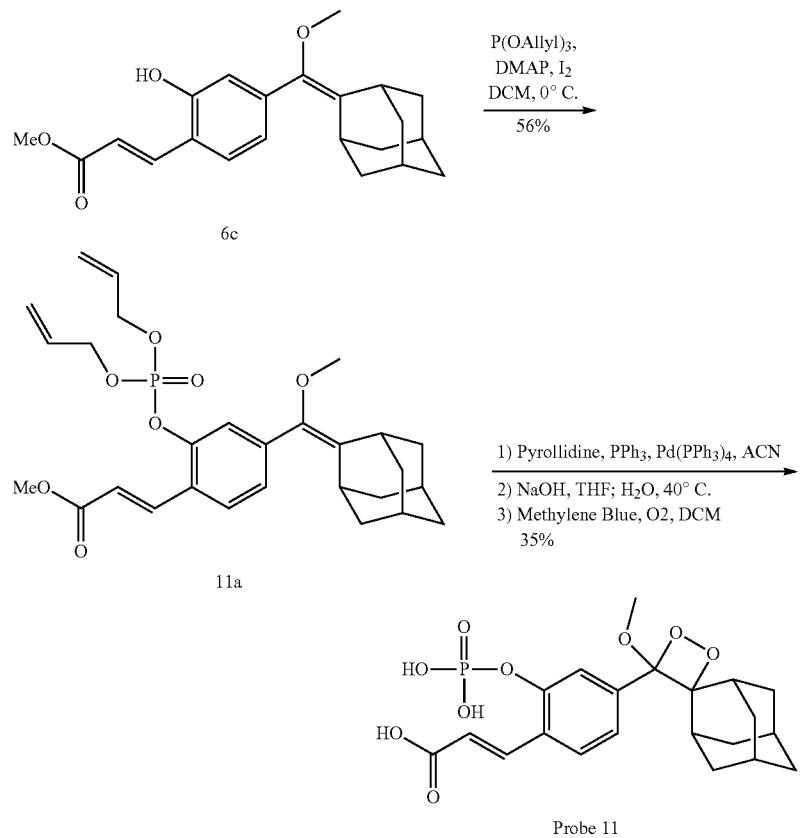

Scheme 24: Synthesis of compound 11a and Probe 11

Compound 12a. Diethyl azodicarboxylate (95 μl, 0.6 mmol) was added to a cooled mixture of compound 4m (Redy-Keisar et al., 2014) (184 mg, 0.5 mmol), compound 6c (177 mg, 0.5 mmol) and triphenylphosphine (157 mg, 0.6 mmol) in 3 mL of THF at 0° C. Reaction was monitored by TLC (Hex:EtOAc 80:20). Upon completion, reaction mixture was diluted with EtOAc and washed with saturated $NH_4Cl$. The organic phase was dried over $Na_2SO_4$ and concentrated under reduced pressure. The residue was purified by column chromatography on silica gel (Hex:EtOAc 80:20) to afford compound 12a as a pale yellow solid (274 mg, 78% yield).$^1$H NMR (400 MHz, $CDCl_3$) δ 8.46 (d, J=2.2 Hz, 1H), 8.36 (dd, J=8.7, 2.2 Hz, 1H), 8.02 (d, J=16.2 Hz, 1H), 7.71 (d, J=8.7 Hz, 1H), 7.52 (d, J=7.9 Hz, 1H), 7.45 (d, J=8.4 Hz, 2H), 7.29-7.20 (m, 2H), 6.95 (m, 2H), 6.52 (d, J=16.1 Hz, 1H), 5.15 (s, 2H), 3.80 (s, 3H), 3.45 (s, 3H), 3.29 (s, 3H), 3.25 (s, 1H), 2.66 (s, 1H), 1.99-1.76 (m, 12H).$^{13}$C NMR (101 MHz, $CDCl_3$) δ 168.00, 157.02, 149.96, 148.45, 142.96, 139.73, 139.39, 139.29, 137.42, 136.69, 133.88, 133.68, 128.75, 128.47, 127.97, 125.78, 122.96, 122.74, 119.50, 118.36, 113.22, 69.66, 58.14, 53.54, 51.78, 39.94, 39.37, 39.18, 37.20, 32.54, 31.71, 30.56, 29.82, 28.34, 22.77, 14.32, 14.23. MS (ES+): m/z calc. for $C_{36}H_{37}N_3O_{10}S$: 703.22; found: 726.4 $[M+Na]^+$.

Probe 12. Compound 12a (274 mg, 0.39 mmol) and few milligrams of methylene blue were dissolved in 20 ml of DCM. Oxygen was bubbled through the solution while irradiating with yellow light. The reaction was monitored by TLC (Hex:EtOAc 80:20). Upon completion, the reaction mixture was concentrated by evaporation under reduced pressure. The crude product was purified by column chromatography on silica gel (Hex:EtOAc 80:20) to afford Probe 12 (255 mg, 89% yield). $^1$H NMR (400 MHz, CDCl$_3$) δ 8.46 (d, J=2.0 Hz, 1H), 8.38 (dd, J=8.6, 2.1 Hz, 1H), 8.03 (d, J=16.2 Hz, 1H), 7.72 (d, J=8.7 Hz, 1H), 7.60 (d, J=7.9 Hz, 1H), 7.47 (d, J=8.2 Hz, 3H), 7.28 (d, J=7.4 Hz, 3H), 6.56 (d, J=16.2 Hz, 1H), 3.81 (s, 3H), 3.45 (s, 4H), 3.20 (s, 2H), 3.02 (s, 1H), 2.10 (s, 1H), 1.91-1.36 (m, 16H). $^{13}$C NMR (101 MHz, CDCl$_3$) δ 167.70, 156.96, 149.98, 148.45, 139.48, 139.18, 138.50, 137.11, 136.60, 133.67, 128.73, 127.97, 125.83, 124.80, 119.70, 119.53, 111.84, 95.78, 69.91, 51.89, 50.12, 39.88, 36.43, 34.90, 33.41, 33.30, 32.43, 31.83, 31.70, 31.64, 29.81, 26.10, 26.00, 22.77, 14.23. MS (ES+): m/z calc. for $C_{36}H_{37}N_3O_{12}S$: 735.21; found: 758.5 [M+Na]$^+$.

Chemiluminescence Microscopy Imaging of β-Galactosidase Activity

Chemiluminescence images were acquired using Olympus LV200 inverted microscope fitted with an EMCCD camera (Hamamatsu $C_{9100}$-13). HEK293 LacZ stable cells (amsbio SC003) and HEK293-WT cells (control) were grown on 35 mm glass bottom petri dishes at 37° C. for 24 h. Cell culture medium was changed to Molecular Probes® Live Cell Imaging Solution containing 5 μM of probe 4. Cells were incubated for another 20 minutes at 37° C. Thereafter, images were recorded with 40 seconds exposure time.

Results and Discussion

In this Study, chemiluminescent probes based on the Schapp's adamantylidene-dioxetane probe (Scheme 1), in which the phenolate donor is substituted at the ortho position of phenolic ring with a π* acceptor group such as methylacrylate and acrylonitrile, i.e., an electron acceptor or electron-withdrawing group, and optionally further substituted Scheme 25: Synthesis of compound 12a and Probe 12

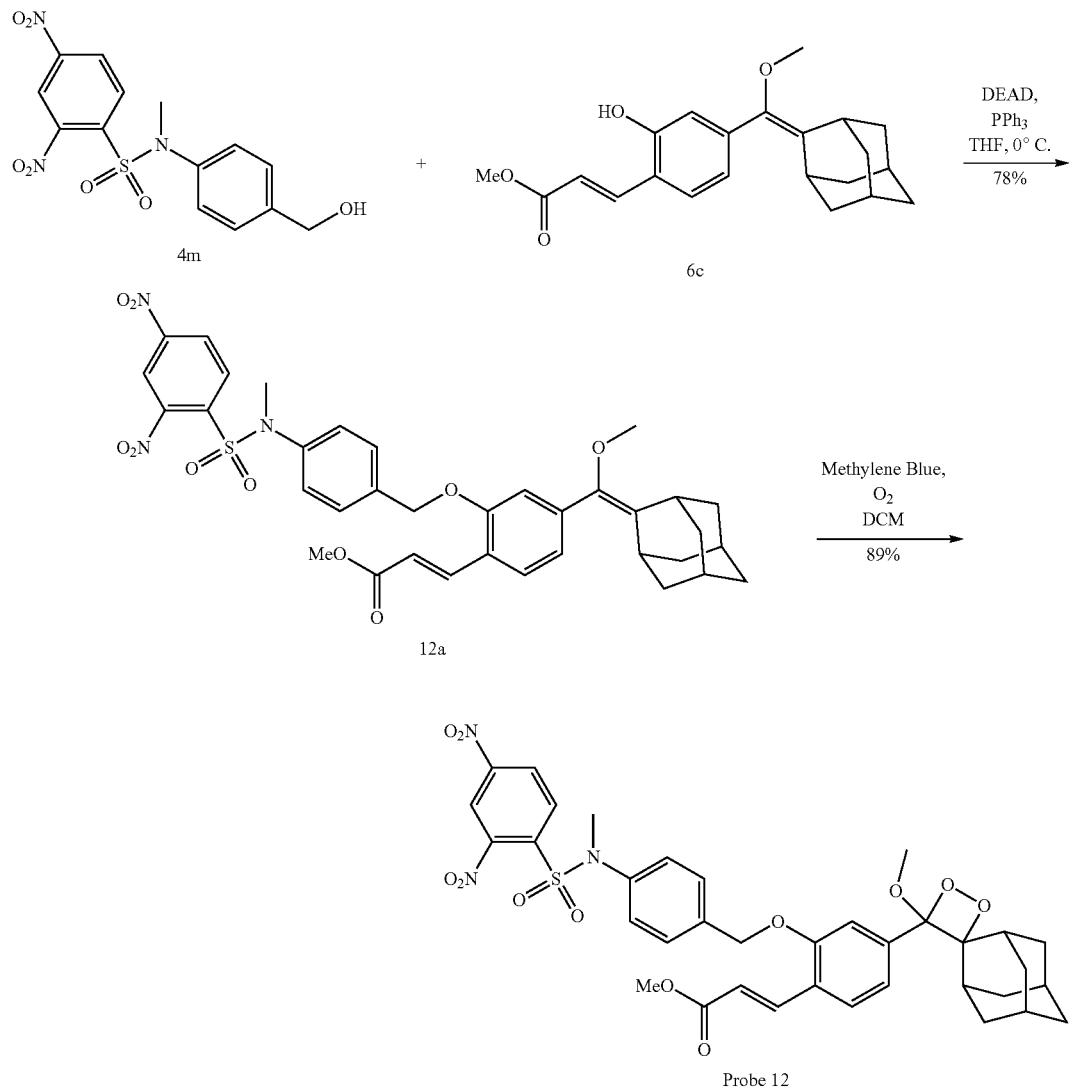

at the other ortho position of the phenolic ring with chlorine, were designed and synthesized. Based on the teaching of Karton-Lifshin et al. (2012) it has been postulated that such donor-acceptor pair design should potentially increase the emissive nature of the benzoate species. To the best of our knowledge, the influence of electron acceptor substituents on the aromatic moiety of dioxetane chemiluminescence probes was never studied before for physiologically-relevant pHs (Hagiwara et al., 2013; Matsumoto et al., 1996; Matsumoto et al., 2001; Matsumoto et al., 2002; Matsumoto et al., 2005).

Figure 11:
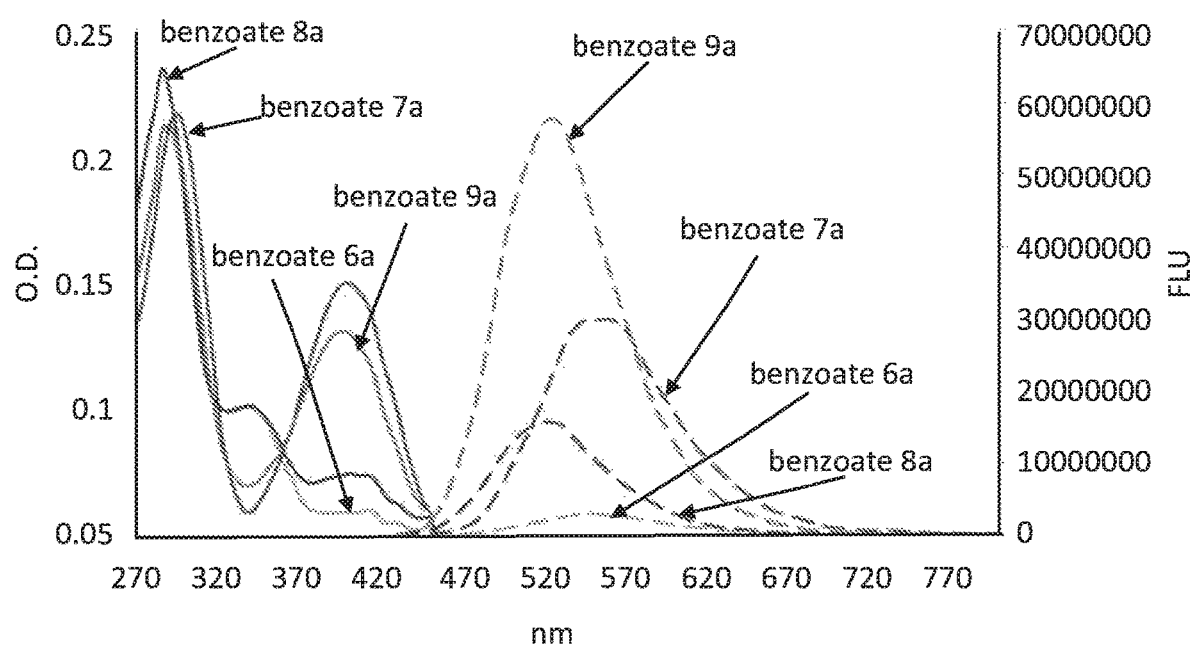
FIG. 11 shows absorbance (O. D., solid line) and fluorescence (FLU, dashed line) spectra of benzoates 6a, 7a, 8a and 9a [50 μM] in PBS 7.4 (5% DMSO), (excitation wavelength=290/400 nm).

To evaluate the substituent effect, numerous phenol-benzoate derivatives with acceptor substituents at ortho and para positions of the phenol were synthesized, and their fluorescent emission in PBS 7.4 were measured. The most significant effect was obtained when an acceptor was incorporated at the ortho position of the phenol. Following broad screen of electron-withdrawing groups, we chose to focus on the chlorine, methyl-acrylate and acrylonitrile substituents. It was previously shown that in order to enable the chemiexcitation mechanism under physiological conditions, a chlorine substituent is introduced at the ortho position of phenolic ring. This electron-withdrawing substituent decreases the pKa of the phenol released after cleavage of the protecting group and thereby enriches the relative concertation of the phenolate species in physiological pH. The methyl-acrylate and acrylonitrile substituents induced the highest increase in fluorescence emission of their corresponded phenol-benzoates. The absorbance and fluorescence spectra of selected phenol-benzoate derivatives are shown in FIG. 11, and their molecular structure and spectroscopic parameters are summarized Table 9.

The emissive species generated by the chemiexcitation of commercially available adamantylidene-dioxetane probes are eventually the excited state of benzoates 4a or 5a. These benzoates do not present any measurable fluorescence under physiological conditions. However, incorporation of methyl-acrylate or acrylonitrile substituents at the ortho position of the phenol (benzoates 6a and 8a) has produced strong fluorogenic phenol-benzoate derivatives (quantum yield; 0.5% and 7% respectively) with maximum emission wavelength of 550 nm and 525 nm, respectively. Insertion of additional chlorine substituent at the other ortho position (benzoate 7a) resulted in significant increase of the fluorescence emission intensity in comparison to its parent benzoate 6a (about 10-fold) with no change of the emission wavelength. The intensification of fluorescence emission is attributed to the increase concentration of the phenolate species under physiological conditions, resulted from the electron-withdrawing effect of the chlorine substituent. Similar increase effect in fluorescence emission (about 4-fold) was observed for benzoate 9a in comparison to its parent benzoate 8a.

These results suggest that incorporation of the methyl-acrylate and acrylonitrile substituents (with or without the chlorine) in the dioxetane chemiluminescent luminophores could strengthen the emissive nature of the released benzoate. Such a substituent effect would lead to a significant increase of the dioxetane's chemiluminescence quantum yield under physiological conditions.

TABLE 9

Spectroscopic fluorescence parameters measured for selected phenol-benzoate derivatives in PBS 7.4

| Phenol-benzoate | | $\lambda\,max_{ex}$ [nm] | $\lambda\,max_{em}$ [nm] | $\varepsilon_{400\,nm}$ | Relative fluorescence emission | $\Phi$Fluorescence |
|---|---|---|---|---|---|---|
| 4a | (HO-phenyl-C(O)OMe) | 290 | 470 | ND | negligible | ND |
| 5a | (HO-, Cl- phenyl-C(O)OMe) | 290 | 470 | ND | Negligible | ND |
| 6a | (HO-, MeO-acrylate phenyl-C(O)OMe) | 400 | 550 | 1200 | 1 | 0.5% |
| 7a | (HO-, Cl-, MeO-acrylate phenyl-C(O)OMe) | 400 | 550 | 7400 | 10.6 | 5.2% |

TABLE 9-continued

Spectroscopic fluorescence parameters measured for selected phenol-benzoate derivatives in PBS 7.4

| Phenol-benzoate | | λ max$_{ex}$ [nm] | λ max$_{em}$ [nm] | ε $_{400\ nm}$ | Relative fluorescence emission | ΦFluorescence |
|---|---|---|---|---|---|---|
| 8a | 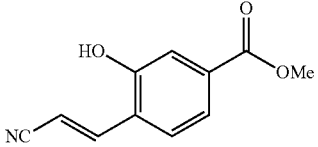 [SMILES: COC(=O)c1ccc(/C=C/C#N)c(O)c1] | 400 | 525 | 2200 | 4.7 | 7.0% |
| 9a | 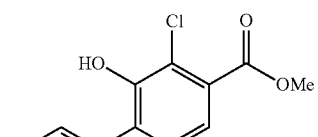 | 400 | 525 | 7700 | 18.0 | 29.8% |

To test this hypothesis, we synthesized five different adamantylidene-dioxetane luminophores with unmasked phenol functional group (Table 10). Upon deprotonation of the phenol, the luminophores undergo chemiexcitation decomposition to release the different benzoates (shown in Table 9) in their exited state. Next, we measured the chemiluminescence emission spectra and total light emission of the luminophores, under physiological conditions. The molecular structure of the dioxetane-luminophores and their chemiluminescence parameters are summarized in Table 10. Predictably, the chemiluminescence emission spectra of the dioxetane-luminophores overlap with the fluorescence emission spectra of their corresponded benzoates (see FIG. 11).

TABLE 10

Chemiluminescence parameters of adamantylidene-dioxetanes 5b-9b

| Dioxetane-luminophore | | λ max$_{CL}$ [nm] | T$_{1/2}$ min | Relative CL emission | Φ$_{CL(H2O)}$ % |
|---|---|---|---|---|---|
| 5b | 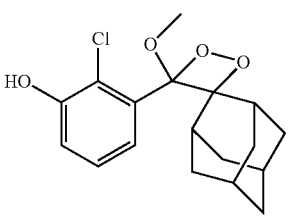 [SMILES: COC1(c2cccc(O)c2Cl)OOC12C1CC3CC(C1)CC2C3] | 470 | 17 | 1 | 3.2 × 10$^{-3}$ |
| 6b | 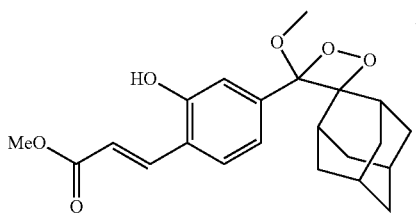 [SMILES: COC(=O)/C=C/c1ccc(C2(OC)OOC23C2CC4CC(C2)CC3C4)cc1O] | 540 | 23 | 724 | 2.3 |
| 7b | 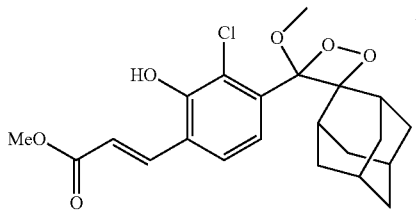 [SMILES: COC(=O)/C=C/c1ccc(C2(OC)OOC23C2CC4CC(C2)CC3C4)c(Cl)c1O] | 540 | 7 | 780 | 2.5 |

TABLE 10-continued

Chemiluminescence parameters of adamantylidene-dioxetanes 5b-9b

| Dioxetane-luminophore | λ max$_{CL}$ [nm] | T$_{1/2}$ min | Relative CL emission | Φ$_{CL(H2O)}$ % |
|---|---|---|---|---|
| 8b | 525 | 22 | 2295 | 7.4 |
| 9b | 525 | 10 | 3043 | 9.8 |

The dioxetane-luminophores exhibited a chemiluminescent exponential decay kinetic profile of with varied T I12. Dioxetane 5b, was used as a reference compound as its chemiluminescence quantum yield under aqueous conditions is known (3.2×10$^{-3}$%) (Trofimov et al., 1996; Edwards et al., 1994). As mentioned above, the chemiluminescence emission of dioxetane 5b in water is extremely weak; however, dioxetane-luminophores 6b, 7b, 8b and 9b exhibited remarkably strong chemiluminescence emission signal upon their deprotonation in PBS 7.4. Luminophore 6b (with methyl-acrylate substituent) showed emission signal, which is about 700-fold stronger than that of dioxetane 5b with chemiluminescence quantum yield of 2.3%. Luminophore 7b (with the methyl-acrylate and additional chlorine substituent) showed similar signal enhancement with faster kinetic profile relative to luminophore 6b (T$_{1/2}$ of 7 min vs. 23 min). Luminophore 9b (with the acrylonitrile and additional chlorine substituent) showed the highest enhancement of chemiluminescence emission; about 3000-fold in comparison to that of dioxetane 5b with chemiluminescence quantum yield of 9.8%. Similar faster kinetic profile was observed when the chlorine substituent was present on the luminophore (T$_{1/2}$ of 10 min for dioxetane 9b vs. 22 min for dioxetane 8b).

Figure 12A:
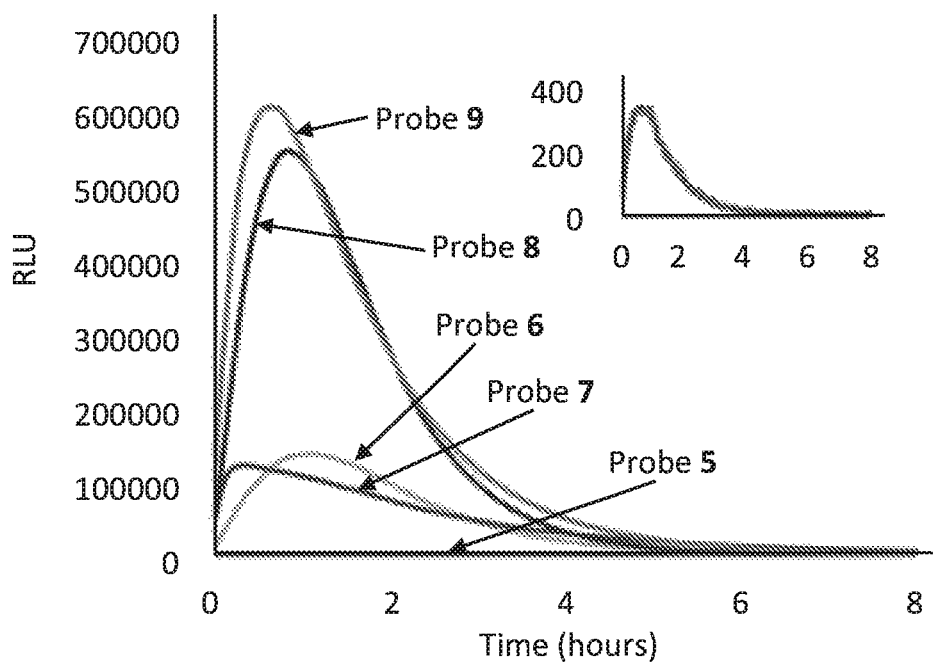
FIGS. 12A-12B show chemiluminescence kinetic profiles of Probes 5, 6, 7, 8 and 9 [1 μM] in PBS, pH 7.4 (10% DMSO) in the presence of 1.5 units/mL β-galactosidase at room temp (12A; the inset shows the kinetic profile of Probe 5); and total emitted photons (12B).
Figure 12B:
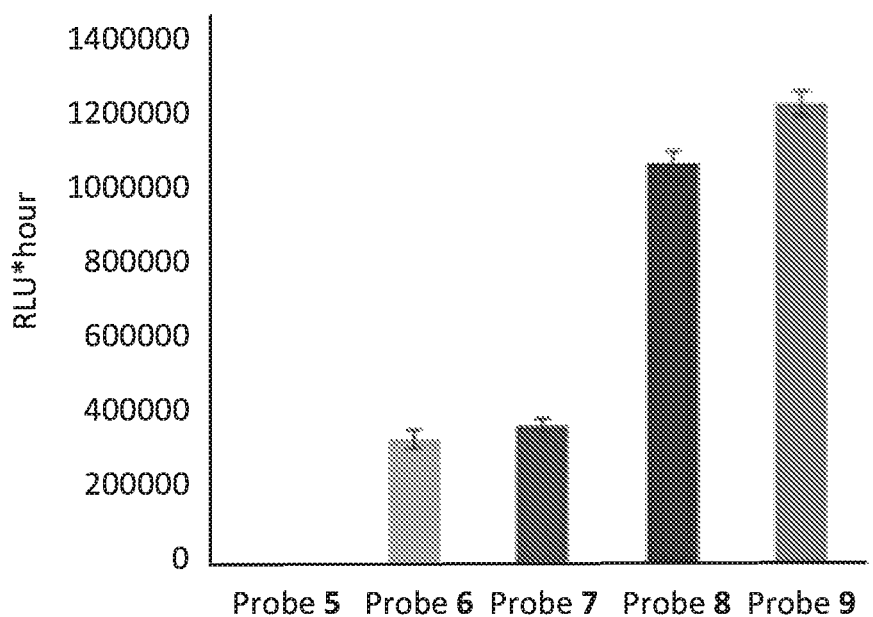

Turn-ON chemiluminescence probes can be simply prepared by masking of the phenol functional group of the dioxetane-luminophores with an enzyme responsive substrate. To evaluate this option, we synthesized five different adamantylidene-dioxetane probes, using dioxetane-luminophores 5b-9b, where the phenol is masked with a triggering substrate suitable for activation by β-galactosidase (Probes 5-9, see Schemes 21-22). To avoid steric interference (as a result of the ortho-substituent) at the enzyme cleavage-site, a short self-immolative spacer was installed in Probes 6-9, between the phenolic oxygen and the galactose substrate (Amir et al., 2003; Gnaim and Shabat, 2014; Sagi et al., 2008). Next, we measured the light chemiluminescence emission of the probes, as a function of time, in the presence and in the absence of β-galactosidase. The kinetic profile of the probes' chemiluminescence signal and their relative emission intensities are shown in FIG. 12.

The probes exhibited a typical chemiluminescent kinetic profile in the presence of β-galactosidase with an initial signal increase to a maximum followed by a slow decrease to zero. While Probes 6-9 exhibited remarkably strong chemiluminescence emission signal under aqueous conditions in the presence of β-galactosidase, Probe 5 produced extremely weak emission (FIG. 12, inset). Probes 6 showed emission signal, which is about 500-fold stronger than that of Probe 5. Probe 7 (with the chlorine substituent) showed similar signal enhancement with faster kinetic profile relative to Probe 6. Similar faster kinetic profile was observed for Probe 9 in comparison to that of Probe 8. Probe 9 showed the highest enhancement of chemiluminescence emission; about 1800-fold, in comparison to that of Probe 5.

Figure 13A:
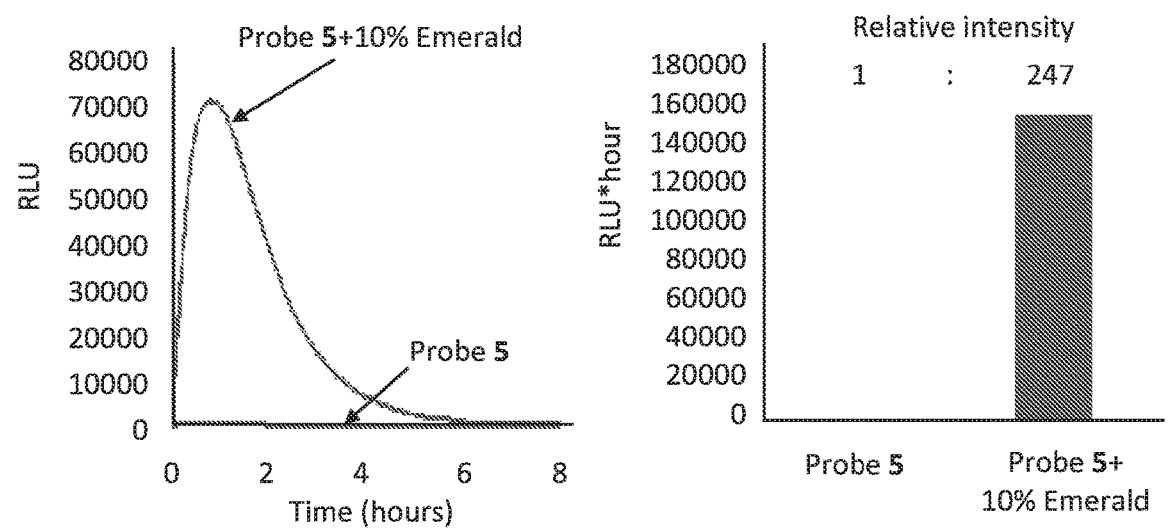
FIGS. 13A-13B show chemiluminescence kinetic profiles of Probe 5 [1 μM] in the presence of 1.5 units/mL β-galactosidase, with and without Emerald-II™ enhancer (10%) in PBS 7.4 (10% DMSO) (left panel), and count of total emitted photon (right panel) (13A); and chemiluminescence kinetic profiles of Probe 5 [1 μM] with Emerald-II™ enhancer (10%) and Probe 9 [1 μM] in PBS 7.4 (10%
Figure 13B:
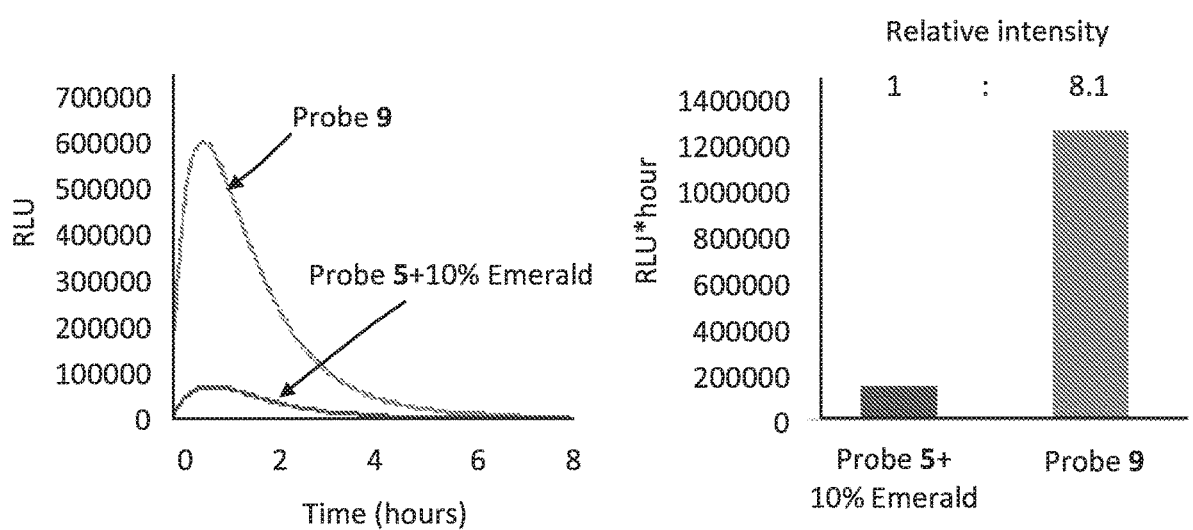

The striking enhancement of chemiluminescence emission obtained by the new dioxetane-luminophores has promoted us to compare the signal intensity of Probe 9 to that of commercial chemiluminescence assays. There are several commercially available chemiluminescence probes based on the adamantylidene-dioxetane. However, since the chemiluminescence emission of these probes is very weak under aqueous conditions, a surfactant-dye adduct (enhancer) is usually added in order to amplify the signal of the assay. The surfactant reduces water-induced quenching by providing a hydrophobic environment for the chemiluminescent reaction that transfers the emitted light to excite the nearby fluorogenic dye. Consequently, the low-efficiency luminescence process is amplified significantly in aqueous medium (Schaap et al., 1989). Commercially available Emerald-II™ enhancer (10%) was added to Probe 5 in the presence of β-galactosidase (in PBS 7.4) and its chemiluminescence emission was compared to that of Probe 6. The obtained results are presented in FIG. 13. Emerald-II™ enhancer amplifies the chemiluminescence emission of Probe 5 by 248-fold (FIG. 13A). Remarkably, the chemiluminescence emission signal obtained by Probe 9 is more than 8-fold stronger than that of Probe 5 with the Emerald-II™ enhancer (FIG. 13B) under physiological conditions. This unprecedented result suggests that a simple small molecule dioxetane compound like Probe 9 can produce chemiluminescence emission, which is about one order of magnitude stronger than the signal produced by a two component-system (Probe 5 and Emerald-II™ enhancer). Since our probes produce under aqueous conditions relatively highly emissive benzoate species, addition of the Emerald-II™ enhancer had only mild amplification effect on their chemiluminescence emission.

The activation of our chemiluminescence probes is based on removal of a protecting group from the phenolic moiety. Therefore, different phenol-protecting groups could be incorporated as triggering substrates for various analytes/enzymes (Redy-Keisar et al., 2014). To demonstrate this modular feature, we synthesized three additional probes for detection of the analytes hydrogen peroxide (Karton-Lifshin et al., 2011) and glutathione (GSH) and the enzyme alkaline-phosphatase (Schaap et al., 1989). Probe 10 was equipped with boronic-ester as a substrate for hydrogen peroxide, Probe 11 with phosphate group as a substrate for alkaline-phosphatase and Probe 12 with dinitro-benzene-sulfonyl group as a substrate for GSH (FIG. 14). The probes were prepared with an acrylic acid or methyl acrylate substituent at the ortho position of the phenolic oxygen. The presence of an ionizable carboxylic acid group has increased significantly their aqueous solubility of Probes 10 and 11 and enabled to conduct evaluation test at a relative high concentration. At concentration of 1 mM (pH 10), Probes 10 and 11 have produced bright green luminescence upon reaction with their analyte/enzyme. As described above, the probes decompose upon their activation to release the excited state of the coresponed benzoate. The acrylate substituent efficiently increases the emissive nature of the released benzoate to produce strong light emission, clearly visible to the naked eye. Probe 12 has relatively moderate aqueous solubility with an applicable concertation range between 1-10 µM.

To evaluate the sensitively and selectivity of Probes 10, 11 and 12 to detect their corresponded analyte/enzyme, we determined the probes' limit of detection (LOD). The probes exhibited very good selectivity towards their analyte of choice under physiological conditions (FIG. 15). Probe 10 could detect hydrogen peroxide with an LOD value of 30 nM, Probe 11 could detect alkaline-phosphatase with an LOD value of 3.9 µU/ml and Probe 12 could detect GSH with an LOD value of 1.7 µM.

Since chemiluminescence is generated through a kinetic profile, its signal intensity, in absolute values, is often weaker in comparison to fluorescence. Therefore, to localize and quantify chemi/bio-luminescence probes at single cell resolution, a suitable microscope (like LV200 by Olympus) is required. We sought to evaluate the ability of our probes to image cells that overexpressed β-galactosidase, by the LV200 microscope. After initial screening for cell-permeability, Probe 7 was selected for the imaging evaluation. HEK293 (transfected by LacZ) and HEK293-WT (control) cells were incubated with Probe 7 and then imaged by the LV200 (FIG. 16). The obtained images clearly support the probe in-vitro activation by endogenously expressed β-galactosidase. Probe 7 was able to produce high quality chemiluminescence images of the HEK293-LacZ cells already with 20 second exposure time (FIG. 16b). No chemiluminescence signal at all was observed by the HEK293-WT cells (FIG. 16d).

Over the past 30 years or so, numerus examples of chemiluminescence probes based on Schaap's dioxetane were reported in the literature (Bronstein et al., 1989; Stevenson et al., 1999; Sabelle et al., 2002; Richard et al., 2007; Richard et al., 2009; Turan and Akkaya, 2014; Cao et al., 2015; Cao et al., 2016; Clough et al., 2016). All of these probes were designed to release upon their activation the original benzoate, which is a weak emissive species under aqueous conditions. In this study, we aimed to redesign Schaap's dioxetane in order to develop chemiluminescence probes that will be highly emissive in biological environment. As explained above, the chemiluminescence efficiency of Schaap's dioxetane is essentially depended on the emissive nature of the obtained excite state benzoate. Thus, we initially sought to look at the fluorescence emission of different benzoates under physiological conditions. We assumed that 1f a substituent can increase the benzoate's fluorescent emission in water, it will similarly be able to intensify the chemiluminescence emission of a corresponded dioxetane probe under physiological conditions. The obtained effect of the acrylate and the acrylonitrile substituents at the ortho position of the phenolic oxygen was indeed incredible. With enhancement of greater than three orders of magnitude, we were able to obtain the most powerful chemiluminescence adamantylidene-dioxetane probe known today suitable for use under aqueous conditions. Interestingly, introduction of the acrylate substituent at the para position of the phenolic oxygen, results with only moderate effect on the fluorescence of the corresponded benzoate and on the chemiluminescence of the adamantylidene-dioxetane.

In commercial chemiluminescence assays signal enhancement is achieved indirectly, by energy transfer to a fluorescent dye (confined in micelles that are shaped by a surfactant). Due to high toxicity consequence, such multi-component probe system is obviously not suitable for cell imaging (Partearroyo et al., 1990). The probes shown in their Study are composed of single component, small molecule with direct mode of chemiluminescence emission and reasonable aqueous solubility. Such characteristics make theses probes ideal for cell imaging applications. Probe 7 was able to provide excellent chemiluminescence cell images based on endogenous β-galactosidase activity. As far as we know, these are the first cell images that are obtained by non-luciferin small molecule based probe with direct chemiluminescence mode of emission.

The pKa value of phenolic benzoates is another factor that significantly affects the chemiluminescence emission of our probes. We have observed that in order to enable the chemiexcitation mechanism under physiological conditions, the pKa of the obtained phenol (after removal of the triggering group) should be around 8.5 or lower. A lower pKa value for the phenol may be especially important for a probe aimed for in vitro use, when the probe penetrates into the cell through endocytosis mechanism (the pH in the endosome is known to be around 6.5 or lower). Probe 7 was selected for cell imaging evaluation as it is composed of a phenol with a pKa value of approximately 7.0.

The modular option to install different triggering substrate on the dioxetane probe, enables one to use our molecules to prepare chemiluminescence probes for various analytes or enzymes of interest. We have demonstrated this option by synthesis and evaluation of four new chemiluminescence probes for detection of β-galactosidase, alkaline-phosphatase, hydrogen peroxide and ubiquitous thiols. The high chemiluminescence efficiency observed by theses probes under aqueous conditions should make them ideal substrates for biochemical tests in the field of immunoassays.

CONCLUSIONS

In summary, we have developed a new molecular methodology to obtain chemiluminescence probes with high efficiency yield under physiological conditions. The methodology is based on the fluorescence emission effect of a substituent on the benzoate species obtained during the chemiexcitation pathway of the Schapp's adamantylidene-dioxetane probe. A striking substituent effect on the chemiluminescence efficiency of the probes was obtained when acrylate and acrylonitrile electron-withdrawing groups were installed. The chemiluminescence quantum yield of the best probe was greater than three orders of magnitude in comparison to standard commercial available adamantylidene-dioxetane probe. So far bio/chemi-luminescence cell imaging was limited to luciferin related probes. One of our new probes was able to provide high quality chemiluminescence cell images based on endogenous activity of β-galactosidase. To date, this is the first demonstration of cell-imaging achieved by non-luciferin small molecule based probe with direct chemiluminescence mode of emission. The notion presented in this study may further lead to development of new efficient chemiluminescence probes for various applications in the field of sensing and imaging

REFERENCES

Amir, R. J.; Pessah, N.; Shamis, M.; Shabat, D. Self-immolative dendrimers. *Angew. Chem. Int. Ed.* 2003, 42 (37), 4494

Bauer, C. R. G. I. T. *Imaging & Microscopy* 2013, 4, 32

Branchini, B. R.; Ablamsky, D. M.; Rosenberg, J. C. *Bioconjugate Chem.* 2010, 21, 2023

Bronstein, I.; Edwards, B.; Voyta, J. C. *J. Biolumin. Chemilumin.* 1989, 4(1), 99

Cao, J.; Lopez, R.; Thacker, J. M.; Moon, J. Y.; Jiang, C.; Morris, S. N.; Bauer, J. H.; Tao, P.; Mason, R. P.; Lippert, A. R. *Chem Sci* 2015, 6(3), 1979

Cao, J.; Campbell, J.; Liu, L.; Mason, R. P.; Lippert, A. R. *Anal. Chem.* 2016, 88 (9), 4995

Chi, C.; Du, Y.; Ye, J.; Kou, D.; Qiu, J.; Wang, J.; Tian, J.; Chen, X. *Theranostics* 2014, 4(11), 1072-1084

Cho, S.; Hwang, 0.; Lee, I.; Lee, G.; Yoo, D.; Khang, G.; Kang, P. M.; Lee, D. *Adv. Funct. Mater.* 2012, 22(19), 4038

Clough, J. M.; Balan, A.; van Daal, T. L. J.; Sijbesma, R. P. *Angew. Chem. Int. Ed.* 2016, 55(4), 1445

Dominguez, A.; Fernandez, A.; Gonzalez, N.; Iglesias, E.; Montenegro, L. *J. Chem. Educ.* 1997, 74, 1227

Edwards, B.; Sparks, A.; Voyta, J. C.; Bronstein, I. in *Bioluminescence and chemiluminescence: fundamentals and applied aspects* (A. K. Campbell, L. J. kricka and P. E. Stanley, eds.); Wiley: Chichester, 1994, 56

Gnaim, S.; Shabat, D. *Acc. Chem. Res.* 2014, 47(10), 2970

Gopinath, R.; Hague, S. J.; Patel, B. K. *J Org Chem,* 2002, 67(16), 5842-5845

Gross, S.; Gammon, S. T.; Moss, B. L.; Rauch, D.; Harding, J.; Heinecke, J.W.; Ratner, L.; Piwnica-Worms, D. *Nat. Med.* 2009, 15(4), 455

Haber, G. P.; White, M. A.; Autorino, R.; Escobar, P. F.; Kroh, M. D.; Chalikonda, S.; Khanna, R.; Forest, S.; Yang, B.; Altunrende, F.; Stein, R. J.; Kaouk, J. H. *Urology* 2010, 76, 1279-1282

Hagiwara, H.; Watanabe, N.; Ijuin, H. K. Heterocycles 2013, 87(1), 65

Hananya, N.; Eldar Boock, A.; Bauer, C. R.; Satchi-Fainaro, R.; Shabat, D. *J. Am. Chem. Soc.* 2016, 138(40), 13438

Ishiyama, T.; Takagi, J.; Ishida, K.; Miyaura, N.; Anastasi, N. R.; Hartwig, J. F. *J. Am. Chem. Soc.* 2002, 124, 390

Jacobson, K. A.; Furlano, D. C.; Kirk, K. L. *J. Fluorine Chem.,* 1988, 39, 339-347

Jathoul, A. P.; Grounds, H.; Anderson, J. C.; Pule, M. A. *Angew. Chem., Int. Ed.* 2014, 53, 13059

Karton-Lifshin, N.; Segal, E.; Omer, L.; Portnoy, M.; Satchi-Fainaro, R.; Shabat, D. *J. Am. Chem. Soc.* 2011, 133(28), 10960

Karton-Lifshin, N.; Albertazzi, L.; Bendikov, M.; Baran, P. S.; Shabat, D. *J. Am. Chem. Soc.* 2012, 134(50), 20412

Kielland, A.; Blom, T.; Nandakumar, K. S.; Holmdahl, R.; Blomhoff, R.; Carlsen, H. *Free Radical Biol. Med.* 2009, 47, 760

Kisin-Finfer, E.; Ferber, S.; Blau, R.; Satchi-Fainaro, R.; Shabat, D. *Bioorg. Med. Chem. Lett.* 2014, 24, 2453

Lee, D.; Khaja, S.; Velasquez-Castano, J. C.; Dasari, M.; Sun, C.; Petros, J.; Taylor, W. R.; Murthy, N. *Nat Mater* 2007, 6(10), 765

Lee, Y. D.; Lim, C. K.; Singh, A.; Koh, J.; Kim, J.; Kwon, I. C.; Kim, S. *ACS nano* 2012, 6(8), 6759

Lee, E. S.; Deepagan, V. G.; You, D. G.; Jeon, J.; Yi, G. R.; Lee, J. Y.; Lee, D. S.; Suh, Y. D.; Park, J. H. *Chem. Commun.* (Camb.) 2016, 52(22), 4132

Li, P.; Liu, L.; Xiao, H.; Zhang, W.; Wang, L.; Tang, B. *J. Am. Chem. Soc.* 2016, 138(9), 2893

Lim, C. K.; Lee, Y. D.; Na, J.; Oh, J. M.; Her, S.; Kim, K.; Choi, K.; Kim, S; Kwon, I. C. *Adv. Funct. Mater.* 2010, 20(16), 2644

Liu, L.; Mason, R. P. *PLoS One* 2010, 5, e12024

Loening, A. M.; Dragulescu-Andrasi, A.; Gambhir, S. S. *Nat. Methods* 2010, 7, 5

Matsumoto, M.; Arai, N.; Watanabe, N. *Tetrahedron Lett.* 1996, 37(47), 8535

Matsumoto, M.; Sakuma, T.; Watanabe, N. Luminescence 2001, 16(4), 275

Matsumoto, M.; Mizoguchi, Y.; Motoyama, T.; Watanabe, N. *Tetrahedron Lett.* 2001, 42(50), 8869

Matsumoto, M.; Sakuma, T.; Watanabe, N. *Tetrahedron Lett.* 2002, 43(49), 8955

Matsumoto, M. *J. Photochem. Photobiol.,* C2004, 5, 27

Matsumoto, M.; Akimoto, T.; Matsumoto, Y.; Watanabe, N. *Tetrahedron Lett.* 2005, 46(36), 6075

Matsumoto, M.; Watanabe, N.; Hoshiya, N.; Ijuin, H. K. *Chem. Rec.* 2008, 8, 213

McCutcheon, D. C.; Paley, M. A.; Steinhardt, R. C.; Prescher, J. A. *J. Am. Chem. Soc.* 2012, 134, 7604

Merényi, G.; Lind, J.; Eriksen, T. E. *J. Biolumin. Chemilumin.* 1990, 5(1), 53

Mieog, J. S.; Troyan, S. L.; Hutteman, M.; Donohoe, K. J.; van der Vorst, J. R.; Stockdale, A.; Liefers, G. J.; Choi, H. S.; Gibbs-Strauss, S. L.; Putter, H.; Gioux, S.; Kuppen, P. J.; Ashitate, Y.; Lowik, C.W.; Smit, V. T.; Oketokoun, R.; Ngo, L. H.; van de Velde, C. J.; Frangioni, J. V.; Vahrmeijer, A. L. *Annals of surgical oncology* 2011, 18, 2483-2491

Miller, K.; Erez, R.; Segal, E.; Shabat, D.; Satchi-Fainaro, R. *Angew Chem Int Ed Engl.* 2009, 48(16), 2949-2954

Park, J. Y.; Gunpat, J.; Liu, L.; Edwards, B.; Christie, A.; Xie, X. J.; Kricka, L. J.; Mason, R. P. Luminescence 2014, 29, 553

Partearroyo, M. A.; Ostolaza, H.; Goni, F. M.; Barberá-Guillem, E. *Biochem. Pharmacol.* 1990, 40(6), 1323

Porterfield, W. B.; Jones, K. A.; McCutcheon, D. C.; Prescher, J. A. *J. Am. Chem. Soc.* 2015, 137, 8656

Redy-Keisar, O.; Kisin-Finfer, E.; Ferber, S.; Satchi-Fainaro, R.; Shabat, D. *Nat. Protoc.* 2014, 9(1), 27-36

Redy-Keisar, O.; Huth, K.; Vogel, U.; Lepenies, B.; Seeberger, P. H.; Haag, R.; Shabat, D. *Org. Biomol. Chem.* 2015a, 13, 4727

Redy-Keisar, O.; Ferber, S.; Satchi-Fainaro, R.; Shabat, D. ChemMedChem 2015b, 10(6), 999

Richard, J. A.; Jean, L.; Romieu, A.; Massonneau, M.; Noack-Fraissignes, P.; Renard, P. Y. *Org. Lett.* 2007, 9(23), 4853

Richard, J. A.; Jean, L.; Schenkels, C.; Massonneau, M.; Romieu, A.; Renard, P. Y. *Org. Biomol. Chem.* 2009, 7(14), 2941

Roda, A.; Guardigli, M.; Pasini, P.; Mirasoli, M.; Michelini, E.; Musiani, M. *Anal. Chim. Acta* 2005, 541, 25

Roda, A.; Guardigli, M. *Anal. Bioanal. Chem.* 2012, 402, 69

Sabelle, S.; Renard, P. Y.; Pecorella, K.; de Suzzoni-Dezard, S.; Creminon, C.; Grassi, J.; Mioskowski, C. *J. Am. Chem. Soc.* 2002, 124(17), 4874

Sagi, A.; Weinstain, R.; Karton, N.; Shabat, D. *J. Am. Chem. Soc.* 2008, 130(16), 5434

Schaap, A. P.; Handley, R. S.; Giri, B. P. *Tetrahedron Lett.* 1987a, 28(9), 935

Schaap, A. P.; Chen, T. S.; Handley, R. S.; DeSilva, R.; Giri, B. P. *Tetrahedron Lett.* 1987b, 28(11), 1155

Schaap, A. P.; Sandison, M. D.; Handley, R. S. *Tetrahedron Lett.* 1987c, 28(11), 1159

Schaap, A. P.; Akhavan, H.; Romano, L. *J. Clin. Chem.* 1989, 35(9), 1863

Segal, E.; Pan, H.; Ofek, P.; Udagawa, T.; Kopeckova, P.; Kopecek, J.; Satchi-Fainaro, R. *PLoS One* 2009, 4(4), e5233

Shuhendler, A. J.; Pu, K.; Cui, L.; Uetrecht, J. P.; Rao, *J. Nat. Biotechnol.* 2014, 32(4), 373

Silva, S. M.; Casallanovo, F.; Oyamaguchi, K. H.; Ciscato, L. F. L. M.; Stevani, C. V.; Baader, W. J. Luminescence 2002, 17(5), 313

Steinhardt, R. C.; O'Neill, J. M.; Rathbun, C. M.; McCutcheon, D. C.; Paley, M. A.; Prescher, J. A. *Chem. Eur. J.* 2016, 22, 3671

Stevenson, J. D.; Dietel, A.; Thomas, N. R.; *Chem. Commun.* 1999, 20, 2105-2106

Stern, L.; Perry, R.; Ofek, P.; Many, A.; Shabat, D.; Satchi-Fainaro, R. *Bioconjug Chem.* 2009, 20(3), 500-510

Torchilin, V. P. *J. Controlled Release* 2001, 73, 137

Trofimov, A. V.; Mielke, K.; Vasil'ev, R. F.; Adam, W. Photochem. Photobiol. 1996, 63 (4), 463

Troyan, S. L.; Kianzad, V.; Gibbs-Strauss, S. L.; Gioux, S.; Matsui, A.; Oketokoun, R.; Ngo, L.; Khamene, A.; Azar, F.; Frangioni, J. V. *Annals of surgical oncology* 2009, 16, 2943-2952

Tseng, J. C.; Kung, A. L. *J. Biomed. Sci.* 2015, 22, 45

Turan, I. S.; Akkaya, E. U. *Org. Lett.* 2014, 16(6), 1680

Van de Bittner, G. C.; Bertozzi, C. R.; Chang, C. J. *J. Am. Chem. Soc.* 2013, 135, 1783

Wakimoto, R.; Kitamura, T.; Ito, F.; Usami, H.; Moriwaki, H. *Appl. Catal.*, B 2015, 166-167, 544-550

Watanabe, N.; Kino, H.; Watanabe, S.; Ijuin, H. K.; Yamada, M.; Matsumoto, M. *Tetrahedron* 2012, 68, 6079

Weissleder, R. *Nat. Biotechnol.* 2001, 19, 316

Zhang, N.; Francis, K. P.; Prakash, A.; Ansaldi, D. *Nat. Med.* 2013, 19(4), 500

What is claimed is:

1. A conjugate of the formula IIIa or IIIb:

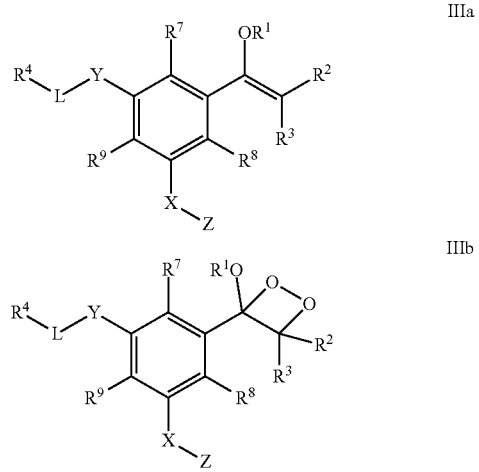

wherein $R^1$ is selected from the group consisting of a linear or branched $(C_1-C_{18})$alkyl, and $(C_3-C_7)$cycloalkyl;

$R^2$ and $R^3$ each independently is selected from the group consisting of a branched $(C_3-C_{18})$alkyl and $(C_3-C_7)$cycloalkyl, or $R^2$ and $R^3$ together with the carbon atom to which they are attached form a fused, spiro or bridged cyclic or polycyclic ring;

$R^4$ is a caging group;

L is absent or is a linker of the formula L1, L2 or L3, optionally substituted at the aromatic ring with one or more substituents each independently selected from the group consisting of $(C_1-C_{18})$alkyl and $(C_3-C_7)$cycloalkyl, wherein M is absent or is —O— or —NH—, and the asterisk represents the point of attachment to the group Y, provided that M is —O— or —NH— unless $R^4$ is 4,4,5,5-tetramethyl-1,3,2-dioxaborolanyl or —B(OH)$_2$;

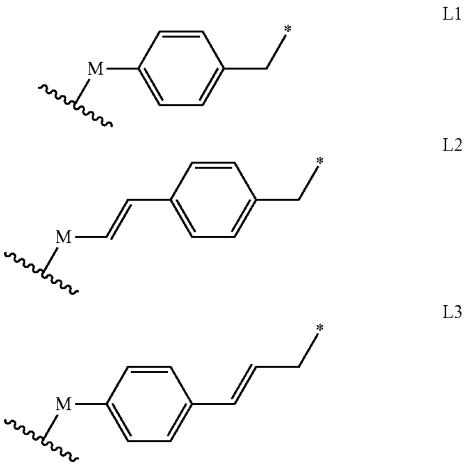

Y is absent or is —O—, provided that Y is —O— unless $R^4$ is 4,4,5,5-tetramethyl-1,3,2-dioxaborolanyl or —B(OH)$_2$, and L is absent;

R⁷, R⁸ and R⁹ each independently is H, or an electron acceptor group selected from the group consisting of halogen, —NO₂, —CN, —COOR¹⁰, —C(=O)R¹⁰ and —SO₂R¹⁰;

R¹⁰ each independently is H or —(C₁-C₁₈)alkyl;

X is a linker of the formula —X₁—X₂—, wherein X₁ is selected from the group consisting of (C₁-C₁₈)alkylene, (C₂-C₁₈)alkenylene, (C₂-C18)alkynylene, (C₃-C₇)cycloalkylene, (C₃-C₇)cycloalkenylene, (C₆-C₁₄)arylene-diyl, (C₁-C₁₈)alkylene-(C₆-C₁₄)arylene-diyl, heteroarylenediyl, and (C₁-C₁₈)alkylene-heteroarylenediyl, said (C₁-C₁₈)alkylene, (C₂-C₁₈)alkenylene, (C₂-C₁₈)alkynylene, (C₃-C₇)cycloalkylene, (C₃-C₇)cycloalkenylene, (C₆-C₁₄)arylene-diyl, or heteroarylenediyl being optionally substituted by one or more groups each independently selected from the group consisting of halogen, —COR¹⁰, —COOR¹⁰, —OCOOR¹⁰, —OCON(R¹⁰)₂, CN, —NO₂, SR OR N(R¹⁰)₂, CON(R¹⁰)₂, —SO₂R¹⁰, —SO₃H, —S(=O)R¹⁰, (C₆-C₁₀)aryl, (C₁-C₄)alkylene-(C₆-C₁₀)aryl, heteroaryl, and (C₁-C₄)alkylene-hetero aryl, and said (C₁-C₁₈)alkylene, (C₂-C₁₈)alkenylene, or (C₂-C₁₈)alkynylene being further optionally interrupted by one or more identical or different heteroatoms selected from the group consisting of S, O and N, and/or at least one group each independently selected from the group consisting of —NH—CO—, —CO—NH—, —N(C₁-C₈alkyl)-, —N(C₆-C₁₀aryl)-, (C₆-C₁₀)arylene-diyl, and heteroarylenediyl; and X₂ is absent or is —C(O)—; and Z is a moiety of a fluorophore selected from the group consisting of a fluorescein-based compound, rhodamine-based compound, coumarin-based compound, cyanine dye selected from the group consisting of Cy5, Cy5.5, Cy5.18, Cy7, Cy7.18, and QCy, or borondipyrromethene.

2. The conjugate of claim 1, wherein:

(i) R¹ is a linear or branched (C₁-C₈)alkyl; or (ii) R² and R³ together with the carbon atom to which they are attached form a fused, spiro or bridged polycyclic ring; or (iii) said R⁴ caging group is selected from the group consisting of:

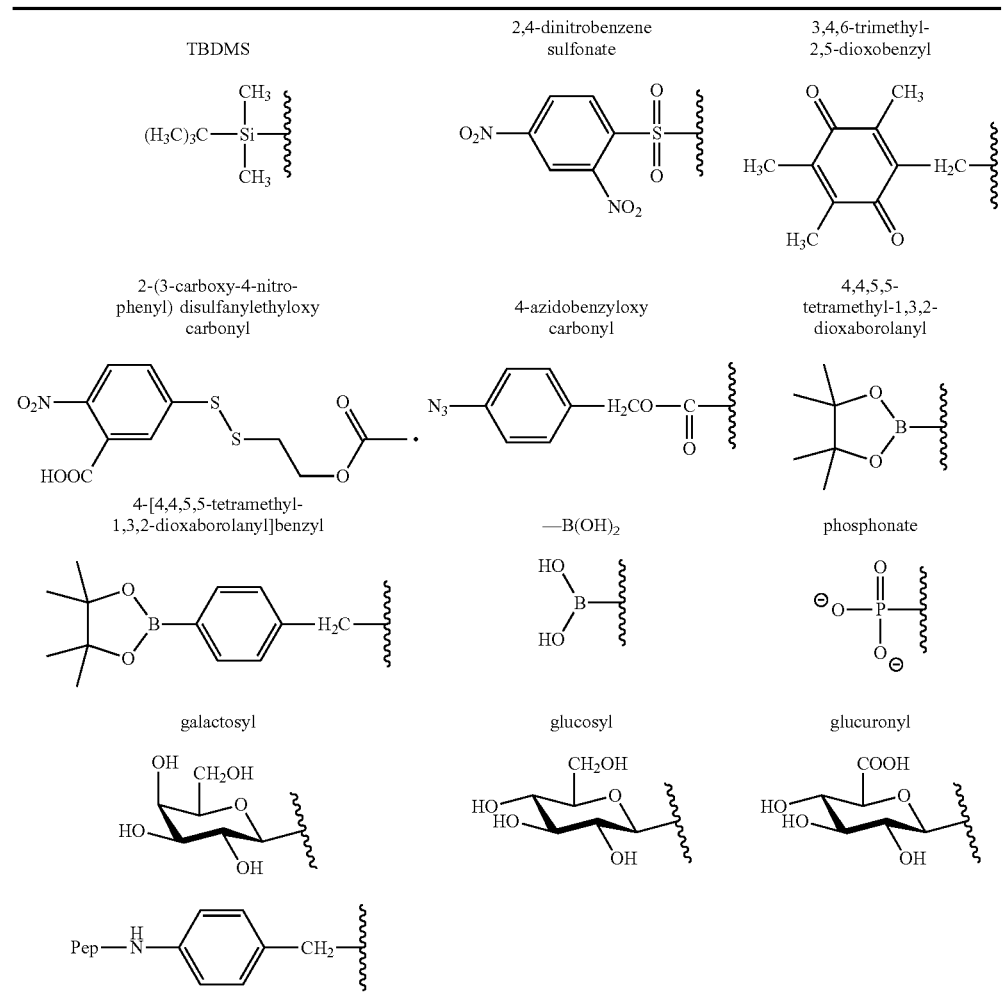

wherein Pep is a peptide consisting of at least two amino acid residues and linked via a carboxylic group thereof; or (iv) at least one of R⁷, R⁸ and R⁹ is H, and the other of R⁷, R⁸ and R⁹ each independently is an electron acceptor group selected from the group consisting of halogen, —NO₂ and —CN; or (v) $X_1$ is $(C_1$-$C_{18})$alkylene, $(C_6$-$C_{14})$arylene-diyl, or $(C_1$-$C_{18})$alkylene-$(C_6$-$C_{14})$arylene-diyl, optionally substituted by one or more groups each independently selected from the group consisting of halogen, —COH, —COOH, —OCOOH, —OCONH$_2$, —CN, —NO$_2$, —SH, —OH, —NH$_2$, —CONH$_2$, —SO$_2$H, —SO$_3$H, —S(=O)H, $(C_6$-$C_{10})$aryl, $(C_1$-$C_4)$alkylene-$(C_6$-$C_{10})$aryl, heteroaryl, and $(C_1$-$C_4)$alkylene-heteroaryl, and said $(C_1$-$C_{18})$alkylene being further optionally interrupted by one or more identical or different heteroatoms selected from the group consisting of S, O and N, and/or at least one group each independently selected from the group consisting of —NH—CO—, —CO—NH—, —N($C_1$-$C_8$alkyl)-, —N($C_6$-C10)aryl)-, $(C_6$-$C_{10})$arylene-diyl, and heteroarylenediyl; and $X_2$ is —C(O)—; or (vi) Z is selected from the group consisting of Z1, Z2, Z3, Z4, Z5, and Z6:

Z1

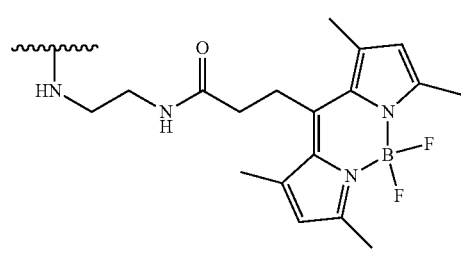

Z2

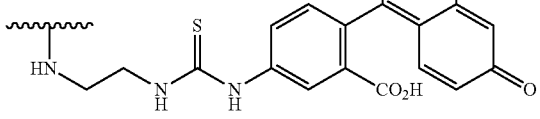

Z3

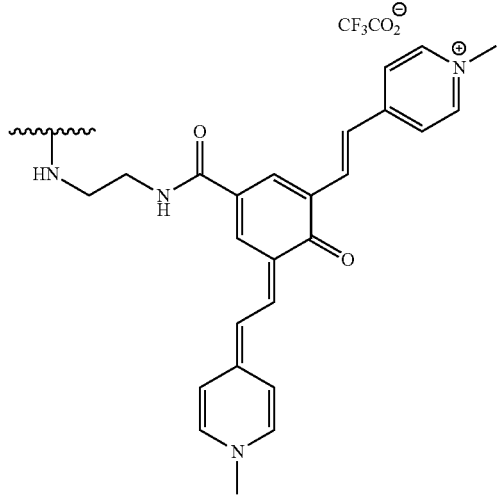 [SMILES: *NCCNC(=O)C1=C/C(=C\C=C2C=CN(C)C=C2)C(=O)C(/C=C/c2cc[n+](C)cc2)=C1 ; "CF3CO2"]

Z4

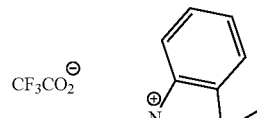

Z5

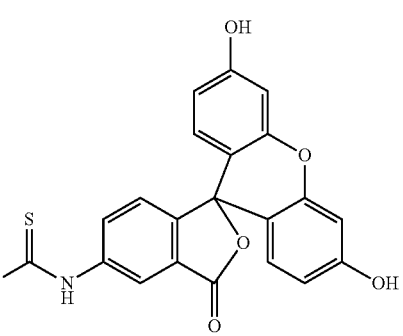

Z6

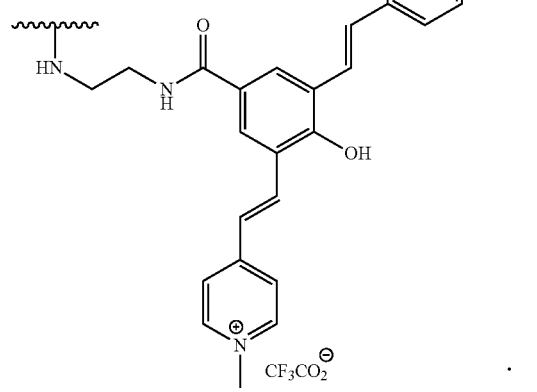

3. The conjugate of claim 2, wherein $R^2$ and $R^3$ together with the carbon atom to which they are attached form adamantyl.

4. The conjugate of claim 2, wherein $X_1$ is —(CH$_2$)-para-phenylene; and $X_2$ is —C(O)—.

5. The conjugate of claim 1, wherein:
$R^1$ is a linear or branched $(C_1-C_8)$alkyl;
$R^2$ and $R^3$ together with the carbon atom to which they are attached form a fused, spiro or bridged polycyclic ring; at least one of $R^7$, $R^8$ and $R^9$ is H, and the other of $R^7$, $R^8$ and $R^9$ each independently is an electron acceptor group selected from the group consisting of halogen, —$NO_2$ and —CN; and
X is a linker of the formula —$X_1$—$X_2$—, wherein $X_1$ is $(C_1-C_{18})$alkylene, $(C_6-C_{14})$arylene-diyl, or $(C_1-C_{18})$alkylene-$(C_6-C_{14})$arylene-diyl, optionally substituted by one or more groups each independently selected from the group consisting of halogen, —COH, —COOH, —OCOOH, —OCONH$_2$, —CN, —NO$_2$, —SH, —OH, —NH$_2$, —CONH$_2$, —SO$_2$H, —SO$_3$H, —S(=O)H, $(C_6-C_{10})$aryl, $(C_1-C_4)$alkylene-$(C_6-C_{10})$aryl, heteroaryl, and $(C_1-C_4)$alkylene-heteroaryl, and said $(C_1-C_{18})$alkylene being further optionally interrupted by one or more identical or different heteroatoms selected from the group consisting of S, O and N, and/or at least one group each independently selected from the group consisting of —NH—CO—, —CO—NH—, —N($C_1-C_8$alkyl)-, —N($C_6-C_{10}$aryl)-, $(C_6-C_{10})$arylene-diyl, and heteroarylenediyl; and $X_2$ is —C(O)—.

6. The conjugate of claim 5, wherein $R^1$ is methyl; $R^2$ and $R^3$ together with the carbon atom to which they are attached form adamantly; $X_1$ is —(CH$_2$)-para-phenylene; and $X_2$ is —C(O)—.

7. The conjugate of claim 1, wherein (i) Y is —O—, L is absent or a linker of the formula L1, L2 or L3, wherein M is —O— or —NH—, and $R^4$ is a caging group; or (ii) Y is absent, L is absent, and $R^4$ is 4,4,5,5-tetramethyl-1,3,2-dioxaborolanyl or —B(OH)$_2$.

8. The conjugate of claim 7, wherein $R^1$ is methyl; $R^2$ and $R^3$ together with the carbon atom to which they are attached form adamantly; $X_1$ is —(CH$_2$)-para-phenylene; $X_2$ is —C(O)—; Z is selected from the group consisting of Z1, Z2, Z3, Z4, Z5, and Z6; and
(i) $R^7$, $R^8$ and $R^9$ are H; Y is —O—; L is absent; and $R^4$ is TBDMS; or
(ii) $R^7$ is $C_1$; $R^8$ and $R^9$ are H; Y is —O—; L is absent; and $R^4$ is galactosyl.

9. A composition comprising a carrier, and a conjugate according to claim 1.

10. A method for diagnostics or in vivo imaging comprising:
applying a composition according to claim 9 to a biological tissue or administering a composition according to claim 9 to a subject, wherein $R^4$ of the conjugate of formula IIIa/IIIb is a caging group cleavable by an analyte, wherein upon exposure to said analyte, group $R^4$ is cleaved from the compound of formula IIIa/IIIb, thereby generating a phenolate-dioxetane compound and initiating a chemically initiated electron exchange luminescence (CIEEL) mechanism, which results in excitation of the fluorophore group Z of said conjugate that is then decays to its ground-state through emission of light; and
imaging to detect the emission of light.

* * * * *